(12) United States Patent
Hunter et al.

(10) Patent No.: US 6,177,258 B1
(45) Date of Patent: Jan. 23, 2001

(54) FLEA PROTEASE PROTEINS AND USES THEREOF

(75) Inventors: Shirley Wu Hunter; Gary L. Stiegler; Patrick J. Gaines, all of Ft. Collins, CO (US)

(73) Assignee: Heska Corporation, Ft. Collins, CO (US)

( * ) Notice: Under 35 U.S.C. 154(b), the term of this patent shall be extended for 0 days.

(21) Appl. No.: 09/004,731

(22) Filed: Jan. 8, 1998

Related U.S. Application Data

(60) Division of application No. 08/749,699, filed on Nov. 15, 1996, which is a continuation-in-part of application No. 08/484,211, filed on Jun. 7, 1995, now Pat. No. 5,972,645, and a continuation-in-part of application No. 08/482,130, filed on Jun. 7, 1995, now Pat. No. 5,962,257, and a continuation-in-part of application No. 08/485,443, filed on Jun. 7, 1995, and a continuation-in-part of application No. 08/485,455, filed on Jun. 7, 1995, now Pat. No. 5,712,143, said application No. 08/484,211, filed on Jun. 7, 1995, is a continuation-in-part of application No. 08/326,773, filed on Oct. 18, 1994, now Pat. No. 5,766,609, said application No. 08/482,130, filed on Jun. 7, 1995, is a continuation-in-part of application No. 07/806,482, filed on Dec. 13, 1991, now Pat. No. 5,356,622.

(51) Int. Cl.$^7$ ............... C12Q 1/37; C12N 9/48; C12N 9/50
(52) U.S. Cl. ............ 435/23; 435/212; 435/219; 435/24; 530/324; 530/329; 530/350
(58) Field of Search ................. 514/2, 12, 17; 530/324, 329, 350; 424/184.1, 185.1; 435/212, 219, 18, 23, 24

(56) References Cited

U.S. PATENT DOCUMENTS 5,712,143 * 1/1998 Grieve et al. .
5,962,257 * 10/1999 Grieve et al. .
5,972,645 * 10/1999 Grieve et al. .

FOREIGN PATENT DOCUMENTS

WO96/11706 * 4/1996 (WO) .

OTHER PUBLICATIONS

Gaines et al., *Insert Molecular Biology*, 8(1):11–22, 1999.*

* cited by examiner

Primary Examiner—Marianne P. Allen
(74) Attorney, Agent, or Firm—Sheridan Ross P.C.

(57) ABSTRACT

The present invention relates to flea serine protease proteins and flea cysteine protease proteins; to flea serine protease and cysteine protease nucleic acid molecules, including those that encode such proteins; to antibodies raised against such proteins; and to compounds that inhibit flea serine protease and/or cysteine protease activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

3 Claims, No Drawings

FLEA PROTEASE PROTEINS AND USES THEREOF

CROSS-REFERENCE TO RELATED APPLICATIONS

The present invention is a divisional of U.S. patent application Ser. No. 08/749,699, filed Nov. 15, 1996, which is a continuation-in-part of U.S. patent application Ser. Nos. 08/484,211 (issued as U.S. Pat. No. 5,972,645 on Oct. 26, 1999), 08/482,130 (issued as U.S. Pat. No. 5,962,257 on Oct. 5, 1999), 08/485,443, and 08/485,455 (issued as U.S. Pat. No. 5,712,143 on Jan. 27, 1998), each of which was filed on Jun. 7, 1995 and each of which is a continuation-in-part of U.S. Patent Application Serial No. 08/326,773, filed Oct. 18, 1994 which issued as U.S. Pat. No. 5,766,609 on Jun. 16, 1998, and which is a continuation-in-part of U.S. patent application Ser. No. 07/806,482, filed Dec. 13, 1991, which issued as U.S. Pat. No. 5,356,622 on Oct. 18, 1994. The present application is also a continuation-in-part of U.S. patent application Ser. No. 08/326,773, ibid., as well as of WO 96/11706, the international publication date of which is Apr. 25, 1996. WO 96/11706 claims priority to U.S. patent application Ser. Nos. 08/326,773, 08/484,211, 08/482,130, 08/485,443 and 08/485,455, ibid. Each of the applications referred to in this section is incorporated herein by reference in its entirety.

FIELD OF THE INVENTION

The present invention relates to novel flea protease proteins and their use to reduce flea infestation of animals. The present invention also relates to the use of anti-flea protease antibodies and other compounds that reduce flea protease activity to reduce flea infestation of animals.

BACKGROUND OF THE INVENTION

Fleas, which belong to the insect order Siphonaptera, are obligate ectoparasites for a wide variety of animals, including birds and mammals. Flea infestation of animals is of health and economic concern because fleas are known to cause and/or transmit a variety of diseases. Fleas cause and/or carry infectious agents that cause, for example, flea allergy dermatitis, anemia, murine typhus, plague and tapeworm. In addition, fleas are a problem for animals maintained as pets because the infestation becomes a source of annoyance for the pet owner who may find his or her home generally contaminated with fleas which feed on the pets. As such, fleas are a problem not only when they are on an animal but also when they are in the general environment of the animal.

The medical and veterinary importance of flea infestation has prompted the development of reagents capable of controlling flea infestation. Commonly encountered methods to control flea infestation are generally focussed on use of insecticides in formulations such as sprays, shampoos, dusts, dips, or foams, or in pet collars. While some of these products are efficacious, most, at best, offer protection of a very limited duration. Furthermore, many of the methods are often not successful in reducing flea populations on the pet for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Additional anti-flea products include non-toxic reagents such as insect growth regulators (IGRs), including methoprene, which mimics flea hormones and affect flea larval development.

An alternative method for controlling flea infestation is the use of flea vaccines to be administered to animals prior to or during flea infestation. However, despite considerable interest in developing anti-flea reagents, no flea vaccine presently exists.

SUMMARY OF THE INVENTION

The present invention relates to flea serine protease proteins, to flea aminopeptidase proteins, and to flea cysteine protease proteins; to flea serine protease, aminopeptidase and/or cysteine protease nucleic acid molecules, including those that encode such proteins; to antibodies raised against such proteins; and to compounds that inhibit flea serine protease, aminopeptidase and/or cysteine protease activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

One embodiment of the present invention is an isolated nucleic acid molecule that hybridizes under stringent hybridization conditions with a gene including a serine protease gene comprising a nucleic acid sequence including a nucleic acid molecule including SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43 and/or SEQ ID NO:45, and a cysteine protease gene comprising a nucleic acid molecule selected from the group consisting of SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94.

The present invention also includes a nucleic acid molecule that hybridizes under stringent hybridization conditions with a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95, or with a nucleic acid sequence that is a complement of any of the nucleic acid sequences. A preferred nucleic acid sequence of the present invention includes a nucleic acid molecule comprising a nucleic acid sequence including SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43 and SEQ ID NO:45, SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94, and allelic variants thereof.

The present invention also includes an isolated protein encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and SEQ ID NO:95.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Yet another embodiment of the present invention is a therapeutic composition that is capable of reducing hematophagous ectoparasite infestation. Such a therapeutic composition includes an excipient and a protective compound including: an isolated protein or mimetope thereof encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and SEQ ID NO:95; an isolated nucleic acid molecule that hybridizes under stringent hybridization conditions with a gene comprising a nucleic acid sequence including SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43, SEQ ID NO:45, SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and SEQ ID NO:94; an isolated antibody that selectively binds to a protein encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and SEQ ID NO:95; an inhibitor of protease activity identified by its ability to inhibit the activity of a protein encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and SEQ ID NO:95; and a mixture thereof. Also included in the present invention is a method to reduce flea infestation, comprising the step of administering to the animal a therapeutic composition of the present invention.

Another embodiment of the present invention is a method to identify a compound capable of inhibiting flea protease activity, the method comprising: (a) contacting an isolated flea protease protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and SEQ ID NO:95 with a putative inhibitory compound under conditions in which, in the absence of said compound, the protein has proteolytic activity; and (b) determining if the putative inhibitory compound inhibits the activity. The present invention also includes a kit to to identify a compound capable of inhibiting flea protease activity.

The present invention also includes an isolated flea protease protein that cleaves an immunoglobulin, when the protein is incubated in the presence of the immunoglobulin in about 100 microliters of about 0.2M Tris-HCl for about 18 hours at about 37° C. A preferred protease protein capable of cleaving immunoglbulin comprises an amino acid sequence selected from the group consisting of SEQ ID NO:67, SEQ ID NO:68, SEQ ID NO:69, SEQ ID NO:70, SEQ ID NO:71, SEQ ID NO:72, SEQ ID NO:73 and SEQ ID NO:96.

Another embodiment of the present invention includes a method to identify a compound capable of inhibiting flea immunoglobulin proteinase protein activity, the method comprising: (a) contacting an isolated flea immunoglobulin proteinase protein with a putative inhibitory compound under conditions in which, in the absence of the compound, the protein has immunoglobulin proteinase activity; and (b) determining if the putative inhibitory compound inhibits the activity.

DETAILED DESCRIPTION OF THE INVENTION

The present invention includes the use of compounds that inhibit flea protease activity to protect a host animal from flea infestation. The inventors have discovered that proteases are significant components of the flea midgut and are good targets for immunotherapeutic and/or chemotherapeutic intervention to reduce flea burden both on the host animal and in the immediate (i.e., surrounding) environment of the animal. The inventors have shown, for example, that the viability and/or fecundity of fleas consuming a blood meal is reduced when the blood meal contains compounds that reduce flea protease activity, probably because the compounds interfere with flea digestion and other functions. Compounds that reduce the amount and/or activity of flea proteases without substantially harming the host animal are included in the present invention. Such compounds include flea protease vaccines, anti-flea protease antibodies, flea protease inhibitors, and/or compounds that suppress protease synthesis; such compounds are discussed in more detail below.

One embodiment of the present invention is a method to protect a host animal from flea infestation by treating the animal with a composition that includes a compound that reduces the protease activity of fleas feeding (includes fleas in the process of feeding as well as fleas having fed) from the treated animal thereby reducing the flea burden on the animal and in the environment of the animal. It is to be noted that the term "a" or "an" entity refers to one or more of that entity; for example, a compound refers to one or more compounds. As such, the terms "a" (or "an"), "one or more" and "at least one" can be used interchangeably herein. Thus, a composition of the present invention can include one or more compounds that target (reduced the activity of) one or more proteases in the flea.

As used herein, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment surrounding the animal (i.e., in the environment of the animal). Such an environment can include not only adult fleas, but also flea eggs and/or flea larvae. The environment can be of any size such that fleas in the environment are able to jump onto and off of a host animal. As such, it is desirable not only to reduce the flea burden on an animal per se, but also to reduce the flea burden in the environment surrounding the animal.

In accordance with the present invention, a host animal is treated by administering to the animal a compound of the present invention in such a manner that the compound itself (e.g., a protease inhibitor, protease synthesis suppressor or anti-flea protease antibody) or a product generated by the animal in response to administration of the compound (e.g., antibodies produced in response to a flea protease vaccine, or conversion of an inactive inhibitor "prodrug" to an active protease inhibitor) ultimately enters the flea midgut. An animal is preferably treated in such a way that the compound or product thereof enters the blood stream of the animal. Fleas are then exposed to the compound when they feed from the animal. For example, flea protease inhibitors administered to an animal are administered in such a way that the inhibitors enter the blood stream of the animal, where they can be taken up by feeding fleas. In another embodiment, when a host animal is administered a flea protease vaccine, the treated animal mounts an immune response resulting in the production of antibodies against the protease (anti-flea protease antibodies) which circulate in the animal's blood stream and are taken up by fleas upon feeding. Blood taken up by fleas enters the flea midgut where compounds of the present invention, or products thereof, such as anti-flea protease antibodies, flea protease inhibitors, and/or protease synthesis suppressors, interact with, and reduce proteolytic activity in the flea midgut. The present invention also includes the ability to reduce larval flea infestation in that when fleas feed from a host animal that has been administered a therapeutic composition of the present invention, at least a portion of compounds of the present invention, or products thereof, in the blood taken up by the flea are excreted by the flea in feces, which is subsequently ingested by flea larvae. It is of note that flea larvae obtain most, if not all, of their nutrition from flea feces.

In accordance with the present invention, reducing proteolytic activity in flea midguts can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

One embodiment of the present invention is a composition that includes one or more compounds that reduce the activity of one or more flea proteases directly (e.g., an anti-flea protease antibody or a flea protease inhibitor) and/or indirectly (e.g., a flea protease vaccine). Suitable flea proteases to target include flea aminopeptidases, flea carboxypeptidases and/or flea endopeptidases. Such proteases can include cytosolic and/or membrane-bound forms of a protease. Preferred flea proteases to target include, but are not limited to, serine proteases, metalloproteases, aspartic acid proteases and/or cysteine proteases. It is to be noted that these preferred groups of proteases include aminopeptidases, carboxypeptidases and/or endopeptidases. Preferred flea proteases to target include, but are not limited to, proteases that degrade hemoglobin, proteases involved in blood coagulation and/or lytic (anti-coagulation) pathways, proteases involved in the maturation of peptide hormones, proteases that inhibit complement or other host immune response elements (e.g., antibodies) and/or proteases involved in vitellogenesis. A number of proteases are known to those skilled in the art, including, but not limited to, aminopeptidases, such as leucine aminopeptidase and aminopeptidases B and M; astacin-like metalloproteases; calpains; carboxypeptidases, such as carboxypeptidases A, P and Y; cathepsins, such as cathepsins B, D, E, G, H, and L, chymotrypsins; cruzipains; meprins; papains; pepsins; renins; thermolysins and trypsins. A particularly preferred protease to target is a protease having a proteolytic activity that, when targeted with a composition of the present invention, reduces flea burden without substantially harming the host animal. Such a protease can be identified using, for example, methods as disclosed herein.

One aspect of the present invention is the discovery that a substantial amount of the proteolytic activity found in flea midguts is serine protease activity. Both in vitro and in vivo studies using a number of protease inhibitors substantiate this discovery, details of which are disclosed in the Examples. As such a particularly preferred protease to target is a serine protease. Examples of serine proteases, include, but are not limited to, acrosins, bromelains, cathepsin G, chymotrypsins, collagenases, elastases, factor Xa, ficins, kallikreins, papains, plasmins, Staphylococcal V8 proteases, thrombins and trypsins. In one embodiment, a preferred flea serine protease to target includes a protease having trypsin-like or chymotrypsin-like activity. It is appreciated by those skilled in the art that an enzyme having "like" proteolytic activity has similar activity to the referenced protease, although the exact structure of the preferred substrate cleaved may differ. "Like" proteases usually have similar tertiary structures as their referenced counterparts.

Protease inhibitor studies disclosed in the Examples section also indicate that additional preferred proteases to target include aminopeptidases and/or metalloproteases. Examples of such proteases include exo- and endo-metalloproteases, digestive enzymes, and enzymes involved in peptide hormone maturation. One example of an aminopeptidase that is also a metalloprotease is leucine aminopeptidase.

Suitable compounds to include in compositions of the present invention include, but are not limited to, a vaccine comprising a flea protease (a flea protease vaccine), an antibody that selectively binds to a flea protease (an anti-flea protease antibody), a flea protease inhibitor (a compound other than a vaccine or an antibody that inhibits a flea protease), and a mixture of such compounds. As used herein, a mixture thereof refers to a combination of one or more of the cited entities. Compositions of the present invention can also include compounds to suppress protease synthesis or maturation, such as, but not limited to, protease modulating peptides.

A preferred embodiment of the present invention is a flea protease vaccine and its use to reduce the flea population on and around an animal. A flea protease vaccine can include one or more proteins capable of eliciting an immune response against a flea protease and can also include other components. Preferred flea protease vaccines include a flea serine protease, a flea metalloprotease, a flea aspartic acid protease and/or a flea cysteine protease, with flea serine protease, flea metalloprotease and/or flea aminopeptidase vaccines being more preferred. Examples of flea protease vaccines include soluble flea midgut preparations of the present invention as well as one or more isolated proteins of the present invention.

One embodiment of the present invention is a soluble flea midgut preparation. Such a preparation includes primarily components naturally present in the lumen of a flea midgut and, depending on the method of preparation, can also include one or more peripheral midgut membrane proteins. Methods to preferentially include, or exclude, membrane proteins from such a preparation are known to those skilled in the art. The present invention includes the discovery that such a preparation has proteolytic activity, of which a substantial portion is serine protease activity. Preferably at least about 70 percent of the proteolytic activity in a soluble flea midgut soluble preparation is serine protease activity, as can be indicated by the ability to inhibit at least about 70 percent of the proteolytic activity with 4-2-aminoethylbenzenesulfonylfluoride-hydrochloride (AEBSF). Serine protease activity can also be identified using other known inhibitors or substrates. Other preferred inhibitors that can inhibit at least about 70 percent of the proteolytic activity of a soluble flea midgut preparation of the present invention include soybean trypsin inhibitor, 1,3-diisopropylfluorophosphate or leupeptin.

A soluble flea midgut preparation of the present invention includes proteases that range in molecular weight from about 5 kilodaltons (kD or kDa) to about 200 kD, as determined by SDS-PAGE (sodium dodecyl sulfate polyacrylamide gel electrophoresis), with at least a substantial portion of the serine proteases ranging in molecular weight from about 5 kD to about 60 kD, as determined by SDS-PAGE. A substantial portion of protease activity in a soluble flea midgut preparation of the present invention has a pH activity optimum ranging from about pH 5 to about pH 10, preferably an activity optimum ranging from about pH 7 to about pH 9, and even more preferably an activity optimum of about pH 8. While not being bound by theory, such a pH optimum suggests that a large proportion of proteases in soluble flea midgut preparations of the present invention are serine proteases. It is also interesting to note that the pH of the flea midgut is also about pH 8. The findings that proteases in soluble flea midgut preparations of the present invention exhibit a varied pattern of inhibition by protease inhibitors of a given type (e.g., serine protease inhibitors), as well as variances seen in molecular weights and pH optima of the proteases, suggest that there are a number of protease isoforms in such preparations.

A soluble flea midgut preparation of the present invention is preferably prepared by a method that includes the steps of (a) disrupting a flea midgut to produce a mixture including a liquid portion and a solid portion and (b) recovering the liquid portion to obtain a soluble flea midgut preparation. Such a method is a simplified version of methods disclosed in U.S. Pat. No. 5,356,622, ibid. It is to be noted that in accordance with the present invention, methods disclosed in U.S. Pat. No. 5,356,622, ibid. can also be used to prepare soluble flea midgut preparations having similar proteolytic activities.

Flea midguts can be obtained (e.g., dissected from) from unfed fleas or from fleas that recently consumed a blood meal (i.e., blood-fed fleas). Such midguts are referred to herein as, respectively, unfed flea midguts and fed flea midguts. Flea midguts can be obtained from either male or female fleas. As demonstrated in the Examples section, female flea midguts exhibit somewhat more proteolytic activity than do male flea midguts. Furthermore, fed flea midguts have significantly more proteolytic activity than do unfed flea midguts. While not being bound by theory, it is believed that blood feeding induces in flea midguts the synthesis and/or activation of proteases as well as other factors (e.g., enzymes, other proteins, co-factors, etc.) important in digesting the blood meal, as well as in neutralizing host molecules potentially damaging to the flea (e.g., complement, immunoglobulins, blood coagulation factors). It is also to be appreciated that unfed flea midguts may contain significant targets not found in fed flea midguts and vice versa. Furthermore, although the present application focuses primarily on flea midgut proteases, it is to be noted that the present invention also includes other components of soluble flea midgut preparations of the present invention that provide suitable targets to reduce flea burden on an animal and in the environment of that animal; see also U.S. Pat. No. 5,356,622, ibid.

Methods to disrupt flea midguts in order to obtain a soluble flea midgut preparation are known to those skilled in the art and can be selected according to, for example, the volume being processed and the buffers being used. Such methods include any technique that promotes cell lysis, such as, but are not limited to, chemical disruption techniques (e.g., exposure of midguts to a detergent) as well as mechanical disruption techniques (e.g., homogenization, sonication, use of a tissue blender or glass beads, and freeze/thaw techniques).

Methods to recover a soluble flea midgut preparation are also known to those skilled in the art and can include any method by which the liquid portion of disrupted flea midguts is separated from the solid portion (e.g., filtration or centrifugation). In a preferred embodiment, disrupted flea midguts are subjected to centrifugation, preferably at an acceleration ranging from about 10,000×g to about 15,000×g for several minutes (e.g., from about 1 min. to about 15 min.). The supernatant from such a centrifugation comprises a soluble flea midgut preparation of the present invention.

The present invention also includes an isolated protein that includes an amino acid sequence encoded by a nucleic acid molecule capable of hybridizing under stringent conditions (i.e., that hybridize under stringent hybridization conditions) with a nucleic acid molecule that encodes a protease present (i.e., the nucleic acid molecules hybridize with the nucleic acid strand that is complementary to the coding strand) in (i.e., can be found in) a flea midgut, such as a midgut from a blood-fed female flea, a midgut from a blood-fed male flea, a midgut from an unfed female flea or a midgut from an unfed male flea. A preferred midgut protease is present in the lumen of the midgut.

An isolated protein of the present invention, also referred to herein as an isolated protease protein, preferably is capable of eliciting an immune response against a flea midgut protease and/or has proteolytic activity. According to the present invention, an isolated, or biologically pure, protein, is a protein that has been removed from its natural milieu. As such, "isolated" and "biologically pure" do not necessarily reflect the extent to which the protein has been purified. An isolated protease protein can be obtained from its natural source. Such an isolated protein can also be produced using recombinant DNA technology or chemical synthesis.

As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue comprises a protein having an amino acid sequence that is sufficiently similar to a natural flea midgut protease that a nucleic acid sequence encoding the homologue is capable of hybridizing under stringent conditions to (i.e., with) the complement of a nucleic acid sequence encoding the corresponding natural flea midgut protease amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Protease protein homologues of the present invention preferably have protease activity and/or are capable of eliciting an immune response against a flea midgut protease.

A protease protein homologue of the present invention can be the result of allelic variation of a natural gene encoding a flea protease. A natural gene refers to the form of the gene found most often in nature. Protease protein homologues can be produced using techniques known in the art including, but not limited to, direct modifications to a gene encoding a protein using, for example, classic or recombinant DNA techniques to effect random or targeted mutagenesis. Isolated protease proteins of the present invention, including homologues, can be identified in a straightforward manner by the proteins' ability to effect proteolytic activity and/or to elicit an immune response against a flea midgut protease. Such techniques are known to those skilled in the art.

A preferred protease protein of the present invention is a flea serine protease, a flea metalloprotease, a flea aspartic acid protease, a flea cysteine protease, or a homologue of any of these proteases. A more preferred protease protein is a flea serine protease, a flea metalloprotease or a homologue of either. Also preferred is a flea aminopeptidase or a homologue thereof. Also preferred is a flea cysteine protease or a homologue thereof. Particularly preferred is a flea serine protease or a homologue thereof.

Preferred protease proteins of the present invention are flea protease proteins having molecular weights ranging from about 5 kD to about 200 kD, as determined by SDS-PAGE, and homologues of such proteins. More preferred are flea protease proteins having molecular weights ranging from about 5 kD to about 60 kD, as determined by SDS-PAGE, and homologues of such proteins. Even more preferred are flea serine protease proteins, particularly those having molecular weights of about 26 kD (denoted PfSP26, now denoted PafSP-26K to distinguish from flea PfSP26 as described in Example 26), about 24 kD (denoted PfSP24, now denoted PafSP-24K to distinguish from flea PfSP24 as described in Example 27), about 19 kD (denoted PfSP19, now denoted PafSP-19K to distinguish from flea PfSP19 as described in Example 32), about 6 kD (denoted PfSP6, now denoted PafSP-6K to distinguish from flea PfSP6 as described in Example 11), about 31 kD (denoted PfSP28), about 25 kD (denoted PlfSP-25K1) from 1st instar larvae, about 25 kD (denoted PlfSP-25K3) from 3rd instar larvae, about 28 kD (denoted PlfSP-28K3) and about 31 kD (denoted PlfSP-31K3), and flea aminopeptidase proteins, particularly those having molecular weights of about 95 kD (denoted PfAP-95K) as determined by SDS-PAGE, and homologues of such proteins.

One preferred embodiment of the present invention is an isolated flea protease protein that includes an amino acid sequence encoded by a nucleic acid molecule that hybridizes under stringent hybridization conditions with a flea serine protease gene, with a flea aminopeptidase gene or with a flea cysteine protease gene. As used herein, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself.

The inventors have discovered an extensive family of serine proteases, encoded by a family of serine protease genes. Such a gene family may be due to allelic variants (i.e., genes having similar, but different, sequences at a given locus in a population of fleas) and/or to, the existence of serine protease genes at more than one locus in the flea genome. As such, the present invention includes flea serine protease genes comprising not only the nucleic acid sequences disclosed herein (e.g., genes including nucleic acid sequences SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43, SEQ ID NO:45, and/or nucleic acid sequences encoding proteins having amino acid sequences as disclosed herein (e.g., SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73 and/or SEQ ID NO:96, but also allelic variants of any of those nucleic acid sequences, as well as other nucleic acid molecules and amino acid sequences disclosed in the examples section. (It should be noted that since nucleic acid sequencing technology is not entirely error-free, all sequences represented herein are at best apparent (i.e., deduced) nucleic acid or amino acid sequences.)

A preferred flea cysteine protease gene includes nucleic acid sequence SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94, which encode a cysteine protease protein including SEQ ID NO:2, SEQ ID NO:5, SEQ ID NO:8, SEQ ID NO:89, SEQ ID NO:92 or SEQ ID NO:95. Additional preferred cysteine protease genes include allelic variants of SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94.

A preferred flea serine protease protein of the present invention is encoded by a nucleic acid molecule that hybridizes under stringent hybridization conditions with at least one of the following nucleic acid molecules: nfSP18, nfSP24, nfSP28, nfSP32, nfSP33 and nfSP40. As used herein, each of these nucleic acid molecules represent the entire coding region of a flea serine protease gene of the present invention (at least portions of which are also referred to by flea clone numbers, as described in the Examples). Nucleic acid molecules that contain partial coding regions or other parts of the corresponding gene are denoted by names that include the size of those nucleic acid molecules (e.g., nfSP40$_{428}$). Nucleic acid molecules containing apparent full length coding regions for which the size is known also are denoted by names that include the size of those nucleic acid molecules (e.g., nfSP40$_{841}$). The production, and at least partial nucleic acid sequence, of such nucleic acid molecules is disclosed in the Examples.

Particularly preferred serine protease proteins are encoded by a nucleic acid molecule that hybridizes under stringent hybridization conditions with at least one of the following nucleic acid molecules: nfSP18$_{534}$, nfSP18$_{775}$, nfSP18$_{225}$, nfSP24$_{410}$, nfSP24$_{1089}$, nfSP24$_{774}$, nfSP24$_{711}$, nfSP28$_{923}$, nfSP32$_{933}$, nfSP32$_{933}$, nfSP32$_{924}$, nfSP32$_{699}$, nfSP33$_{3426}$, nfSP33$_{778}$, nfSP33$_{1894}$, nfSP33$_{1200}$, nfSP33$_{726}$, nfSP40$_{841}$ and/or nfSP40$_{717}$. Even more preferred serine protease proteins include the following amino acid sequences: SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:89, SEQ ID NO:92, SEQ ID NO:95 and/or SEQ ID NO:96. Additional particularly preferred serine protease proteins are encoded by allelic variants of nucleic acid molecules encoding proteins that include the cited amino acid sequences. Also preferred are flea serine protease proteins including regions that have at least about 50%, preferably at least about 75%, and more preferably at least about 90% identity with flea serine protease proteins having amino acid sequences as cited herein.

One embodiment of the present invention is a flea serine protease that degrades immunoglobulin circulating in a host animal (i.e., flea immunoglobulin proteinase or IgGase). An example of a flea immunoglobulin proteinase is presented in the Examples section. Preferably, an immunoglobulin proteinase of the present invention cleaves an immunoglobulin when the protein is incubated in the presence of the immunoglobulin in about 100 microliters of about 0.2M Tris-HCl for about 18 hours at about 37° C. Suitable immunoglobulin proteinase proteins of the present invention are capable of cleaving the hinge region of an immunoglobulin heavy chain. The hinge region of an immunoglobulin is the flexible domain that joins the Fab arms of the immunoglobulin to the Fc portion of the molecule. A more preferred immunoglobulin proteinase protein includes a protein having a molecular weight ranging from about 25 kD to about 35 kD and more preferably having a molecular weight of about 31 kD, in its mature form. An even more preferred immunoglobulin proteinase protein includes a protein comprising an amino acid sequence including SEQ ID NO:67, SEQ ID NO:68, SEQ ID NO:69, SEQ ID NO:70, SEQ ID NO:71, SEQ ID NO:72, SEQ ID NO:73 and/or SEQ ID NO:96, which can be encoded by a gene comprising nucleic acid sequence SEQ ID NO:66. Without being bound by theory, the proteinase activity of an immunoglobulin proteinase of the present invention cleaves an immunoglobulin in such a manner that the immunoglobulin maintains intact heavy and light chain pairs, either as two Fab fragments or one F(ab')$_2$ fragment. As used herein, a Fab fragment refers to complete immunoglobulin light chains paired with the variable region and CH1 domains of an immunoglobulin heavy chain. As used herein, a F(ab')$_2$ fragment refers to two Fab fragments that remain linked by a disulfide bond. Both Fab and F(ab')$_2$ fragments are capable of binding antigen.

A preferred flea cysteine protease protein of the present invention is encoded by a nucleic acid molecule that hybridizes under stringent hybridization conditions with nucleic acid molecule nfCP1 (a flea cysteine protease full-length coding region that includes nfCP1$_{573}$ or nfCP1$_{1109}$ (the production of which are described in the Examples). Even more preferred is a cysteine protease that includes amino acid sequence SEQ ID NO:2, SEQ ID NO:5, SEQ ID NO:8, SEQ ID NO:89, SEQ ID NO:92, SEQ ID NO:95, or a cysteine protease encoded by an allelic variant of a nucleic acid molecule that includes SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 or SEQ ID NO:94. Also preferred is a flea cysteine protease protein including regions that have at least about 50%, preferably at least about 75%, and more preferably at least about 90% identity with SEQ ID NO:2, SEQ ID NO:5, SEQ ID NO:8, SEQ ID NO:89, SEQ ID NO:92 or SEQ ID NO:95.

One embodiment of the present invention is an isolated protein having proteolytic activity that is substantially inhibited by a serine protease inhibitor, an aminopeptidase inhibitor and/or a cysteine protease inhibitor. Such inhibition can be measured by techniques known to those skilled in the art. To be substantially inhibited means, for example, for a serine protease, that at least half of the proteolytic activity of the protease protein is inhibited by a serine protease inhibitor. Preferably at least about 70 percent, and even more preferably at least about 90 percent of the proteolytic activity of the protease protein is inhibited by a serine protease inhibitor. Preferred serine protease inhibitors include flea serpin proteins, and peptides or analogs thereof.

An isolated protein of the present invention can be produced in a variety of ways, including recovering such a protein from a flea midgut and producing such a protein recombinantly. In one embodiment, a flea midgut protease can be recovered by methods heretofore disclosed for obtaining a soluble flea midgut preparation. A flea midgut protease protein can be further purified from a disrupted flea midgut by a number of techniques known to those skilled in the art, including, but not limited to, affinity chromatography, ion exchange chromatography, filtration, electrophoresis (e.g., standard, capillary and flow-through electrophoresis), hydrophobic interaction chromatography, gel filtration chromatography, reverse phase chromatography, concanavalin A chromatography, chromatofocusing and differential solubilization. In one embodiment, a flea midgut protease is purified using protease inhibitor affinity chromatography, an example of which is disclosed in the Examples section.

Another embodiment of the present invention is a method to produce an isolated protein of the present invention using recombinant DNA technology. Such a method includes the steps of (a) culturing a recombinant cell comprising a nucleic acid molecule encoding a protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques, as heretofore disclosed.

Isolated proteins of the present invention are preferably retrieved in "substantially pure" form. As used herein, "substantially pure" refers to a purity that allows for the effective use of the protein as a vaccine. A vaccine for animals, for example, should exhibit no substantial toxicity and should be capable of stimulating the production of antibodies in a vaccinated animal.

Another embodiment of the present invention is an isolated nucleic acid molecule capable of hybridizing under stringent conditions with a gene encoding a flea protease present in a flea midgut. Such a nucleic acid molecule is also referred to herein as a flea protease nucleic acid molecule. Particularly preferred is an isolated nucleic acid molecule that hybridizes under stringent conditions with a flea serine protease gene, with a flea aminopeptidase gene or with a flea cysteine protease gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself. A nucleic acid molecule of the present invention can be an isolated natural flea protease nucleic acid molecule or a homologue thereof. A nucleic acid molecule of the present invention can include one or more regulatory regions, full-length or partial coding regions, or combinations thereof. The minimal size of a flea protease nucleic acid molecule of the present invention is the minimal size capable of forming a stable hybrid under stringent hybridization conditions with a corresponding natural gene. Flea protease nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated flea protease nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a flea protease protein of the present invention or to form stable hybrids under stringent conditions with natural nucleic acid molecule isolates.

A flea protease nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against a flea protease and/or to have proteolytic activity) and/or by hybridization with isolated flea protease nucleic acids under stringent conditions.

An isolated flea protease nucleic acid molecule of the present invention can include a nucleic acid sequence that encodes at least one flea protease protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an flea protease protein.

One embodiment of the present invention is a flea protease nucleic acid molecule of the present invention that is capable of hybridizing under stringent conditions to a nucleic acid strand that encodes at least a portion of a flea protease or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Preferred is a flea protease nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea protease protein. Particularly preferred is a flea protease nucleic acid molecule capable of encoding at least a portion of a flea protease that naturally is present in flea midguts and preferably is included in a soluble flea midgut preparation of the present invention. Examples of nucleic acid molecules of the present invention are disclosed in the Examples section.

A preferred flea serine protease nucleic acid molecule of the present invention is a nucleic acid molecule that hybridizes under stringent hybridization conditions with at least one of the following nucleic acid molecules: nfSP18, nfSP24, nfSP28, nfSP32, nfSP33 and/or nfSP40. More preferred is a nucleic acid molecule that hybridizes under stringent hybridization conditions with at least one of the following nucleic acid molecules: nfSP18$_{534}$, nfSP18$_{775}$, nfSP18$_{225}$, nfSP24$_{410}$, nfSP24$_{1089}$, nfSP24$_{774}$, nfSP24$_{711}$, nfSP28$_{711}$, nfSP28$_{923}$, nfSP32$_{933}$, nfSP32$_{933}$, nfSP32$_{699}$, nfSP33$_{426}$, nfSP33$_{778}$, nfSP33$_{1894}$, nfSP33$_{1200}$, nfSP33$_{726}$, nfSP40$_{841}$ and/or nfSP40$_{717}$, as well as other specific nucleic acid molecules disclosed in the Examples section. Even more preferred are nucleic acid molecules that include nfSP18, nfSP24, nfSP28, nfSP32, nfSP33 and/or nfSP40 and even more nfSP18$_{534}$, nfSP18$_{775}$, nfSP18$_{225}$, nfSP24$_{410}$, nfSP24$_{1089}$, nfSP24$_{774}$, nfSP24$_{711}$, nfSP28$_{923}$, nfSP32$_{933}$, nfSP32$_{933}$, nfSP32$_{924}$, nfSP32$_{699}$, nfSP33$_{426}$, nfSP33$_{778}$, nfSP33$_{1894}$, nfSP33$_{1200}$, nfSP33$_{726}$, nfSP40$_{841}$ and/or nfSP40$_{717}$, as well as other specific nucleic acid molecules disclosed in the Examples section.

Particularly preferred flea serine protease nucleic acid molecules include at least one of the following sequences:SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43 and/or SEQ ID NO:45, and complements thereof, as well as other specific nucleic acid molecules disclosed in the Examples section. Also preferred are allelic variants of such nucleic acid molecules.

A preferred flea cysteine protease nucleic acid molecule of the present invention is a nucleic acid molecule that hybridizes under stringent hybridization conditions with nfCP1$_{573}$, or nfCP1$_{1109}$ (the production of which are described in the Examples). More preferred is a cysteine protease nucleic acid molecule that includes nfCP1$_{573}$ or nfCP1$_{1109}$. Particularly preferred is a nucleic acid molecule that includes nucleic acid sequence SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94, or allelic variants of such nucleic acid molecules.

Knowing a nucleic acid molecule of a flea protease protein of the present invention allows one skilled in the art to make copies of that nucleic acid molecule as well as to obtain a nucleic acid molecule including additional portions of flea protease protein-encoding genes (e.g., nucleic acid molecules that include the translation start site and/or transcription and/or translation control regions), and/or flea protease nucleic acid molecule homologues. Knowing a portion of an amino acid sequence of a flea protease protein of the present invention allows one skilled in the art to clone nucleic acid sequences encoding such a flea protease protein. In addition, a desired flea protease nucleic acid molecule can be obtained in a variety of ways including screening appropriate expression libraries with antibodies which bind to flea protease proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea protease nucleic acid molecules, preferred cDNA libraries include cDNA libraries made from unfed whole fleas, fed whole fleas, fed flea midguts, unfed flea midguts, and flea salivary glands. Techniques to clone and amplify genes are disclosed, for example, in Sambrook et al., ibid. The Examples section includes examples of the isolation of cDNA sequences encoding flea protease proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea protease protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit flea protease production. Such therapeutic applications include the use of such oligonucleotides in, for example, antisense-, triplex formation-, ribozyme- and/or RNA drug-based technologies. The present invention, therefore, includes such oligonucleotides and methods to interfere with the production of flea protease proteins by use of one or more of such technologies.

The present invention also includes a recombinant vector, which includes a flea protease nucleic acid molecule of the present invention inserted into any vector capable of delivering the nucleic acid molecule into a host cell. Such a vector contains heterologous nucleic acid sequences, that is nucleic acid sequences that are not naturally found adjacent to flea protease nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of flea protease nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a flea protease protein of the present invention by culturing a cell capable of expressing the protein under conditions effective to produce the protein, and recovering the protein. A preferred cell to culture is a recombinant cell that is capable of expressing the flea protease protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced flea protease protein. Such cells are, therefore, capable of producing flea protease proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., E. coli) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda P_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, Heliothis zea insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a flea protease protein.

Expression vectors of the present invention may also contain secretory signals (i.e., signal segment nucleic acid sequences) to enable an expressed flea protease protein to be secreted from the cell that produces the protein. Suitable signal segments include a flea protease protein signal segment or any heterologous signal segment capable of directing the secretion of a flea protease protein, including fusion proteins, of the present invention. Preferred signal segments include, but are not limited to, flea protease, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a flea protease nucleic acid molecule of the present invention can enhance the stability during production, storage and/or use of the protein encoded by the nucleic acid molecule. Furthermore, a fusion segment can function as a tool to simplify purification of a flea protease protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a flea protease protein. Linkages between fusion segments and flea protease proteins can be constructed to be susceptible to cleavage to enable straightforward recovery of the flea protease proteins. Fusion proteins are preferably produced by culturing a recombinant cell transformed with a fusion nucleic acid sequence that encodes a protein including the fusion segment attached to either the carboxyl and/or amino terminal end of a flea protease protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules of the present invention, with those that encode one or more flea protease proteins, and particularly one or more flea serine protease, aminopeptidase and/or cysteine protease proteins, being more preferred. Similarly, a preferred recombinant cell includes one or more nucleic acid molecules of the present invention, with those that encode one or more flea protease proteins, and particularly one or more flea serine protease, aminopeptidase, and/or cysteine protease proteins, being more preferred.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce flea protease proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a flea protease protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant flea protease proteins may either remain within the recombinant cell; be secreted into the fermentation medium; be secreted into a space between two cellular membranes, such as the periplasmic space in *E. coli;* or be retained on the outer surface of a cell or viral membrane. Methods to purify such proteins are heretofore disclosed.

The present invention also includes isolated anti-flea protease antibodies and their use to reduce flea infestation on a host animal as well as in the environment of the animal. An anti-flea protease antibody is an antibody capable of selectively binding to a protease present in a flea midgut, including female and male fed midguts as well as female and male unfed midguts. An anti-flea protease antibody preferably binds to the protease in such a way as to reduce the proteolytic activity of that protease.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protease against which the antibody was raised (i.e., to be able to distinguish that protease from unrelated components in a mixture.). Binding affinities typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a flea protease nucleic acid molecule of the present invention.

Anti-flea antibodies of the present invention include antibodies raised in an animal administered a flea protease vaccine of the present invention that exert their effect when fleas feed from the vaccinated animal's blood containing such antibodies. Anti-flea antibodies of the present invention also include antibodies raised in an animal against one or more flea protease proteins, or soluble flea midgut preparations, of the present invention that are then recovered from the animal using techniques known to those skilled in the art. Yet additional antibodies of the present invention are produced recombinantly using techniques as heretofore disclosed for flea protease proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-flea protease antibodies of the present invention have a variety of uses that are within the scope of the present invention. For example, such antibodies can be used in a composition of the present invention to passively immunize an animal in order to protect the animal from flea infestation. Anti-flea antibodies can also be used as tools to screen expression libraries and/or to recover desired proteins of the present invention from a mixture of proteins and other contaminants. Furthermore, antibodies of the present invention can be used to target cytotoxic agents to fleas in order to kill fleas. Targeting can be accomplished by conjugating (i.e., stably joining) such antibodies to the cytotoxic agents using techniques known to those skilled in the art.

A preferred anti-flea protease antibody of the present invention can selectively bind to, and preferentially reduce the proteolytic activity of, a flea serine protease, a flea metalloprotease, a flea aspartic acid protease and/or a flea cysteine protease. More preferred anti-flea protease antibodies include anti-flea serine protease antibodies, anti-flea metalloprotease antibodies, anti-flea aminopeptidase antibodies, and anti-flea cysteine protease antibodies. Particularly preferred are anti-flea serine protease antibodies, anti-flea aminopeptidase antibodies, and anti-flea cysteine protease antibodies, including those raised against flea serine protease proteins, flea aminopeptidase proteins or cysteine protease proteins of the present invention.

The present invention also includes the use of protease inhibitors that reduce proteolytic activity of flea proteases to reduce flea infestation of animals and the surrounding environment. As used herein, protease inhibitors are compounds that interact directly with a protease thereby inhibiting that protease's activity, usually by binding to or otherwise interacting with the protease's active site. Protease inhibitors are usually relatively small compounds and as such differ from anti-protease antibodies that interact with the active site of a protease.

Protease inhibitors can be used directly as compounds in compositions of the present invention to treat animals as long as such compounds are not harmful to the animals being treated. Protease inhibitors can also be used to identify preferred types of flea proteases to target using compositions of the present invention. For example, the inventors have shown herein the predominance of serine proteases in flea midguts, particularly in soluble flea midgut preparations, using protease inhibitors. Such knowledge suggests that effective reduction of flea infestation of an animal can be achieved using serine protease vaccines, anti-flea serine protease antibodies and other inhibitors of serine protease synthesis and activity that can be tolerated by the animal. For example, flea immunoglobulin proteinase activity disclosed herein can be targeted to reduce flea infestation. That other proteases are also present in flea midguts according to the present invention also suggests targeting such proteases. Methods to use protease inhibitors are known to those skilled in the art; examples of such methods are disclosed herein.

In one embodiment, a protease inhibitor that can be used in a composition of the present invention to treat an animal is identified by a method including the following steps: (a) identifying candidate (i.e., putative, possible) inhibitor compounds by testing the efficacy of one or more protease inhibitors (i) in vitro for their ability to inhibit flea protease activity and/or (ii) in a flea feeding assay for their ability to reduce the survival and/or fecundity of fleas by adding the inhibitors to the blood meal of a flea being maintained, for example, in a feeding system, such as that described by Wade et al., 1988, *J.Med Entomol.* 25, 186–190; and (b) testing the efficacy of the candidate inhibitor compounds in animals infested with fleas. Although one does not need both in vitro assay data and flea feeding assay data to determine which candidate compounds to administer to animals, evaluation of both sets of data is preferred since data from neither of the assays necessarily predicts data to be obtained from the other assay. For example, candidate compounds identified using the in vitro assay may work "in the test tube" but may not work in vivo for a number of reasons, including the presence of interfering components in the blood meal that inhibit the activity of such compounds; e.g., although aprotinin can inhibit at least some flea serine proteases in vitro, aprotinin does not work well in the presence of serum proteins, such as are found in the blood. Furthermore, candidate inhibitor compounds identified by the flea feeding assays can include not only desired compounds but also compounds that reduce the viability and/or fecundity of fleas due to general toxicity (e.g., affecting the mitochondria of fleas).

In a preferred embodiment, an inhibitor of a flea protease of the present invention is identified by a method comprising: (a) contacting an isolated flea protease protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95 with a putative inhibitory compound under conditions in which, in the absence of the compound, the protein has proteolytic activity; and (b) determining if the putative inhibitory compound inhibits the activity. A test kit can be used to perform such method. A preferred test kit comprises an isolated flea protease protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95, and a means for determining the extent of inhibition of the activity in the presence of a putative inhibitory compound.

In another embodiment, protease inhibitors are used in the purification of corresponding proteases by, for example, affinity chromatography, in which, a protease inhibitor is incubated with a mixture containing a desired protease under conditions that the inhibitor forms a complex with the protease. The protease can then be recovered from the complex. The protease inhibitor can be attached to a solid support and/or be labelled with, for example, a radioactive, fluorescent, or enzymatic tag that can be used to detect and/or recover the complex.

Suitable protease inhibitors to use in accordance with the present invention include serine protease inhibitors (including immunoglobulin proteinase inhibitors and serpins), metalloprotease inhibitors, aspartic acid protease inhibitors, cysteine protease inhibitors and aminopeptidase inhibitors. Preferred protease inhibitors include serine protease inhibitors, metalloprotease inhibitors, aminopeptidase inhibitors and cysteine protease inhibitors, particularly those that are broad spectrum inhibitors. More preferred are broad spectrum serine protease inhibitors.

There is a wide variety of protease inhibitors, as is known to one skilled in the art. Examples include, but are not limited to, AEBSF, aprotinin, bestatin, chloromethyl ketones TLCK (Nα-p-tosyl-L-lysine chloromethyl ketone) and TPCK (N-tosyl-L-phenylalanine chloromethyl ketone), chymostatin, cystatin, 3'4-dichloroisocoumarin, E-64 (transepoxysuccinyl-L-leucylamido-(4-guanidino)butane), EDTA (ethylenediaminetetraacetic acid), leupeptin, methyl ketones having a variety of leaving groups, oxidized L-leucinethiol, pepstatin, 1,10-orthophenanthroline, phosphoramidon, soybean trypsin/chymotrypsin inhibitor and soybean trypsin inhibitor. Preferred protease inhibitors for use in the present invention include AEBSF, bestatin, E-64 leupeptin, pepstatin, 1,10-orthophenanthroline, phosphoramidon, TLCK and TPCK, with AEBSF (a broad spectrum serine protease inhibitor), bestatin (an inhibitor of leucine aminopeptidase) and 1,10-orthophenanthroline (a broad spectrum metalloprotease inhibitor) being particularly preferred.

Protease inhibitors can be produced using methods known to those skilled in the art. Protein- or peptide-based protease inhibitors, such as cystatin or small peptides comprising a protease substrate, can be produced recombinantly and modified as necessary.

The present invention also includes the use of proteolytically active flea protease proteins of the present invention to identify additional protease inhibitors, and preferably protease inhibitor compounds that can be included in a composition of the present invention to be administered to animals. A method to identify a flea protease inhibitor includes the steps of (a) contacting (e.g., combining, mixing) an isolated flea protease protein with a putative (i.e., candidate) inhibitory compound under conditions in which, in the absence of the compound, the protein has proteolytic activity, and (b) determining if the putative inhibitory compound inhibits the proteolytic activity of the protein. Putative inhibitory compounds to screen include organic molecules, antibodies (including functional equivalents thereof) and substrate analogs. Methods to determine protease activity are known to those skilled in the art, as heretofore disclosed. Particularly preferred for use in identifying inhibitors are flea serine protease proteins, flea aminopeptidase proteins and flea cysteine protease proteins of the present invention.

The present invention also includes inhibitors isolated by such a method, and/or test kit, and their use to inhibit any flea protease that is susceptible to such an inhibitor.

It is to be appreciated that the present invention also includes mimetopes of compounds of the present invention that can be used in accordance with methods as disclosed for compounds of the present invention. As used herein, a mimetope of a proteinaceous compound of the present invention (e.g., a flea protease protein, an anti-flea protease antibody, a proteinaceous inhibitor of protease activity or synthesis) refers to any compound that is able to mimic the activity of that proteinaceous compound, often because the mimetope has a structure that mimics the proteinaceous compound. For example, a mimetope of a flea protease protein is a compound that has an activity similar to that of an isolated flea protease protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

The present invention includes therapeutic compositions, also referred to herein as compositions, that include a (i.e., at least one) compound of the present invention. Preferred compounds to include in a composition of the present invention include flea protease vaccines, anti-flea protease antibodies and/or protease inhibitors as disclosed herein. Such a therapeutic composition can protect an animal from flea infestation by reducing flea protease activity, thereby reducing flea burden on the animal and in the environment of the animal.

Particularly preferred therapeutic compositions of the present invention include at least one of the following compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein; an inhibitor of flea serine protease activity identified by its ability to inhibit flea serine protease activity; an isolated flea cysteine protease protein or a mimetope thereof; an isolated flea cysteine protease nucleic acid molecule that hybridizes under stringent hybridization conditions with a flea cysteine protease gene; an isolated antibody that selectively binds to a flea cysteine protease protein; and an inhibitor of flea cysteine protease activity identified by its ability to inhibit flea cysteine protease activity.

Another embodiment of the present invention is a therapeutic composition that includes a first compound that reduces flea protease activity and a second compound that reduces flea burden by a method other than by reducing flea protease activity. The present invention also includes a method to protect an animal from flea infestation by administering to the animal such a composition. The first compound of such a composition by effectively reducing flea protease activity in the midgut, enhances the activity of the second compound. While not being bound by theory, it is believed that a number of anti-flea treatments, particularly those that are proteinaceous, are not very effective because they are degraded in the flea midgut. The present invention permits the effective use of such anti-flea treatments by reducing proteolytic degradation of such treatments by the flea midgut.

Preferred first compounds to include in such a composition include flea protease vaccines, anti-flea protease antibodies and/or protease inhibitors as disclosed herein, such compounds that target flea immunoglobulin proteinase activity.

A preferred therapeutic composition of the present invention comprises an excipient and a protective compound including: an isolated protein or mimetope thereof encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95; an isolated nucleic acid molecule that hybridizes under stringent hybridization conditions with a gene comprising a nucleic acid sequence including SEQ ID NO:9, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:39, SEQ ID NO:40, SEQ ID NO:42, SEQ ID NO:43, SEQ ID NO:45, SEQ ID NO:1, SEQ ID NO:3, SEQ ID NO:4, SEQ ID NO:6, SEQ ID NO:7, SEQ ID NO:88, SEQ ID NO:90, SEQ ID NO:91, SEQ ID NO:93 and/or SEQ ID NO:94; an isolated antibody that selectively binds to a protein encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95; an inhibitor of protease activity identified by its ability to inhibit the activity of a protein encoded by a nucleic acid molecule that hybridizes under stringent hybridization conditions with a nucleic acid molecule having a nucleic acid sequence encoding a protein comprising an amino acid sequence including SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:33, SEQ ID NO:36, SEQ ID NO:38, SEQ ID NO:41, SEQ ID NO:44, SEQ ID NO:67, SEQ ID NO:68, SEQ ID NO:69, SEQ ID NO:70, SEQ ID NO:71, SEQ ID NO:72, SEQ ID NO:73, SEQ ID NO:96, SEQ ID NO:2, SEQ ID NO:5, SEQ ID NO:8, SEQ ID NO:89, SEQ ID NO:92 and/or SEQ ID NO:95; and a mixture thereof.

Suitable second compounds include any anti-flea agent(s), including, but not limited to, proteinaceous compounds, insecticides and flea collars. Preferred second compounds are proteinaceous compounds that effect active immunization (e.g., antigen vaccines), passive immunization (e.g., antibodies), or that otherwise inhibit a flea activity that when inhibited can reduce flea burden on and around an animal. Examples of second compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system and/or a compound that inhibits flea feeding.

Compositions of the present invention can also include other components such as a pharmaceutically acceptable excipient, an adjuvant, and/or a carrier. For example, compositions of the present invention can be formulated in an excipient that the animal to be treated can tolerate.

Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to reduce protease activity in fleas feeding from the animal over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from flea infestation, a therapeutic composition of the present invention is administered to the animal in an effective manner such that the protease activity of fleas feeding from the blood stream of animals treated with the composition is reduced. As such, a treated animal is an animal that is competent to reduce the flea burden by reducing flea protease activity, or by reducing flea protease activity and at least one other flea activity. Preferably, the protease activity is reduced by at least about 50 percent, more preferably by at least about 70 percent and even more preferably by at least about 90 percent. Methods to administer compositions to the animal in order to render the animal competent depend on the nature of the composition and administration regime. Animals administered a protease vaccine with at least one booster shot usually become competent at about the same time as would be expected for any vaccine treatment. For example, animals administered a booster dose about 4 to 6 weeks after a primary dose usually become competent within another about 3 to 4 weeks. Animals administered a composition including an anti-flea protease antibody or protease inhibitor become competent as soon as appropriate serum levels of the compound are achieved, usually with one to three days.

In a preferred embodiment, a composition of the present invention when administered to a host animal is able to reduce flea viability by at least about 50 percent within at least about 21 days after the fleas begin feeding from the treated animal. (Note that fleas usually live about 40 days to about 50 days on one or more animals.) A more preferred composition when administered to a host animal is able to reduce flea viability by at least about 65 percent within at least about 14 days after the fleas begin feeding from the treated animal. An even more preferred composition when administered to an animal is able to reduce flea viability by at least about 90 percent within at least about 7 days after the fleas begin feeding from the treated animal.

In another preferred embodiment, a composition of the present invention when administered to a host animal is able to reduce flea fecundity (i.e., egg laying ability) by at least about 50 percent, more preferably by at least about 70 percent, and even more preferably by at least about 90 percent, within at least about 30 days after the fleas begin feeding from the treated animal. (Note that fleas usually do not begin laying eggs until about 7 days after taking a blood meal.)

In accordance with the present invention, compositions are administered to an animal in a manner such that the animal becomes competent to reduce flea protease activity in a flea that feeds from the competent; i.e., the animal becomes a treated animal. For example, a flea protease vaccine of the present invention, when administered to an animal in an effective manner, is able to elicit (i.e., stimulate) an immune response that produces an antibody titer in the blood stream of the animal sufficient to reduce flea protease activity. Similarly, an anti-flea protease antibody of the present invention, when administered to an animal in an effective manner, is administered in an amount so as to be present in the animal's blood stream at a titer that is sufficient to reduce flea protease activity. A protease inhibitor compound of the present invention, when administered to an animal in an effective manner, is administered in a manner so as to be present in the animal's blood stream at a concentration that is sufficient to reduce flea protease activity. Oligonucleotide nucleic acid molecules of the present invention can also be administered in an effective manner, thereby reducing expression of flea proteases.

Compositions of the present invention can be administered to animals prior to or during flea infestation. It is to be noted that when vaccines of the present invention are administered to an animal, a time period is required for the animal to elicit an immune response before the animal is competent to inhibit protease activity of fleas feeding from that animal. Methods to obtain an immune response in an animal are known to those skilled in the art.

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from flea infestation when administered one or more times over a suitable time period. For example, a preferred single dose of a protease vaccine or a mimetope thereof ranges from about 1 microgram ($\mu$g, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from flea infestation. A preferred administration schedule is one in which from about 10 $\mu$g to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-flea protease antibody composition or a mimetope thereof ranges from about 1 $\mu$g to about 10 mg of the composition per kilogram body weight of the animal. Anti-flea antibodies can be re-administered from about 1 hour to about biweekly for several weeks following the original administration. Booster treatments preferably are administered when the titer of antibodies of the animal becomes insufficient to protect the animal from flea infestation. A preferred administration schedule is one in which from about 10 $\mu$g to about 1 mg of an anti-flea protease antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein (e.g., flea protease vaccine, anti-flea protease antibody, or proteinaceous protease inhibitor) or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. When administered to an animal, a recombinant virus particle vaccine of the present invention infects cells within the immunized animal and directs the production of a protective protein or RNA nucleic acid molecule that is capable of protecting the animal from disease caused by a parasite of the present invention. A preferred single dose of a recombinant virus particle vaccine of the present invention is from about $1\times10^4$ to about $1\times10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

Compositions of the present invention can be administered to any animal susceptible to flea infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

The present invention includes compositions to treat flea infestation by any flea. As such, compositions of the present invention can be derived from any flea species. Preferred fleas to target include fleas of the following genera: Ctenocephalides, Cyopsyllus, Diamanus (Oropsylla), Echidnophaga, Nosopsyllus, Pulex, Tunga, and Xenopsylla, with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred. Particularly preferred fleas from which to protect animals include fleas of the species *Ctenocephalides felis, Ctenocephalides canis,* and Pulex species (e.g., *Pulex irritans* and *Pulex simulans*). It is also within the scope of the present invention to administer compositions of the present invention directly to fleas.

The present invention also includes the use of compositions of the present invention to reduce infestation by other ectoparasites as well as the use of compositions including protease vaccines, anti-protease antibodies and compounds that inhibit protease synthesis and/or activity derived from any ectoparasite to reduce ectoparasite infestation, particularly controlled release formulations containing such compositions. Preferred ectoparasites to target include arachnids, insects and leeches. More preferred ectoparasites to target include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasites to target include fleas, mosquitos, midges, sandflies, blackflies, ticks and Rhodnius.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., Borovsky, *Arch Insect Biochem. and Phys.*, 7:187–210, 1988, and related references. Examples 1 through 21, and the the sequence information provided in the sequence listing therein, of related PCT Publication No. WO 96/11706, published Apr. 25, 1996, are incorporated herein by this reference in their entirety.

Example 1

This example describes the cloning and sequencing of a flea cysteine protease nucleic acid molecule.

A flea cysteine protease nucleic acid molecule, referred to herein as nfCP1$_{573}$ was produced by PCR amplification using the following method. Primer Cal3F (designed to obtain a calreticulin gene), having nucleic acid sequence 5' TTG GGA TAC ACT TTG ACT GTT AAC C 3', represented herein as SEQ ID NO:97 was used in combination with the M13 universal primer, to PCR amplify, using standard techniques, a DNA fragment from a bovine blood-fed whole flea cDNA expression library as described above in Example 8 of related PCT Publication No. WO 96/11706. Surprisingly, the isolated DNA fragment correlated with a cysteine protease nucleic acid sequence. Sequence from this DNA fragment was used to design primer Cys1R, having the nucleic acid sequence 5' GTG AGC AAC CAT TAT TTC CAT ATC 3', represented herein as SEQ ID NO:98, which was used in a second PCR amplification in combination with the M13 reverse primer. A third PCR amplification was performed using primer Cys1F, having the nucleic acid sequence 5' CTT TCC TCA CAA TAC CAC CAA GGA AGC 3', represented herein as SEQ ID NO:74, in combination with the M13 universal primer. A fourth PCR amplification was performed using primer Cys2F, having the nucleic acid sequence 5' CTT GTA CGA TTG TCT CAA CAG GC 3', represented herein as SEQ ID NO:76, in combination with the M13 universal primer. The resulting PCR products were each gel purified and cloned into the TA Vector® System, and subjected to standard DNA sequencing techniques. A composite nucleic acid sequence representing a flea cysteine protease coding region was deduced, referred to herein as $nfCP1_{573}$, was deduced and is denoted herein as SEQ ID NO:76. Translation of SEQ ID NO:76 suggests that nucleic acid molecule $nfCP1_{573}$ encodes a non-full-length flea cysteine protease protein of about 191 amino acids, referred to herein as $PfCP1_{191}$, having amino acid sequence SEQ ID NO:77, assuming the first codon spans from about nucleotide 1 through about nucleotide 3 of SEQ ID NO:76.

The nucleic acid and amino acid sequences of the $nfCP1_{573}$ nucleic acid molecule and $PfCP1_{191}$ protein, respectively, were compared to known nucleic acid and amino acid sequences using a Genbank homology search. SEQ ID NO:77 was found to be similar to the amino acid sequence of *P. sativum* cysteine protease. The most highly conserved region of continuous similarity between SEQ ID NO:77 and *P. sativum* cysteine protease amino acid sequences spans from about amino acid 71 through about amino acid 165 of SEQ ID NO:77 and from about amino acid 17 through about amino acid 168 of the *P. sativum* cysteine protease, there being about 42% identity between the two regions. Comparison of the nucleic acid sequence encoding amino acids from about 205 through about 492 of $nfCP1_{573}$ indicate that those regions are about 54% identical.

Example 2

This example describes the cloning and sequencing of certain flea serine protease nucleic acid molecules.

Certain serine protease cDNA nucleic acid molecules have been isolated from reverse transcriptase PCR amplification of mRNA isolated from cat blood-fed whole fleas. The mRNA was isolated from fleas gathered over 72 hours after the initiation of feeding on cat blood. As such, the mRNA comprised a mixture of mRNA isolated at different time points over 72 hours. The mRNA was isolated using ground-up fleas, extracting total flea RNA using Tri-Reagent (available from Molecular Research Center, Cincinnati, Ohio) and an Invitrogen Fast Track™ RNA isolation kit (available from Invitrogen, Inc. San Diego, Calif.). cDNA was synthesized using a Stratagene RT-PCR kit (available from Stratagene, Inc, San Diego, Calif.). Primers used for first-strand cDNA synthesis included an equal molar mixture of the following: 5'dT-2VT3' and 5'dT-2VC3' (as provided in a differential display kit, available from Operon Technologies, Inc. Alameda, Calif.).

The actual primers used in the PCR amplification of the cDNA described above included cat-try #2 (SEQ ID NO:86) used in combination with H57 primer (SEQ ID NO:99). The resultant PCR products were gel purified and cloned into the TA Vector™. Recombinant TA vector clones were isolated and the nucleic acid molecules were subjected to nucleic acid sequencing using analysis as described above.

A. A nucleic acid sequence of a flea serine protease nucleic molecule, namely $nfSP24_{410}$, is represented herein as SEQ ID NO:78. Translation of SEQ ID NO:78. suggests that nucleic acid molecule $nfSP24_{410}$, encodes a non-full-length flea serine protease protein of about 136 amino acids, referred to herein as $PfSP24_{136}$, having amino acid sequence SEQ ID NO:79, assuming the first codon spans from about nucleotide 1 through about nucleotide 3 of SEQ ID NO:78. A Genbank homology search revealed most homology between SEQ ID NO:79 and an *Anopheles gambiae* chymotrypsin protein sequence, there being about 38% identity between corresponding regions of the two amino acid sequences.

B. Another nucleic acid sequence of a flea serine protease nucleic molecule, namely $nfSP33_{426}$, is represented herein as SEQ ID NO:82. Translation of SEQ ID NO:82 suggests that nucleic acid molecule $nfSP33_{426}$ encodes a non-full-length flea serine protease protein of about 142 amino acids, referred to herein as $PfSP33_{142}$, having amino acid sequence SEQ ID NO:83, assuming the first codon spans from about nucleotide 1 through about nucleotide 3 of SEQ ID NO:82. A Genbank homology search revealed most homology between SEQ ID NO:83 and a Drosophila serine protease stubble protein sequence, there being about 45% identity between corresponding regions of the two amino acid sequences.

Example 3

This example describes the cloning and sequencing of a flea serine protease nucleic acid molecule.

A serine protease cDNA nucleic acid molecule was isolated in a manner similar to that described in Example 8 of related PCT Publication No. WO 96/11706. The actual primers used in PCR amplification of the serine protease nucleic acid molecule from a cat blood-fed whole flea cDNA expression library (produced as described in Example 2) included cat-try #2 (SEQ ID NO:86) in combination with M13 reverse primer (SEQ ID NO:87). The resulting PCR product was diluted 1:25 and used as a template in a second PCR reaction using the forward vector primer T3 in combination with the reverse primer (derived from the nucleic acid sequence of $nfSP33_{778}$, described in Example 2) having the nucleic acid sequence 5' ATT CCT CGT GGT TCA GTC GCT C 3', represented herein as SEQ ID NO:100. The resultant PCR product was gel purified and cloned into the TA Vector™. The clones were subjected to nucleic acid sequencing as described above.

A nucleic acid sequence of a flea serine protease nucleic molecule, namely $nfSP33_{778}$ is represented herein as SEQ ID NO:84. As expected, SEQ ID NO:84 includes a portion of SEQ ID NO:82. Translation of SEQ ID NO:84 suggests that nucleic acid molecule $nfSP33_{778}$ encodes a non-full-length flea serine protease protein of about 259 amino acids, referred to herein as $PfSP33_{259}$, having amino acid sequence SEQ ID NO:85, assuming the first codon spans from about nucleotide 2 through about nucleotide 4 of SEQ ID NO:84. A Genbank homology search revealed most homology between SEQ ID NO:84 and a Drosophila serine protease stubble gene, there being about 54% identity between nucleotides 23–778 of SEQ ID NO:84 and nucleotides 2324–3064 of the Drosophila serine protease stubble gene.

Example 4

This example describes the cloning and sequencing of certain larval flea serine protease nucleic acid molecules.

Certain serine protease cDNA nucleic acid molecules have been isolated from a mixed instar larval cDNA library produced using 1st, 2nd and 3rd instar larvae fed on cat blood, by PCR amplification. The actual primers used in the PCR amplification included either cat-try #2 (SEQ ID NO:86) in combination with either H57 primer (SEQ ID NO:99) or M13 reverse primer (SEQ ID NO:87). The resultant PCR products were gel purified and cloned into the TA Vector™. Three recombinant TA vector clones were isolated containing PCR products using cat-try #2 and M13 reverse as primers and one clone was isolated containing PCR products using cat-try #2 and H57 primers. These newly cloned nucleic acid molecules were subjected to nucleic acid sequencing as described above.

A. A nucleic acid sequence of a larval flea serine protease nucleic molecule isolated using cat-try #2 and H57 primers, namely nfSP32$_{433}$, is represented herein as SEQ ID NO:80. Translation of SEQ ID NO:80 suggests that nucleic acid molecule nfSP32$_{433}$ encodes a non-full-length flea serine protease protein of about 144 amino acids, referred to herein as PfSP32$_{144}$, having amino acid sequence SEQ ID NO:81, assuming the first codon spans from about nucleotide 1 through about nucleotide 3 of SEQ ID NO:80. A Genbank homology search revealed most homology between SEQ ID NO:80 and an *Anopheles gambiae* trypsin gene, there being about 52% identity between corresponding regions of the two nucleic acid molecules.

Example 5

This example describes the isolation and characterization of a 31 kD flea serine protease.

Guts from about 1500 fleas that had been fed on cat blood for about 24 hours were dissected in Gut Dissection Buffer (50 mM Tris 8.0, 100 mM CaCl$_2$). The guts were disrupted by freezing and thawing 4 times, followed by sonication. The resulting extracts were clarified by centrifugation for 20 minutes at 14,000 rpm in a microfuge at 4° C. The supernatant was recovered.

The gut supernatant was loaded onto a 3 ml column comprising p-aminobenzamidine cross-linked to Sepharose beads (Sigma), previously equilibrated in Benzamidine Column Buffer (50 mM Tris 8.0, 100 mM CaCl$_2$, 400 mM NaCl). The supernatant was incubated on the column for about 10 min. Unbound protein was slowly washed off the column using Benzamidine Column Buffer until no protein was detectable by Bradford Assay (Bio Rad).

Proteases bound to the benzamidine column were then eluted using 10 ml Benzamidine Column Buffer supplemented with 10 mM p-aminobenzamidine (brought to pH 8.0 with NaOH). Proteases in the eluant were concentrated and diafiltered into a volume of about 0.3 ml Gut Dissection Buffer using a Microcon 3 concentrator (Amicon).

About 120 μl of the concentrated eluant was further concentrated to a volume of about 30 μl. Proteases contained in this concentrate were resolved by gel electrophoresis on a 14% Tris-Glycine electrophoresis gel (15 μl per lane= approximately 300 gut equivalents per lane). After electrophoresis, the separated proteases were blotted onto a PVDF membrane using a CAPS buffer (10 mM CAPS pH 11, 0.5 mM DTT) The membrane was stained with Coomassie Brilliant Blue. A dominant protein band of about 31 kDa was visualized. The membrane was then used for automated N-terminal sequencing (described in Example 7 of related PCT Publication No. WO 96/11706). A partial N-terminal amino acid sequence of the flea protease was determined to be IVGGEDVDISTCGWC (denoted SEQ ID NO:68).

Example 6

This example describes the isolation and characterization of a 31 kD flea serine protease contained in a formulation having IgGase activity (i.e., ability to proteolyze immunoglobulin G proteins).

Cat blood-fed flea gut extracts were prepared and selected on a benzamidine column as described above in Example 5. IgG protease activity was assayed by incubating at 37° C., overnight, the benzamidine eluant with cat immunoglobulin G proteins (IgG) purified on Protein A sepharose. The ability of the flea gut benzamidine eluant to digest cat IgG was detected by resolving the samples by gel electrophoresis through a 14% SDS-PAGE gel and silver staining the gel using standard methods. The marked decrease (compared with control samples lacking protease activity) of a 50 kDa band on the silver stained gel, representing cat IgG heavy chain, indicated that the benzamidine eluant contains IgG protease activity.

The benzamidine eluant was then purified on a PolyPropylaspartamide hydrophobic interaction chromatography (HIC) column by applying the eluant to the column in buffer containing 0.1 M KPO$_4$, pH 6.5 and 2 M (N$_4$H$_2$) S$_4$O. Proteases bound to the column were eluted using an ammonium sulfate gradient of 2 M to 0 M in HIC column buffer. Column fractions were tested for IgG protease activity using the method described above. Fractions containing IgG protease activity were pooled and applied to a PolyCat cation exchange column in 20 M sodium acetate, pH 6. The proteins were eluted using a sodium chloride gradient of 0 M to 1 M NaCl in 20 M sodium acetate. Fractions eluted from the column were tested for IgG protease activity and then each fraction was resolved by electrophoresis using SDS-PAGE. Fractions having the highest levels of IgG protease activity included a protein band that migrated at about 31 kDa on the SDS-PAGE gel. Weaker protease activity corresponded to an about 28 kDa band.

The 31 kDa protein present on the SDS-PAGE gel was used for N-terminal amino acid sequencing using the blotting method described above. A partial N-terminal amino acid sequence was determined to be IVGGEDVDIST(C) GWQI(S)FQ(S)ENLHF(C)GG(S)IIAPK (denoted herein as SEQ ID NO:69). A comparison of SEQ ID NO:69 and SEQ ID NO:68 (described in Example 5) indicates a single residue difference between the two amino acid sequences at residue 15 of each sequence (i.e., Q and V, respectively). Since SEQ ID NO:69 correlates with IgGase activity, the data suggests that the larval protein containing SEQ ID NO:68 has IgGase activity.

Example 7

This example describes the cloning and sequencing of a 31 kDa flea serine protease contained in a formulation having IgGase activity.

A flea protease nucleic acid molecule was isolated from a cat blood-fed whole flea library (described in Example 2) and a bovine blood-fed whole flea library (described in Example 8 of related PCT Publication No. WO 96/11706) by PCR amplification. The actual primers used in the PCR amplification included FP31A primer designed using the N-terminal amino acid sequence SEQ ID NO:68, the primer having the nucleic acid sequence 5' GAA GAT GTW GAT ATT TCW ACA TGT GG 3' (SEQ ID NO:101) used in combination with the M13 universal primer. The resultant PCR products were gel purified and cloned into the TA Vector™ and subjected to nucleic acid sequencing as described above.

A FP31B primer (5' GAA AAT GAA ATC CAC TTA AAC ATT ACG 3'), (represented herein as SEQ ID NO:102) was designed using the DNA sequence of a DNA fragment from a bovine blood-fed cDNA library. A flea protease cDNA nucleic acid molecule was isolated by PCR amplification of the cat blood-fed whole flea library and the bovine blood-fed whole flea library described above by PCR amplification. PCR amplification was performed using the FP31B primer in combination with M13 reverse primer. The resulting PCR products were then diluted 1:25, and used as a template for a second PCR reaction using primer FP31C, having the sequence 5' CTC TTA TTG TAC GAG GGA TGC 3' (denoted herein SEQ ID NO:103) in combination with T3 primer. The resulting nested PCR product was cloned into TA Vector™ and subjected to DNA sequencing.

The nucleic acid sequence of the resulting flea serine protease nucleic molecule, namely nfSP28$_{923}$ is represented herein as SEQ ID NO:66. Translation of SEQ ID NO:66 yields a protein of about 267 amino acids, denoted PfSP28$_{267}$, having amino acid sequence SEQ ID NO:67, assuming an open reading frame in which the putative start codon spans from about nucleotide 8 through about nucleotide 10 of SEQ ID NO:66 or from about nucleotide 11 through about nucleotide 13, and a stop codon spanning from about nucleotide 803 through about nucleotide 805 of SEQ ID NO:66. SEQ ID NO:67 contains SEQ ID NO:68 except Q is substituted for C, and SEQ ID NO:69. A Genbank homology search revealed most homology between SEQ ID NO:66 and *Bombix mori* vitellin-degrading protease gene, there being about 53% identity between corresponding regions of the two nucleic acid sequences.

Example 8

This example provides additional nucleic acid and deduced amino acid sequences of nucleic acid molecules encoding a flea cysteine protease protein of the present which was described in Example 1. This example also provides the production of a cysteine protease protein in *E. coli* cells.

A. Additional Cysteine Protease Nucleic Acid Molecule

The PCR products described in Example 1 were submitted to additional nucleic acid sequence analysis in order to obtain the nucleic acid sequence of additional portions of the coding region of the cysteine protease gene. A composite nucleic acid sequence representing a flea cysteine protease coding region, referred to herein as nfCP1$_{1109}$, was deduced and is denoted herein as SEQ ID NO:1. SEQ ID NO:76 is contained within the sequence of the nucleic acid molecule nfCP1$_{1109}$. Translation of SEQ ID NO:1 suggests that nucleic acid molecule nfCP1$_{1109}$ encodes a full-length flea cysteine protease protein of about 327 amino acids, referred to herein as PfCP1$_{327}$, having amino acid sequence SEQ ID NO:2, assuming an open reading frame in which the initiation codon spans from about nucleotide 126 through about nucleotide 128 of SEQ ID NO:1 and the termination codon spans from about nucleotide 1107 through about nucleotide 1109 of SEQ ID NO:1. The complement of SEQ ID NO:1 is represented herein by SEQ ID NO:3. The coding region encoding PfCP1$_{327}$, is represented by nucleic acid molecule nfCP1$_{984}$, having a coding strand with the nucleic acid sequence represented by SEQ ID NO:4 and a complementary strand with nucleic acid sequence SEQ ID NO:6. The proposed mature protein, denoted herein as PfCP1$_{226}$, contains about 226 amino acids which is represented herein as SEQ ID NO:8. The nucleic acid molecule encoding PfCP1$_{226}$ is denoted herein as nfCP1$_{681}$, which is represented by SEQ ID NO:7. The amino acid sequence of PfCP1$_{327}$ (i.e., SEQ ID NO:2) predicts that PfCP1$_{327}$ has an estimated molecular weight of about 42 kD and an estimated pI of about pI 8.84.

Comparison of nucleic acid sequence SEQ ID NO:1 with nucleic acid sequences reported in GenBank indicates that SEQ ID NO:1 showed the most homology, i.e., about 55% identity, with the following three genes: a Drosophila cysteine protease gene, a Bombyx cysteine protease gene and a Sarcophaga cysteine protease gene. Comparison of amino acid sequence SEQ ID NO:2 (i.e., the amino acid sequence of PfCP1$_{327}$) with amino acid sequences reported in GenBank indicates that SEQ ID NO:2 showed the most homology, i.e., about 42% identity, with the following three proteins: a Drosophila cysteine protease protein, a Bombyx cysteine protease protein and a Sarcophaga cysteine protease protein.

B. Production of Cysteine Protease Protein in *E. coli* cells.

An about 660-bp nucleic acid molecule, referred to herein as nfCP1$_{660}$ (designed to encode an apparently mature cysteine protease protein) was PCR-amplified from a flea mixed instar cDNA library produced using unfed 1st instar, bovine blood-fed 1st instar, bovine blood-fed 2$^{nd}$ instar and bovine blood-fed 3$^{rd}$ instar flea larvae (this combination of tissues is referred to herein as mixed instar larval tissues for purposes of this example). Total RNA was extracted from mixed instar tissue using an acid-guanidinium-phenol-chloroform method similar to that described by Chomczynski et al., 1987, *Anal. Biochem.* 162, p. 156–159. Approximately 5,164 mixed instar larvae were used in each RNA preparation. Poly A+ selected RNA was separated from each total RNA preparation by oligo-dT cellulose chromatography using Poly(A)Quick® MRNA isolation kits (available from Stratagene Cloning Systems, La Jolla, Calif.), according to the method recommended by the manufacturer. A mixed instar cDNA expression library was constructed in lambda (λ) Uni-ZAP™XR vector (available from Stratagene is Cloning Systems) using Stratagene's ZAP-cDNA Synthesis Kit® protocol. About 6.34 μg of mixed instar poly A+ RNA were used to produce the mixed instar library. The resultant mixed instar library was amplified to a titer of about 2.17×10$^{10}$ pfu/ml with about 97% recombinants. The primers used in the PCR amplification were sense primer CysBS' having the nucleotide sequence 5' GAT AAG GAT CCG TTA CCA GAT TCT TTC GAC TGG 3' (containing a BamHI-site; denoted SEQ ID NO:64) and anti-sense primer CysHA having the nucleotide sequence 5' TTA TCA AGC TTC CAT TTA CAT GCC GTA AAA ATC 3' (containing a HindIII site; denoted SEQ ID NO:65). The resulting PCR product nfCP1$_{660}$ was submitted to nucleic acid sequence analysis to obtain a nucleic acid sequence of the coding strand, represented herein as SEQ ID NO:94. Translation of SEQ ID NO:94 indicated that nfCP1$_{696}$ encodes a protein of about 220 amino acids, called PfCP1$_{220}$, having SEQ ID NO:95. It is to be noted that this sequence analysis indicated that the stop codon was actually about 36 base pairs upstream from what had been predicted by SEQ ID NO:1; as such, the protein encoded by nfCP1$_{660}$ is about 12 amino acids shorter than would have been predicted by SEQ ID NO:1. The nucleic acid molecule nfCP1$_{660}$ contains the coding region for PfCP1$_{220}$.

Recombinant cell *E. coli*:pCro-nfCP1$_{660}$ is produced in the following manner. Nucleic acid molecule nfCP1$_{660}$ is digested with BamHI and HindIII restriction endonucleases, gel purified, and subcloned into expression vector lambdaP$_R$/T$^2$ori/S10HIS-RSET-A9 (the production of which is described in Tripp et al, International PCT Publication No. WO 95/24198, published Sep. 14, 1995; see in particular, Example 7), that is digested with BamHI and HindIII and dephosphorylated. The resultant recombinant molecule, referred to herein as pCro-nfCP1$_{660}$, is transformed into *E. coli* BL-21 competent cells (available from Novagen, Madison, Wis.) to form recombinant cell *E.* coli:pCro-nfCP1$_{660}$. The recombinant cell is cultured as described in Example 20 of related PCT Publication No. WO 95/24198. About 1 ml of culture is collected prior to induction, and about 1 ml of culture is collected about 60 minutes following induction. These samples are then lysed in sodium dodecyl sulfate polyacrylamide gel electrophoresis (SDS-PAGE) loading buffer, resolved on a 14% Tris-glycine acrylamide gel and analyzed by immunoblot using a T7 (tag) antibody (available from Novagen).

Example 9

This example provides additional nucleic acid and deduced amino acid sequences of nucleic acid molecules encoding serine protease proteins of the present invention which are described herein and in the Examples section of related PCT Publication No.WO 96/11706.

A. A DNA probe labeled with $^{32}$P comprising nucleotides from nfAP2$_{2100}$ (described in Example 23 of related U.S. patent application Ser. No. 08/639,075, filed Apr. 24, 1996) was used to screen a bovine blood-fed whole flea cDNA library (described in Example 8 of related PCT Publication No.WO 96/11706) using standard hybridization techniques. A clone was isolated having about a 459-nucleotide insert, referred to herein as nfSP18$_{459}$.

A nucleic acid sequence of the composite nucleic acid molecule produced using nucleic acid sequence from nfSP18$_{534}$ and nfSP18$_{459}$ is referred to herein as nfSP18$_{775}$, having a nucleic acid sequence of the coding strand which is denoted herein as SEQ ID NO:9. Translation of SEQ ID NO:9 suggests that nucleic acid molecule nfSP18$_{775}$ encodes a non-full-length flea serine protease protein of about 228 amino acids, referred to herein as PfSP18$_{228}$, having amino acid sequence SEQ ID NO:10, assuming the first codon spans from about nucleotide 1 through about nucleotide 3 of SEQ ID NO:9 and the stop codon spans from about nucleotide 685 through about nucleotide 687 of SEQ ID NO:9. The complement of SEQ ID NO:9 is represented herein by SEQ ID NO:11. The coding region encoding PfSP18$_{228}$, is represented by nucleic acid molecule nfSP18$_{225}$, having a coding strand with the nucleic acid sequence represented by SEQ ID NO:12 and a complementary strand with nucleic acid sequence SEQ ID NO:14. The amino acid sequence of PfSP18$_{228}$ (i.e., SEQ ID NO:10) predicts that PfSP18$_{228}$ has an estimated molecular weight of about 25 kD and an estimated pI of about 9.09.

Comparison of nucleic acid sequence SEQ ID NO:9 with nucleic acid sequences reported in GenBank indicates that SEQ ID NO:9 showed the most homology, i.e., about 51% identity, between SEQ ID NO:9 and an *Anopheles stephensi* trypsin 1 gene. Comparison of amino acid sequence SEQ ID NO:10 (i.e., the amino acid sequence of PfSP18$_{228}$) with amino acid sequences reported in GenBank indicates that SEQ ID NO:10 showed the most homology, i.e., about 59% identity between SEQ ID NO:10 and *Vespa crabro* protein.

B. The remainder of flea serine protease nucleic molecule clone 24 (described in Example 2 was determined using primers designed from nfSP24$_{410}$ to amplify DNA from the bovine blood-fed whole flea cDNA library. Sense primer Flea 24F having the nucleotide sequence 5' GGA CAA ACT GTT CAT TGC AG 3' (denoted SEQ ID NO:46) was used in combination with the M13 universal primer in a first PCR reaction. Anti-sense primer Flea 24R having the nucleotide sequence 5' CCC TCA TTT GTC GTA ACT CC 3' (denoted SEQ ID NO:47) was used in combination with the M13 reverse primer in a second PCR reaction. The resulting PCR products were each gel purified and cloned into the TA Vector® System, and subjected to standard DNA sequencing techniques.

A composite nucleic acid sequence representing a flea serine protease coding region was deduced, referred to herein as nfSP24$_{1089}$, was deduced and is denoted herein as SEQ ID NO:15. SEQ ID NO:78 is contained within the sequence of the nucleic acid molecule nfSP24$_{1089}$. Translation of SEQ ID NO:15 suggests that nucleic acid molecule nfSP24$_{1089}$ encodes a full-length flea serine protease protein of about 258 amino acids, referred to herein as PfSP24$_{258}$, having amino acid sequence SEQ ID NO:16, assuming an open reading frame in which the initiation codon spans from about nucleotide 33 through about nucleotide 35 of SEQ ID NO:15 and the termination codon spans from about nucleotide 807 through about nucleotide 809 of SEQ ID NO:15. The complement of SEQ ID NO:15 is represented herein by SEQ ID NO:17. The coding region encoding PfSP24$_{258}$, is represented by nucleic acid molecule nfSP24$_{774}$, having a coding strand with the nucleic acid sequence represented by SEQ ID NO:18 and a complementary strand with nucleic acid sequence SEQ ID NO:20. The proposed mature protein, denoted herein as PfSP24$_{237}$, contains about 237 amino acids which is represented herein as SEQ ID NO:22. The nucleic acid molecule encoding PfSP24$_{237}$ is denoted herein as nfSP24$_{711}$, which is represented by SEQ ID NO:21. The amino acid sequence of PfSP24$_{258}$ (i.e., SEQ ID NO:16) predicts that PfSP24$_{258}$ has an estimated molecular weight of about 28 kD and an estimated pI of about pI 6.70.

Comparison of nucleic acid sequence SEQ ID NO:15 with nucleic acid sequences reported in GenBank indicates that SEQ ID NO:15 showed the most homology, i.e., about 51% identity between SEQ ID NO:15 and an *Anopheles stephensi* trypsin 1 gene. Comparison of amino acid sequence SEQ ID NO:16 (i.e., the amino acid sequence of PfSP24$_{258}$) with amino acid sequences reported in GenBank indicates that SEQ ID NO:16 showed the most homology, i.e., about 59% identity between SEQ ID NO:16 and an *Anopheles gambiae* chymotrypsin II protein.

C. The remainder of flea serine protease nucleic molecule clone 32 (described in Example 8 was determined using primers designed from nfSP32$_{433}$ to amplify DNA from the cat-fed whole flea cDNA library. Sense primer Flea 32F having the nucleotide sequence 5' GGC TAG GTT AGT GGA TTC TGG 3' (denoted SEQ ID NO:48) was used in combination with the M13 universal primer in a first PCR reaction. Anti-sense primer Flea 32R having the nucleotide sequence 5' GCA AAT CAG TTC CAG AAT CCA CTA ACC 3' (denoted SEQ ID NO:49) was used in combination with the M13 reverse primer in a second PCR reaction. The resulting PCR products were each gel purified and cloned into the TA Vector® System, and subjected to standard DNA sequencing techniques.

A composite nucleic acid sequence representing a flea serine protease coding region was deduced, referred to herein as nfSP32$_{924}$, was deduced and is denoted herein as SEQ ID NO:23. SEQ ID NO:80 is contained within the sequence of the nucleic acid molecule nfSP32$_{924}$. Translation of SEQ ID NO:23 suggests that nucleic acid molecule nfSP32$_{924}$ encodes a full-length flea serine protease protein of about 268 amino acids, referred to herein as PfSP32$_{268}$, having amino acid sequence SEQ ID NO:24, assuming an open reading frame in which the initiation codon spans from about nucleotide 6 through about nucleotide 8 of SEQ ID NO:23 and the termination codon spans from about nucleotide 810 through about nucleotide 812 of SEQ ID NO:23. The complement of SEQ ID NO:23 is represented herein by SEQ ID NO:25. The coding region encoding PfSP32$_{268}$, is represented by nucleic acid molecule nfSP32$_{699}$, having a coding strand with the nucleic acid sequence represented by SEQ ID NO:26 and a complementary strand with nucleic acid sequence SEQ ID NO:28. The amino acid sequence of PfSP32$_{268}$ (i.e., SEQ ID NO:24) predicts that PfSP32$_{268}$ has an estimated molecular weight of about 28.6 kD and an estimated pI of about pI 7.36.

Comparison of nucleic acid sequence SEQ ID NO:23 with nucleic acid sequences reported in GenBank indicates that SEQ ID NO:23 showed the most homology, i.e., about 52% identity between SEQ ID NO:23 and a *Fusarium oxysporum* preprotrypsin gene. Comparison of amino acid sequence SEQ ID NO:24 (i.e., the amino acid sequence of PfSP32$_{268}$) with amino acid sequences reported in GenBank indicates that SEQ ID NO:24 showed the most homology, i.e., about 63% identity between SEQ ID NO:24 and a *Bombyx mori* vitellin -degrading protease precursor protein.

D. The remainder of flea serine protease nucleic molecule clone 33 was determined using primers designed from nfSP33$_{778}$ to amplify DNA from the flea mixed instar larvae cDNA library described above in Example 19. Sense primer Flea 33F having the nucleotide sequence 5' CAG GGC GCT CTG CAG AAC GCA AC 3' (denoted SEQ ID NO:50) was used in combination with the M13 universal primer in a first PCR reaction. Anti-sense primer Flea 33R having the nucleotide sequence 5' ATT CCT CGT GGT TCA GTC GCT C 3' (denoted SEQ ID NO:51) was used in combination with the M13 reverse primer in a second PCR reaction. The resulting PCR products were each gel purified and cloned into the TA Vector® System, and subjected to standard DNA sequencing techniques.

A composite nucleic acid sequence representing a flea serine protease coding region was deduced, referred to herein as nfSP33$_{1894}$, was deduced and is denoted herein as SEQ ID NO:29. SEQ ID NO:84 and SEQ ID NO:82 are contained within the sequence of the nucleic acid molecule nfSP33$_{1894}$. Translation of SEQ ID NO:29 suggests that nucleic acid molecule nfSP33$_{1894}$ encodes a full-length flea serine protease protein of about 400 amino acids, referred to herein as PfSP33$_{400}$, having amino acid sequence SEQ ID NO:30, assuming an open reading frame in which the initiation codon spans from about nucleotide 335 through about nucleotide 337 of SEQ ID NO:29 and the termination codon spans from about nucleotide 1535 through about nucleotide 1537 of SEQ ID NO:29. The complement of SEQ ID NO:29 is represented herein by SEQ ID NO:31. The coding region encoding PfSP33$_{400}$, is represented by nucleic acid molecule nfSP33$_{1200}$, having a coding strand with the nucleic acid sequence represented by SEQ ID NO:32 and a complementary strand with nucleic acid sequence SEQ ID NO:34. The proposed mature protein, denoted herein as PfSP33$_{242}$, contains about 242 amino acids which is represented herein as SEQ ID NO:36. The nucleic acid molecule encoding PfSP33$_{242}$ is denoted herein as nfSP33$_{726}$, which is represented by SEQ ID NO:35. The amino acid sequence of PfSP33$_{400}$ (i.e., SEQ ID NO:30) predicts that PfSP33$_{400}$ has an estimated molecular weight of about 44 kD and an estimated pI of about pI 7.59.

Comparison of nucleic acid sequence SEQ ID NO:29 with nucleic acid sequences reported in GenBank indicates that SEQ ID NO:29 showed the most homology, i.e., about 48% identity between SEQ ID NO:29 and a *Drosophila melanogaster* serine protease stubble gene. Comparison of amino acid sequence SEQ ID NO:30 (i.e., the amino acid sequence of PfSP33$_{400}$) with amino acid sequences reported in GenBank indicates that SEQ ID NO:30 showed the most homology, i.e., about 63% identity between SEQ ID NO:30 and a *Drosophila melanogaster* serine protease stubble protein.

Example 10

This example provides nucleic acid and deduced amino acid sequence of another nucleic acid molecule encoding a serine protease protein of the present invention.

A serine protease cDNA nucleic acid molecules has been isolated in a manner similar to that described in Example 8 of related PCT Publication No.No.WO 96/11706. The actual primers used in PCR amplification of the serine protease nucleic acid molecule from a cat blood-fed flea cDNA expression library (produced as described in Example 8 of related PCT Publication No.No.WO 96/11706) included cat-try #2 (SEQ ID NO:86) in combination with H57 primer (SEQ ID NO:99). The resultant PCR product was gel purified and cloned into the TA Vector™. A recombinant TA vector clone was isolated and subjected to nucleic acid sequencing.

A composite nucleic acid sequence of a flea serine protease nucleic molecule corresponding to flea clone 40, namely nfSP40$_{428}$ was deduced and is denoted herein as SEQ ID NO:37. Translation of SEQ ID NO:37 suggests that nucleic acid molecule nfSP40$_{428}$ encodes a non-full-length flea serine protease protein of about 142 amino acids, referred to herein as PfSP40$_{142}$, represented herein by SEQ ID NO:38. The complement of SEQ ID NO:37 is represented herein by SEQ ID NO:39.

The remainder of flea serine protease nucleic molecule clone 40 was determined using primers designed from nfSP40$_{428}$ to amplify DNA from the cat blood-fed whole flea cDNA library. Sense primer Flea 40F having the nucleotide sequence 5' GGC AAG TTT CGT TTC ACA ATA GG 3' (denoted SEQ ID NO:52) was used in combination with the M13 universal primer in a first PCR reaction. Anti-sense primer Flea 40R having the nucleotide sequence 5' TCC AAC CCT AAC TTT TAA ACC TTC 3' (denoted SEQ ID NO:53) was used in combination with the M13 reverse primer in a second PCR reaction. The resulting PCR products were each gel purified and cloned into the TA Vector® System, and subjected to standard DNA sequencing techniques.

A composite nucleic acid sequence representing a flea serine protease coding region was deduced, referred to herein as nfSP40$_{841}$, was deduced and is denoted herein as SEQ ID NO:40. SEQ ID NO:37 is contained within the sequence of the nucleic acid molecule nfSP40$_{841}$. Translation of SEQ ID NO:40 suggests that nucleic acid molecule nfSP40$_{841}$ encodes a non-full-length flea serine protease protein of about 242 amino acids, referred to herein as PfSP40$_{242}$, having amino acid sequence SEQ ID NO:41, assuming an open reading frame in which the first codon spans from about nucleotide 2 through about nucleotide 4 of SEQ ID NO:40 and the termination codon spans from about nucleotide 728 through about nucleotide 730 of SEQ ID NO:40. The complement of SEQ ID NO:40 is represented herein by SEQ ID NO:42. The coding region encoding PfSP40$_{242}$, is represented by nucleic acid molecule nfSP40$_{717}$, having a coding strand with the nucleic acid sequence represented by SEQ ID NO:43 and a complementary strand with nucleic acid sequence SEQ ID NO:45. The amino acid sequence of PfSP40$_{242}$ (i.e., SEQ ID NO:41) predicts that PfSP40$_{242}$ has an estimated molecular weight of about 26 kD and an estimated pI of about pI 6.5.

Comparison of nucleic acid sequence SEQ ID NO:40 with nucleic acid sequences reported in GenBank indicates that SEQ ID NO:40 showed the most homology, i.e., about 57% identity between SEQ ID NO:40 and a *Dermatophagoides pteronyssinus* Der P3 allergen gene. Comparison of amino acid sequence SEQ ID NO:41 (i.e., the amino acid sequence of PfSP40$_{242}$) with amino acid sequences reported in GenBank indicates that SEQ ID NO:41 showed the most homology, i.e., about 40% identity between SEQ ID NO:41 and a *Bombyx mori* vitellin-degrading protease precursor protein.

Example 11

This Example demonstrates the production of serine protease proteins of the present invention in *E. coli* cells.

A. Flea serine protease protein PfSP24$_{258}$ was produced in the following manner. An about 714 bp nucleic acid molecule, referred to herein as nfSP24$_{714}$ (designed to encode an apparently mature serine protease protein) was PCR amplified from nfSP24$_{1089}$ using sense primer Flea 24 EF having the nucleotide sequence 5' CAC AGG ATC CAA TAA TTT GTG GTC AAA ATG C 3' (containing a BamHI-site; denoted SEQ ID NO:54) and anti-sense primer Flea 24 ER having the nucleotide sequence 5' AAA AAG AAA GCT TCT TTA ATT TTC TGA CAT TGT CGT G 3' (containing a HindIII; denoted SEQ ID NO:55). The resulting PCR product nfSP24$_{714}$ was digested with BamHI and HindIII restriction endonucleases, gel purified, and subcloned into expression vector lambdaP$_R$/T$^2$ori/S10HIS-RSET-A9, that had been digested with BamHI and HindIII and dephosphorylated. The resultant recombinant molecule, referred to herein as pCro-nfSP24$_{714}$, was transformed into *E. coli* BL-21 competent cells (available from Novagen, Madison, Wis.) to form recombinant cell *E. coli*:pCro-nfSP24$_{714}$. The recombinant cell was cultured as described in Example 20 of related PCT Publication No.WO 95/24198. About 1 ml of culture was collected prior to induction, and about 1 ml of culture was collected about 60 minutes following induction. These samples were then lysed in sodium dodecyl sulfate polyacrylamide gel electrophoresis (SDS-PAGE) loading buffer and resolved on a 14% Tris-glycine acrylamide gel. Immunoblot analysis of the proteins using a T7 (tag) antibody (available from Novagen) showed expression of an about 36 kD protein in the induced sample but not in the uninduced sample.

B. Flea serine protease protein PfSP32$_{268}$ was produced in the following manner. An about 698 bp nucleic acid molecule, referred to herein as nfSP32$_{698}$ (designed to encode an apparently mature serine protease protein) was PCR amplified from nfSP32$_{933}$ using sense primer Flea 32 EF having the nucleotide sequence 5' GCG GGA TCC TAT TGT GGG TGG TGA AGC AGT G 3' (containing a BamHI-site; denoted SEQ ID NO:56) and anti-sense primer Flea 32 ER having the nucleotide sequence 5' GAC GGT ACC ATG TAT AAA ATA ATA TTA AAC TCC GG 3' (containing a KpnI; denoted SEQ ID NO:57). The resulting PCR product nfSP32$_{698}$ was digested with BamHI and KpnI restriction endonucleases, gel purified, and subcloned into expression vector 1 pTrcHisB (available from InVitrogen Corp., San Diego, Calif.), that had been digested with BamHI and XpnI and dephosphorylated. The resultant recombinant molecule, referred to herein as pTrc-nfSP32$_{698}$, was transformed into *E. coli* BL-21 competent cells to form recombinant cell *E. coli*:pTrc-nfSP32$_{698}$. The recombinant cell was cultured and protein production resolved by SDS-PAGE as described above in Section A. Immunoblot analysis of the proteins using a T7 antibody showed expression of an about 38 kD protein in the induced sample but not in the uninduced sample.

C. Flea serine protease protein PfSP33$_{400}$ was produced in the following manner. An about 1200 bp nucleic acid molecule, referred to herein as nfSP33$_{1200}$ (designed to encode an apparently mature serine protease protein) was PCR amplified from nfSP33$_{1894}$ using sense primer Flea 33 EF having the nucleotide sequence 5' CCG GGA TCC TAT GTT AGC GAT CGT CCC GTC AAA C 3' (containing a BamHI-site; denoted SEQ ID NO:58) and anti-sense primer Flea 33 ER having the nucleotide sequence 5' CCG GAA TTC TTA TCC CAT TAC TTT GTC GAT CC 3' (containing a EcoRI; denoted SEQ ID NO:59). The resulting PCR product nfSP33$_{1200}$ was digested with BamHI and EcoRI restriction endonucleases, gel purified, and subcloned into expression vector lambdaP$_R$/T$^2$ori/S10HIS-RSET-A9, that had been digested with BamHI and EcoRI and dephosphorylated. The resultant recombinant molecule, referred to herein as pCro-nfSP33$_{1200}$, was transformed into *E. coli* BL-21 competent cells to form recombinant cell *E. coli*:pCro-nfSP33$_{1200}$. The recombinant cell was cultured using the method described above in Section A.

D. Flea serine protease protein PfSP40$_{242}$ was produced in the following manner. An about 716 bp nucleic acid molecule, referred to herein as nfSP40$_{716}$ (designed to encode an apparently mature serine protease protein) was PCR amplified from nfSP40$_{841}$ using sense primer Flea 40 EF having the nucleotide sequence 5' GCG GGA TCC AAT AGT AGG AGG TGA AGA TGT AG 3' (containing a BamHI-site; denoted SEQ ID NO:60) and anti-sense primer Flea 40 ER having the nucleotide sequence 5' CCG GAA TTC TTC TAA CAA ATT TTA TTT GAT TCC TGC 3' (containing a EcoRI; denoted SEQ ID NO:61). The resulting PCR product nfSP40$_{716}$ was digested with BamHI and EcoRI restriction endonucleases, gel purified, and subcloned into expression vector lambdaP$_R$/T$^2$ori/S10HIS-RSET-A9, that had been digested with BamHI and EcoRI and dephosphorylated. The resultant recombinant molecule, referred to herein as pCro-nfSP40$_{716}$, was transformed into *E. coli* BL-21 competent cells to form recombinant cell *E. coli*:pCro-nfSP40$_{716}$. The recombinant cell was cultured and protein production resolved using the methods described above in Section A. Immunoblot analysis of the proteins using a T7 antibody showed expression of an about 38 kD protein in the induced sample but not in the uninduced sample.

Example 12

This Example demonstrates the production of another serine protease protein of the present invention in *E. coli* cells.

A. Flea serine protease protein PfSP28$_{237}$ was produced in the following manner. An about 711 bp nucleic acid molecule, referred to herein as nfSP28$_{711}$ (designed to encode an apparently mature serine protease protein) was PCR amplified from nfSP28$_{923}$ using sense primer Flea 28 F having the nucleotide sequence 5' GGA TCC AAT CGT TGG AGG TGA AGA TG 3' (containing a BamHI-site shown in bold; denoted SEQ ID NO:62) and anti-sense primer Flea 28 R having the nucleotide sequence 5' GAA TTC GAA ATC CAC TTA AAC ATT AGC 3' (containing a EcoRI shown in bold; denoted SEQ ID NO:63). The resulting PCR product nfSP$_{711}$ was digested with BamHI and EcoRI restriction endonucleases, gel purified, and subcloned into expression vector lambdaP$_R$/T$^2$ori/S10HIS-RSET-A9, that had been digested with BamHI and XbaI and dephosphorylated. The resultant recombinant molecule, referred to herein as pCro-nfSP28$_{711}$, was transformed into *E. coli* BL-21 competent cells (available from Novagen, Madison, Wis.) to form recombinant cell *E. coli*:pCro-nfSP28$_{711}$. The recombinant cell was cultured and protein production resolved using the methods described above in Example 21. Immunoblot analysis of the proteins using a T7 antibody showed expression of an about 38 kD protein in the induced sample but not in the uninduced sample. Immunoblot analysis using a rabbit anti-flea midgut protease polyclonal antibody (the production of which is described in Example 14 of related PCT Publication NO.WO 95/24198) identified an about 38 kD protein in the induced sample.

Example 13

This Example demonstrates the production of another serine protease protein of the present invention in eukaryotic cells.

Recombinant molecule pBv-nfSP28$_{792}$, containing a flea serine protease nucleic acid molecule spanning nucleotides from about 11 through about 802 of SEQ ID NO:66, operatively linked to baculovirus polyhedron transcription control sequences were produced in the following manner. In order to subclone a flea serine protease nucleic acid molecule into a baculovirus expression vector, a flea serine protease nucleic acid molecule-containing fragment was PCR amplified from nfSP28$_{923}$. A PCR fragment of 792 nucleotides, named nfSP28$_{792}$, was amplified from nfSP28$_{923}$ using a sense primer Flea 28 F3 having the nucleic acid sequence 5' -GCG GGA TTC TAT AAA TAT GAA ACT TTT GGT AGT TTT TGC -3' (SEQ ID NO:62; BamHI site shown in bold) and an antisense primer Flea 28 R3 having the nucleic acid sequence 5' -GCT CTA GAC CAC TTA AAC ATT AGC ATA TTT TTC- 3' (SEQ ID NO:63; XbaI site shown in bold). The N-terminal primer was designed from the pol h sequence of baculovirus with modifications to enhance expression in the baculovirus system.

In order to produce a baculovirus recombinant molecule capable of directing the production of PfSP28$_{264}$, the about 792 base pair PCR product (referred to as Bv-nfSP28$_{792}$) was digested with BamHI and XbaI and subcloned into BamHI and XbaI digested to produce the recombinant molecule referred to herein as pVL-nfSP28$_{792}$.

The resultant recombinant molecule, pVL-nfSP28$_{792}$, was verified for proper insert orientation by restriction mapping. The recombinant molecule was co-transfected with a linear Baculogold baculovirus DNA (available from Pharmingen) into *S. frugiperda* Sf9 cells (available from Invitrogen) to form the recombinant cells denoted *S. frugiperda*:pVL-nfSP28$_{792}$. *S. frugiperda*:pVL-nfSP28$_{792}$ was cultured in order to produce a flea serine protease protein PfSP28$_{264}$.

Immunoblots of supernatants from cultures of *S. frugiperda*:pVL-nfSP28$_{792}$ cells producing the flea serine protease protein PfSP28$_{264}$ was performed using a cat anti-fSPFlea 28 polyclonal antibody which was produced as follows. Recombinant Flea 28 protein (referred to herein as rSPFlea 28 protein) produced in *E. coli* described above in Example 12 was used to immunize cats. The rSPFlea 28 protein was diluted to a concentration of about 1 mg/ml in PBS and emulsified in an equal volume of TiterMax research adjuvant (available from CytRx Corp., Norcross, Ga.). A series of cats were immunized each with about 50 µg of rSPFlea 28 protein in adjuvant by subcutaneous injection. A second injection of the same dose of rSPFlea 28 protein in adjuvant was administered 32 days later. Blood samples were obtained prior to immunization (pre-bleed), 32 days and 47 days after the initial immunization. Sera samples from the pre-immunization and Day 47 bleeds were used for subsequent immunoblot experiments. The latter is referred to as anti-fSPFlea 28 polyclonal antibody.

Analysis of the immunoblots identified an about 33 kD protein and an about 36 kD protein.

Example 14

This example describes the production of peptides from the 31 kD flea midgut serine protease and the generation of internal sequence data.

Midguts from about 30,000 cat blood-fed fleas were dissected as described in U.S. Pat. No. 5,356,622, ibid. in gut dissection buffer (50 mM Tris 8.0, 100 mM CaCl$_2$). The guts (in three batches of about 10,000 each) were disrupted by a freeze-thaw cycle, followed by sonication. The resulting extracts were clarified by centrifugation for 20 minutes at 3050 rpm in a swinging bucket centrifuge at 4° C. The supernatants were recovered, and adjusted to 400 mM NaCl in preparation for benzamidine column chromatography.

For each batch, gut supernatants were loaded into a 5 ml disposable column containing p-aminobenzamidine cross-linked to Sepharose beads (available from Sigma, St. Louis, Mo.), previously equilibrated in benzamidine column buffer (50 mM Tris, pH 8.0, 100 mM CaCl$_2$, 400 mM NaCl) and incubated with rocking overnight at 4° C. Unbound protein was slowly washed off the column using benzamidine column buffer until no protein was detectable by Bradford Assay (available from Bio-Rad Laboratories, Hercules, Calif.).

Proteases bound to the benzamidine column were eluted using 4 ml benzamidine column buffer supplemented with 100 mM p-aminobenzamidine (brought to pH 8.0 with NaOH). Residual bound proteases were washed off with about 21 ml of additional benzamidine column buffer. The recovered proteases were then concentrated to a volume of about 2 ml using a Ultrafree 20 10-kD centrifugal concentrator (available from Millipore, Bedford, Mass.). After concentration, the protease pools from the 3 preparations were combined for a total of about 30,000 gut equivalents in about 6 ml. Protein concentration was measured by Bradford assay and found to be about 0.5 mg/ml.

About 150 µg of the isolated protease pool was resolved by polyacrylamide gel electrophoresis (PAGE) on a preparative-well 14% Tris-glycine gel (available from Novex, San Diego, Calif.). After electrophoresis, the proteins in the gel were visualized by staining for about 30 minutes in Coomassie brilliant blue stain (0.1% (w/v) Coomassie blue R, 40% (v/v) methanol, 10% (v/v) acetic acid) and destaining for about 2.5 hours in 50% (v/v) methanol. The band corresponding to the 31-kD protease was excised with a razor blade. The protein was electroeluted, concentrated, and partially digested for 24 hours with cyanogen bromide (CNBr) (Silver, et al., 1995, *J. Biol. Chem.*, 270, 13010–13016), except that a small amount of acetic acid was added to the sample after electroelution and concentration to lower the sample pH and therefore reduce autodigestion by the 31-kD protease. CNBr is known to cleave after methionine (M) residues under the conditions used for this digestion. After CNBr digestion, the peptides in the sample were resolved by PAGE on an 18% Tris-glycine gel. After electrophoresis, the separated protease peptides were electroblotted onto a PVDF membrane using a CAPS buffer (10 mM CAPS pH 11, 0.5 mM DTT, 10% (v/v) methanol). The membrane was stained with Coomassie Brilliant Blue and destained with 50% (v/v) methanol. Three stained peptide bands were identified having apparent molecular weights of about 14 kD, 21 kD, and 22 kD, respectively. The portions of the membrane containing the 21 kD and 22 kD bands were excised separately. Peptides contained in each membrane segment were subjected to N-terminal amino acid sequencing using a 473A Protein Sequencer (available from Applied Biosystems, Foster City, Calif.) using standard techniques.

Although the results from the automated sequencing were difficult to interpret due to overlapping sequences, analysis of the chromatograms indicated the N-terminal amino acid sequence of the 21-kD peptide to be H/R-V/P-G/A/S-Y/G-E/N-D/K-V/R-D/A-D-Y -D-F-D/P-V-A, denoted herein as SEQ ID NO:70 and the N-terminal amino acid sequence of the 22-kD peptide to be I/Q-V-G-Y/G-E/N/T-D/M/P-V-K/D-I-N/S-M/T/N-F/C herein denoted as SEQ ID NO:71. The N-terminal amino acid sequence of the intact 31-kD protease is either I-V-G-G- E-D-V-D-I-S-T-C-G-W-C (SEQ ID NO:59, as disclosed in Example 34 in co-pending U.S. patent application Ser. No. 08/639,075), or IVGGEDVDIST(C)GWQI(S)FQ(S)ENLHF(C)GG(S)IIAPK (SEQ ID NO:69, as disclosed in Example 35 in co-pending U.S. patent application Ser. No. 08/639,075). These sequences vary at residue 15 in that SEQ ID NO:68 contains a cysteine and SEQ ID NO:69 contains a glutamine. These sequences can be identified in the sequences of both the 21-kD (SEQ ID NO:70) and 22-kD (SEQ ID NO:71) peptides, though it is much stronger in the 22-kD peptide, leading to the conclusion that the SEQ ID NO:71 represents the N-terminus of the 31-kD protease. If this sequence is subtracted from the sequence for the 21-kD (SEQ ID NO:70) peptide, then the resulting sequence for the 21-kD peptide is H/R-P-A/S-Y-N-K-R-A-D-Y-D-F-D-V-A, denoted herein as SEQ ID NO:72. This sequence of amino acids aligns with a stretch of deduced amino acids from about residue 107 to residue 121 immediately following a methionine residue in SEQ ID NO:67. These data confirm that the clone represented by nfSP28$_{923}$ (SEQ ID NO:66, as disclosed in Example 36 in co-pending U.S. patent application Ser. No. 08/639,075) indeed encodes the 31-kD protease.

Example 15

This example demonstrates that a 31-kD flea midgut serine protease contained in a formulation is able to proteolyze cat immunoglobulin G, A, and M proteins as well as bovine, dog, human, and rabbit immunoglobulin G proteins.

The 31-kD flea midgut serine protease was purified from cat blood-fed fleas as follows. Cat blood-fed flea midgut extracts were prepared and selected on a benzamidine column as described above in Example 25. The benzamidine eluate was then further purified as described in Example 35 of co-pending U.S. patent application Ser. No. 08/639,075 by PolyCAT A cation exchange chromatography (available from PolyLC, Inc., Columbia, Md.) to isolate a protein band which migrated at about 31 kD on a silver stained SDS-PAGE gel.

A. The ability of the cat blood-fed 31-kD flea midgut serine protease to degrade immunoglobulin was demonstrated by measuring digestion of immunoglobulin heavy chain using a method similar to that described in Example 35 of co-pending U.S. patent application Ser. No. 08/639,075. Specifically, 1 ug samples of cat IgG, cat IgA, and cat IgM substrates (available from Bethyl Laboratories, Inc., Montgomery, Tex.) were incubated with 500 cat blood-fed flea midgut equivalents of purified 31-kD flea midgut serine protease in a total volume of 27 ul 0.1M Tris-HCl pH 8.0 at 37° C. for 18 hours. The reaction mixtures were resolved by 14% Tris-glycine SDS-PAGE and the gel was silver stained using standard methods. The total disappearance (compared with control samples lacking addition of the purified 31-kD protein) of bands migrating at about 50, 60, and 80 kD on the silver stained gel in the lanes containing 31-kD protease-treated cat IgG, IgA, and IgM, respectively, indicated that the 31-kD flea midgut serine protease degraded the heavy chains of the various cat immunoglobulin isotypes.

B. The ability of the cat blood-fed 31-kD flea midgut serine protease to degrade IgG from several species was demonstrated by incubating 1 ug samples of purified cat or bovine IgG (purified from cat and bovine blood on Protein A Sepharose), or of purified dog, rabbit, or human IgG (each available from Sigma Chemical Co.) with 500 cat blood-fed flea midgut equivalents of the purified 31-kD flea midgut serine protease in a total volume of 27 ul 0.1M Tris-HCl pH 8.0 at 37° C. for 18 hours. The reaction mixtures were resolved by 14% Tris-glycine SDS-PAGE and the gel was silver stained using standard methods. The total disappearance (compared with control samples lacking addition of the purified 31-kD protein) of bands migrating at about 50–55-kD on the silver stained gel in the lanes containing the 31-kD protease treated cat, bovine, dog, rabbit, and human IgG heavy chains, indicated that the 31-kD flea midgut serine protease can degrade IgG from various mammalian species.

Example 16

This example describes the ability of a 31-kD flea midgut serine protease contained in a formulation to proteolyze cat immunoglobulin G at a specific site.

The 31-kD flea midgut serine protease was purified from cat blood-fed flea midgut extracts as described above in Examples 14 and 15

To investigate cleavage site specificity of the purified 31-kD flea midgut serine protease, 10 ug of cat immunoglobulin G purified from cat blood on Protein A sepharose was incubated with 200 cat blood-fed flea midgut equivalents of purified 31-kD flea midgut serine protease in a total volume of 100 ul 0.2 M Tris-HCl pH 8.0 at 37° C. for 18 hours. The reaction mixture was resolved by 14% Tris-glycine SDS-PAGE, blotted onto a PVDF membrane, stained with Coomassie R-250 and destained according to standard procedures. A band of about 33 kD was excised and subjected to N-terminal amino acid sequencing using techniques known to those skilled in the art. A partial N-terminal amino acid sequence of about 28 amino acids was determined and is represented herein as SEQ ID NO: 73: X-P-P-P-E-M-L-G-G-P-S-I-F-I-F-P-P-K-P-K-D-D-L-L-I-K-R-K. A GenBank homology search using SEQ ID NO:73 revealed most homology to *Oryctolagus caniculus* gamma H-chain constant region 2, there being about 71% identity over the 28 amino acids. Further alignments of SEQ ID NO:73 with sheep, rat, rabbit, monkey, bovine, and human IgG amino acid sequences indicated that the purified cat blood-fed 31-kD flea midgut serine protease cleaved the cat IgG heavy chain just before the predicted C-terminal end of the IgG hinge region. The predicted first amino acid cysteine and the second amino acid proline occur within the predicted hinge region while the remaining 26 amino acids of SEQ ID NO:73, starting with the third amino acid proline, occur within the predicted constant heavy chain-2 region.

The further investigate the cleavage site specificity of the purified 31-kD flea midgut serine protease for cat IgG, the cleavage site was compared to that of a known protease, papain, as follows. Cat immunoglobulin G (100 mg), purified from cat blood on Protein A sepharose, was incubated with 1 mg papain in l00mM sodium acetate pH 5.5, 50 mM cysteine, 1 mM EDTA in a final volume of 150 μl at room temperature for 4.5 hours. The reaction mixture was resolved on a 14!k Tris-glycine SDS-PAGE gel, blotted onto PVDF membrane, stained with Coomassie R-250 and destained according to standard procedures. A band of about 33 kD was excised and subjected to N-terminal amino acid sequencing using techniques known to those skilled in the art. A partial N-terminal amino acid sequence of about 25 amino acids was deduced and is represented herein as SEQ ID NO: 96: X-P-P-P-E-M-L-G-G-P-S-I-F-I-F-P-P-K-K-K-D-D-L-L-I. This sequence was nearly identical to the one obtained from a 33-kD cat IgG cleavage product generated by the purified 31-kD flea midgut serine protease, the only difference being the substitution of a lysine (SEQ ID NO:73) for a proline (SEQ ID NO:96) at amino acid 19.

Example 17

This Example demonstrates the kinetics of cat IgG degrading activity in the midguts of fleas fed on live cats.

A. To determine the kinetics of cat IgG degradation in the guts of continuously feeding fleas, female fleas contained in chambers were fed on seven separate cats (i.e. one chamber per cat) as described in Example 21 of co-pending U.S. patent application Ser. No. 08/639,075. Flea chambers were removed for dissections at timepoints of 15 min., 30 min., 1 hr., 2 hr., 4 hr., 6 hr., 8 hr., and 17 hr. After feeding on the cats, the fleas' midguts were removed as described in U.S. Pat. No. 5,356,622, ibid., homogenized by freeze-fracture and sonicated in a Tris buffer comprising 50 mM Tris, pH 8.0 and 100 mM $CaCl_2$. The extracts were centrifuged at about 14,000 xg for 20 min. and the soluble material recovered. The soluble material was then diluted to a final concentration of about 1.2 midgut equivalents per microliter ($\mu$l) of Tris buffer. The proteins contained in 1 midgut equivalent of each timepoint were then resolved by SDS-PAGE under reducing conditions, and the proteins visualized by silver staining. The results indicated that IgG heavy chain levels were significantly lower at the 17 hour time point than in the 8 hour and earlier time points, and that light chain levels were reduced but not to the same extent as the heavy chain. The proteins contained in 5 gut equivalents of each timepoint were then resolved by SDS-PAGE gel under reducing conditions and were subjected to western blot analysis using alkaline phosphatase labeled goat anti-cat IgG (heavy plus light chain) antibody (available from Kirkegaard and Perry Laboratories, Gaithersburg, Md.). The results indicated that cat IgG heavy chain was present in the midguts of continuously feeding fleas for at least 8 hours, but was not detected in the midguts of fleas allowed to feed continuously on a cat for 17 hours. Light chain was visible in all samples, though the amount visible in the 17 hour sample was significantly less than that visible in the 8 hour sample. These results suggest that even when fleas are continuously feeding on a cat, the levels of IgG-degrading proteases induced in the flea midguts at a time point of 17 hours is sufficient to degrade all detectable cat IgG ingested. These results suggest that when fleas are continuously feeding on a cat, the levels of IgG-degrading proteases induced in the flea midguts are not sufficient to degrade all detectable cat IgG ingested for at least 8 hours.

B. To determine the kinetics of cat IgG degradation in the guts of fleas fed for a specified time then removed from the cat, fleas (in chambers) were fed on cats as in Section A for periods of either 1 hour or 24 hours. Following the 1 or 24-hour feeding periods, the flea chambers were removed and placed in a 28° C., 75% relative humidity growth incubator. Fleas were subjected to dissection at time points of 0, 1, 2, 4, and 8 hr. following removal from the cats. Midguts were homogenized, and the midgut contents were examined by silver stained SDS-PAGE and immunoblot analysis, as described in Section A. The fleas fed for 1 hour had high molecular weight proteins, including the heavy chain and light chain of cat IgG detectable in their midguts at the 0 and 1 hour dissection timepoints, while the flea midguts evaluated at time points of 2 hours or greater had no detectable IgG heavy chain bands. The results showed that when fleas were fed on a cat and then removed, they degraded the ingested cat IgG heavy chain nearly completely within 2 hours. The fleas fed on cats for 24 hours had no detectable IgG heavy or light chain proteins in midgut extracts at any of the timepoints. These results suggest that when no new cat IgG is ingested, as is the case when the fleas are removed from feeding, that the IgG-degrading proteases in the flea midgut fully degraded all cat IgG heavy chain in less than two hours.

SEQUENCE LISTING (1) GENERAL INFORMATION:

(iii) NUMBER OF SEQUENCES: 103

(2) INFORMATION FOR SEQ ID NO:1:

(i) SEQUENCE CHARACTERISTICS:
      (A) LENGTH: 1109 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 126..1106

(xi) SEQUENCE DESCRIPTION: SEQ ID NO:1:

TACAATTAGG GTGACGATCT TTTAGACAAG CGAAATTGAT AACGAAGTTT TCGAAGTCGG    60

-continued

```
ATGAAGTAAA AACCTTGCGT TGGTTTCCCC GGTCCCAGGA TCAGGAACAG TTGCACTTTA         120

CCCCA ATG AGG GAA TTC GTG CAT CCC CAT TTT ACC GAA CAT ATT GAT             167
      Met Arg Glu Phe Val His Pro His Phe Thr Glu His Ile Asp
      1               5                   10

GAA GAA TTC CAC CGA TTC ATC AAT AAA CAC GGA AAA ATT TAT AAT AAA           215
Glu Glu Phe His Arg Phe Ile Asn Lys His Gly Lys Ile Tyr Asn Lys
15                  20                  25                  30

AAT GAA GAA CAT CAT TTC CGC AAA GAA ATT TTC AGA CTA AAC TTG AGG           263
Asn Glu Glu His His Phe Arg Lys Glu Ile Phe Arg Leu Asn Leu Arg
                35                  40                  45

TAC ATT TTT TCT AAG AAT CGT GCA AAT TTG GGA TAC ACT TTG ACT GTT           311
Tyr Ile Phe Ser Lys Asn Arg Ala Asn Leu Gly Tyr Thr Leu Thr Val
                50                  55                  60

AAC CAT TTG GCT GAT CGT ACT GAA GCT GAA CTT AAG GCT TTG AGA GGA           359
Asn His Leu Ala Asp Arg Thr Glu Ala Glu Leu Lys Ala Leu Arg Gly
                65                  70                  75

CAC AGA CCT TCC TCC GGT TAT AAT GGC GGT TTA CCC TTT CCT CAC AAT           407
His Arg Pro Ser Ser Gly Tyr Asn Gly Gly Leu Pro Phe Pro His Asn
        80                  85                  90

ACC ACC AAG GAA GCA AGA AAT TTA CCA GAT TCT TTC GAC TGG CGA ATT           455
Thr Thr Lys Glu Ala Arg Asn Leu Pro Asp Ser Phe Asp Trp Arg Ile
95                  100                 105                 110

TAT GGA GCT GTT ACT CCA GTT AAA GAT CAA TCT GTT TGT GGT TCC TGC           503
Tyr Gly Ala Val Thr Pro Val Lys Asp Gln Ser Val Cys Gly Ser Cys
                115                 120                 125

TGG TCT TTC GGA ACA ATT GGA GCA ATC GAA GGT GCA TAT TTC TTG AAA           551
Trp Ser Phe Gly Thr Ile Gly Ala Ile Glu Gly Ala Tyr Phe Leu Lys
                130                 135                 140

AAC GGC GGT AAT CTT GTA CGA TTG TCT CAA CAG GCT TTG ATT GAT TGT           599
Asn Gly Gly Asn Leu Val Arg Leu Ser Gln Gln Ala Leu Ile Asp Cys
                145                 150                 155

TCT TGG GGA TAT GGA AAT AAT GGT TGC GAC GGT GGC GAA GAT TTC CGC           647
Ser Trp Gly Tyr Gly Asn Asn Gly Cys Asp Gly Gly Glu Asp Phe Arg
        160                 165                 170

GCC TAC CAA TGG ATG ATG AAA CAT GGA GGA ATC CCT ACT GAA GAG GAT           695
Ala Tyr Gln Trp Met Met Lys His Gly Gly Ile Pro Thr Glu Glu Asp
175                 180                 185                 190

TAT GGT GGT TAC TTG GGA CAA GAT GGT TAC TGC CAT GTC AAC AAC GTT           743
Tyr Gly Gly Tyr Leu Gly Gln Asp Gly Tyr Cys His Val Asn Asn Val
                195                 200                 205

ACT TTA GTT GCT CCC ATC ACA GGA TAT GTC AAC GTA ACT CGT AAC GAT           791
Thr Leu Val Ala Pro Ile Thr Gly Tyr Val Asn Val Thr Arg Asn Asp
                210                 215                 220

GTT GAC GCT ATG AAG GTT GCC CTT CTT AAA CAC GGT CCG ATT TCG GTG           839
Val Asp Ala Met Lys Val Ala Leu Leu Lys His Gly Pro Ile Ser Val
                225                 230                 235

GCC ATT GAC GCA TCA CAC AAA ACA TCC AGT TTT TAC TCC AAC GGC GTT           887
Ala Ile Asp Ala Ser His Lys Thr Ser Ser Phe Tyr Ser Asn Gly Val
240                 245                 250

TAC TAC CAA CCG AAA TGT GGC AAT AAA AGA GGA CAA TTA GAC CAC GCC           935
Tyr Tyr Gln Pro Lys Cys Gly Asn Lys Arg Gly Gln Leu Asp His Ala
255                 260                 265                 270

GTA TTA GTA GTC GGT TAT GGT GAA ATC AAC AGC GAA CCT TAC TGG TTG           983
Val Leu Val Val Gly Tyr Gly Glu Ile Asn Ser Glu Pro Tyr Trp Leu
                275                 280                 285

GTC AAG AAT CCT GGT CAA TTG TGG GGA AAC AAT GTT ATA TTT GAT GTC           1031
Val Lys Asn Pro Gly Gln Leu Trp Gly Asn Asn Val Ile Phe Asp Val
                290                 295                 300

GCC AAA AAT AAT AAT GCG GAT TTG ACG ATC ACT TAT TTA CTA TGT ACT           1079
Ala Lys Asn Asn Asn Ala Asp Leu Thr Ile Thr Tyr Leu Leu Cys Thr
```

```
Ala Lys Asn Asn Asn Ala Asp Leu Thr Ile Thr Tyr Leu Leu Cys Thr
        305                 310                 315
ACT TTT AAA ATT GAT TTT TAC GGC ATG TAA                              1109
Thr Phe Lys Ile Asp Phe Tyr Gly Met
    320                 325
```

(2) INFORMATION FOR SEQ ID NO:2:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Glu Phe Val His Pro His Phe Thr Glu His Ile Asp Glu Glu
  1               5                  10                  15

Phe His Arg Phe Ile Asn Lys His Gly Lys Ile Tyr Asn Lys Asn Glu
             20                  25                  30

Glu His His Phe Arg Lys Glu Ile Phe Arg Leu Asn Leu Arg Tyr Ile
         35                  40                  45

Phe Ser Lys Asn Arg Ala Asn Leu Gly Tyr Thr Leu Thr Val Asn His
     50                  55                  60

Leu Ala Asp Arg Thr Glu Ala Glu Leu Lys Ala Leu Arg Gly His Arg
 65                  70                  75                  80

Pro Ser Ser Gly Tyr Asn Gly Leu Pro Phe Pro His Asn Thr Thr
                 85                  90                  95

Lys Glu Ala Arg Asn Leu Pro Asp Ser Phe Asp Trp Arg Ile Tyr Gly
                100                 105                 110

Ala Val Thr Pro Val Lys Asp Gln Ser Val Cys Gly Ser Cys Trp Ser
            115                 120                 125

Phe Gly Thr Ile Gly Ala Ile Glu Gly Ala Tyr Phe Leu Lys Asn Gly
        130                 135                 140

Gly Asn Leu Val Arg Leu Ser Gln Gln Ala Leu Ile Asp Cys Ser Trp
145                 150                 155                 160

Gly Tyr Gly Asn Asn Gly Cys Asp Gly Gly Glu Asp Phe Arg Ala Tyr
                165                 170                 175

Gln Trp Met Met Lys His Gly Ile Pro Thr Glu Glu Asp Tyr Gly
            180                 185                 190

Gly Tyr Leu Gly Gln Asp Gly Tyr Cys His Val Asn Asn Val Thr Leu
        195                 200                 205

Val Ala Pro Ile Thr Gly Tyr Val Asn Val Thr Arg Asn Asp Val Asp
    210                 215                 220

Ala Met Lys Val Ala Leu Leu Lys His Gly Pro Ile Ser Val Ala Ile
225                 230                 235                 240

Asp Ala Ser His Lys Thr Ser Ser Phe Tyr Ser Asn Gly Val Tyr Tyr
                245                 250                 255

Gln Pro Lys Cys Gly Asn Lys Arg Gly Gln Leu Asp His Ala Val Leu
            260                 265                 270

Val Val Gly Tyr Gly Glu Ile Asn Ser Glu Pro Tyr Trp Leu Val Lys
        275                 280                 285

Asn Pro Gly Gln Leu Trp Gly Asn Asn Val Ile Phe Asp Val Ala Lys
    290                 295                 300

Asn Asn Asn Ala Asp Leu Thr Ile Thr Tyr Leu Leu Cys Thr Thr Phe
305                 310                 315                 320
```

Lys Ile Asp Phe Tyr Gly Met
              325

(2) INFORMATION FOR SEQ ID NO:3:

(i) SEQUENCE CHARACTERISTICS:
        (A) LENGTH: 1109 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TTACATGCCG TAAAAATCAA TTTTAAAAGT AGTACATAGT AAATAAGTGA TCGTCAAATC      60
CGCATTATTA TTTTTGGCGA CATCAAATAT AACATTGTTT CCCCACAATT GACCAGGATT     120
CTTGACCAAC CAGTAAGGTT CGCTGTTGAT TCACCATAA CCGACTACTA ATACGGCGTG      180
GTCTAATTGT CCTCTTTTAT TGCCACATTT CGGTTGGTAG TAAACGCCGT TGGAGTAAAA     240
ACTGGATGTT TTGTGTGATG CGTCAATGGC CACCGAAATC GGACCGTGTT TAAGAAGGGC     300
AACCTTCATA GCGTCAACAT CGTTACGAGT TACGTTGACA TATCCTGTGA TGGGAGCAAC     360
TAAAGTAACG TTGTTGACAT GGCAGTAACC ATCTTGTCCC AAGTAACCAC CATAATCCTC     420
TTCAGTAGGG ATTCCTCCAT GTTTCATCAT CCATTGGTAG GCGCGGAAAT CTTCGCCACC     480
GTCGCAACCA TTATTTCCAT ATCCCCAAGA ACAATCAATC AAAGCCTGTT GAGACAATCG     540
TACAAGATTA CCGCCGTTTT TCAAGAAATA TGCACCTTCG ATTGCTCCAA TTGTTCCGAA     600
AGACCAGCAG GAACCACAAA CAGATTGATC TTTAACTGGA GTAACAGCTC CATAAATTCG     660
CCAGTCGAAA GAATCTGGTA AATTTCTTGC TTCCTTGGTG GTATTGTGAG GAAAGGGTAA     720
ACCGCCATTA TAACCGGAGG AAGGTCTGTG TCCTCTCAAA GCCTTAAGTT CAGCTTCAGT     780
ACGATCAGCC AAATGGTTAA CAGTCAAAGT GTATCCCAAA TTTGCACGAT TCTTAGAAAA     840
AATGTACCTC AAGTTTAGTC TGAAAATTTC TTTGCGGAAA TGATGTTCTT CATTTTTATT     900
ATAAATTTTT CCGTGTTTAT TGATGAATCG GTGGAATTCT TCATCAATAT GTTCGGTAAA     960
ATGGGGATGC ACGAATTCCC TCATTGGGGT AAAGTGCAAC TGTTCCTGAT CCTGGGACCG    1020
GGGAAACCAA CGCAAGGTTT TTACTTCATC CGACTTCGAA AACTTCGTTA TCAATTTCGC    1080
TTGTCTAAAA GATCGTCACC CTAATTGTA                                     1109
```

(2) INFORMATION FOR SEQ ID NO:4:

(i) SEQUENCE CHARACTERISTICS:
        (A) LENGTH: 984 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..981

(xi) SEQUENCE DESCRIPTION: SEQ ID NO:4:

```
ATG AGG GAA TTC GTG CAT CCC CAT TTT ACC GAA CAT ATT GAT GAA GAA       48
Met Arg Glu Phe Val His Pro His Phe Thr Glu His Ile Asp Glu Glu
  1               5                  10                  15

TTC CAC CGA TTC ATC AAT AAA CAC GGA AAA ATT TAT AAT AAA AAT GAA       96
Phe His Arg Phe Ile Asn Lys His Gly Lys Ile Tyr Asn Lys Asn Glu
             20                  25                  30
```

```
GAA CAT CAT TTC CGC AAA GAA ATT TTC AGA CTA AAC TTG AGG TAC ATT        144
Glu His His Phe Arg Lys Glu Ile Phe Arg Leu Asn Leu Arg Tyr Ile
        35                  40                  45

TTT TCT AAG AAT CGT GCA AAT TTG GGA TAC ACT TTG ACT GTT AAC CAT        192
Phe Ser Lys Asn Arg Ala Asn Leu Gly Tyr Thr Leu Thr Val Asn His
 50                  55                  60

TTG GCT GAT CGT ACT GAA GCT GAA CTT AAG GCT TTG AGA GGA CAC AGA        240
Leu Ala Asp Arg Thr Glu Ala Glu Leu Lys Ala Leu Arg Gly His Arg
 65                  70                  75                  80

CCT TCC TCC GGT TAT AAT GGC GGT TTA CCC TTT CCT CAC AAT ACC ACC        288
Pro Ser Ser Gly Tyr Asn Gly Gly Leu Pro Phe Pro His Asn Thr Thr
                 85                  90                  95

AAG GAA GCA AGA AAT TTA CCA GAT TCT TTC GAC TGG CGA ATT TAT GGA        336
Lys Glu Ala Arg Asn Leu Pro Asp Ser Phe Asp Trp Arg Ile Tyr Gly
            100                 105                 110

GCT GTT ACT CCA GTT AAA GAT CAA TCT GTT TGT GGT TCC TGC TGG TCT        384
Ala Val Thr Pro Val Lys Asp Gln Ser Val Cys Gly Ser Cys Trp Ser
            115                 120                 125

TTC GGA ACA ATT GGA GCA ATC GAA GGT GCA TAT TTC TTG AAA AAC GGC        432
Phe Gly Thr Ile Gly Ala Ile Glu Gly Ala Tyr Phe Leu Lys Asn Gly
130                 135                 140

GGT AAT CTT GTA CGA TTG TCT CAA CAG GCT TTG ATT GAT TGT TCT TGG        480
Gly Asn Leu Val Arg Leu Ser Gln Gln Ala Leu Ile Asp Cys Ser Trp
145                 150                 155                 160

GGA TAT GGA AAT AAT GGT TGC GAC GGT GGC GAA GAT TTC CGC GCC TAC        528
Gly Tyr Gly Asn Asn Gly Cys Asp Gly Gly Glu Asp Phe Arg Ala Tyr
                165                 170                 175

CAA TGG ATG ATG AAA CAT GGA GGA ATC CCT ACT GAA GAG GAT TAT GGT        576
Gln Trp Met Met Lys His Gly Gly Ile Pro Thr Glu Glu Asp Tyr Gly
            180                 185                 190

GGT TAC TTG GGA CAA GAT GGT TAC TGC CAT GTC AAC AAC GTT ACT TTA        624
Gly Tyr Leu Gly Gln Asp Gly Tyr Cys His Val Asn Asn Val Thr Leu
            195                 200                 205

GTT GCT CCC ATC ACA GGA TAT GTC AAC GTA ACT CGT AAC GAT GTT GAC        672
Val Ala Pro Ile Thr Gly Tyr Val Asn Val Thr Arg Asn Asp Val Asp
            210                 215                 220

GCT ATG AAG GTT GCC CTT CTT AAA CAC GGT CCG ATT TCG GTG GCC ATT        720
Ala Met Lys Val Ala Leu Leu Lys His Gly Pro Ile Ser Val Ala Ile
225                 230                 235                 240

GAC GCA TCA CAC AAA ACA TCC AGT TTT TAC TCC AAC GGC GTT TAC TAC        768
Asp Ala Ser His Lys Thr Ser Ser Phe Tyr Ser Asn Gly Val Tyr Tyr
                245                 250                 255

CAA CCG AAA TGT GGC AAT AAA AGA GGA CAA TTA GAC CAC GCC GTA TTA        816
Gln Pro Lys Cys Gly Asn Lys Arg Gly Gln Leu Asp His Ala Val Leu
            260                 265                 270

GTA GTC GGT TAT GGT GAA ATC AAC AGC GAA CCT TAC TGG TTG GTC AAG        864
Val Val Gly Tyr Gly Glu Ile Asn Ser Glu Pro Tyr Trp Leu Val Lys
            275                 280                 285

AAT CCT GGT CAA TTG TGG GGA AAC AAT GTT ATA TTT GAT GTC GCC AAA        912
Asn Pro Gly Gln Leu Trp Gly Asn Asn Val Ile Phe Asp Val Ala Lys
290                 295                 300

AAT AAT AAT GCG GAT TTG ACG ATC ACT TAT TTA CTA TGT ACT ACT TTT        960
Asn Asn Asn Ala Asp Leu Thr Ile Thr Tyr Leu Leu Cys Thr Thr Phe
305                 310                 315                 320

AAA ATT GAT TTT TAC GGC ATG TAA                                        984
Lys Ile Asp Phe Tyr Gly Met
                325
```

(2) INFORMATION FOR SEQ ID NO:5:

-continued

```
    (i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:5:

Met Arg Glu Phe Val His Pro His Phe Thr Glu His Ile Asp Glu Glu
  1               5                  10                  15

Phe His Arg Phe Ile Asn Lys His Gly Lys Ile Tyr Asn Lys Asn Glu
             20                  25                  30

Glu His His Phe Arg Lys Glu Ile Phe Arg Leu Asn Leu Arg Tyr Ile
         35                  40                  45

Phe Ser Lys Asn Arg Ala Asn Leu Gly Tyr Thr Leu Thr Val Asn His
 50                  55                  60

Leu Ala Asp Arg Thr Glu Ala Glu Leu Lys Ala Leu Arg Gly His Arg
 65                  70                  75                  80

Pro Ser Ser Gly Tyr Asn Gly Leu Pro Phe Pro His Asn Thr Thr
                 85                  90                  95

Lys Glu Ala Arg Asn Leu Pro Asp Ser Phe Asp Trp Arg Ile Tyr Gly
            100                 105                 110

Ala Val Thr Pro Val Lys Asp Gln Ser Val Cys Gly Ser Cys Trp Ser
            115                 120                 125

Phe Gly Thr Ile Gly Ala Ile Glu Gly Ala Tyr Phe Leu Lys Asn Gly
130                 135                 140

Gly Asn Leu Val Arg Leu Ser Gln Gln Ala Leu Ile Asp Cys Ser Trp
145                 150                 155                 160

Gly Tyr Gly Asn Asn Gly Cys Asp Gly Gly Glu Asp Phe Arg Ala Tyr
                165                 170                 175

Gln Trp Met Met Lys His Gly Gly Ile Pro Thr Glu Glu Asp Tyr Gly
            180                 185                 190

Gly Tyr Leu Gly Gln Asp Gly Tyr Cys His Val Asn Asn Val Thr Leu
            195                 200                 205

Val Ala Pro Ile Thr Gly Tyr Val Asn Val Thr Arg Asn Asp Val Asp
            210                 215                 220

Ala Met Lys Val Ala Leu Leu Lys His Gly Pro Ile Ser Val Ala Ile
225                 230                 235                 240

Asp Ala Ser His Lys Thr Ser Ser Phe Tyr Ser Asn Gly Val Tyr Tyr
                245                 250                 255

Gln Pro Lys Cys Gly Asn Lys Arg Gly Gln Leu Asp His Ala Val Leu
            260                 265                 270

Val Val Gly Tyr Gly Glu Ile Asn Ser Glu Pro Tyr Trp Leu Val Lys
            275                 280                 285

Asn Pro Gly Gln Leu Trp Gly Asn Asn Val Ile Phe Asp Val Ala Lys
            290                 295                 300

Asn Asn Asn Ala Asp Leu Thr Ile Thr Tyr Leu Leu Cys Thr Thr Phe
305                 310                 315                 320

Lys Ile Asp Phe Tyr Gly Met
                325

(2) INFORMATION FOR SEQ ID NO:6:

(i) SEQUENCE CHARACTERISTICS:
        (A) LENGTH: 981 base pairs
        (B) TYPE: nucleic acid
        (C) STRANDEDNESS: single
```

-continued (D) TOPOLOGY: linear (ii) MOLECULE TYPE: DNA (genomic)

(xi) SEQUENCE DESCRIPTION: SEQ ID NO:6:

| | | | | | |
|---|---|---|---|---|---|
| CATGCCGTAA | AAATCAATTT | TAAAAGTAGT | ACATAGTAAA | TAAGTGATCG | TCAAATCCGC | 60 |
| ATTATTATTT | TTGGCGACAT | CAAATATAAC | ATTGTTTCCC | CACAATTGAC | CAGGATTCTT | 120 |
| GACCAACCAG | TAAGGTTCGC | TGTTGATTTC | ACCATAACCG | ACTACTAATA | CGGCGTGGTC | 180 |
| TAATTGTCCT | CTTTTATTGC | CACATTTCGG | TTGGTAGTAA | ACGCCGTTGG | AGTAAAAACT | 240 |
| GGATGTTTTG | TGTGATGCGT | CAATGGCCAC | CGAAATCGGA | CCGTGTTTAA | GAAGGGCAAC | 300 |
| CTTCATAGCG | TCAACATCGT | TACGAGTTAC | GTTGACATAT | CCTGTGATGG | GAGCAACTAA | 360 |
| AGTAACGTTG | TTGACATGGC | AGTAACCATC | TTGTCCCAAG | TAACCACCAT | AATCCTCTTC | 420 |
| AGTAGGGATT | CCTCCATGTT | TCATCATCCA | TTGGTAGGCG | CGGAAATCTT | CGCCACCGTC | 480 |
| GCAACCATTA | TTTCCATATC | CCCAAGAACA | ATCAATCAAA | GCCTGTTGAG | ACAATCGTAC | 540 |
| AAGATTACCG | CCGTTTTTCA | AGAAATATGC | ACCTTCGATT | GCTCCAATTG | TTCCGAAAGA | 600 |
| CCAGCAGGAA | CCACAAACAG | ATTGATCTTT | AACTGGAGTA | ACAGCTCCAT | AAATTCGCCA | 660 |
| GTCGAAAGAA | TCTGGTAAAT | TTCTTGCTTC | CTTGGTGGTA | TTGTGAGGAA | AGGGTAAACC | 720 |
| GCCATTATAA | CCGGAGGAAG | GTCTGTGTCC | TCTCAAAGCC | TTAAGTTCAG | CTTCAGTACG | 780 |
| ATCAGCCAAA | TGGTTAACAG | TCAAAGTGTA | TCCCAAATTT | GCACGATTCT | TAGAAAAAAT | 840 |
| GTACCTCAAG | TTTAGTCTGA | AAATTTCTTT | GCGGAAATGA | TGTTCTTCAT | TTTTATTATA | 900 |
| AATTTTTCCG | TGTTTATTGA | TGAATCGGTG | GAATTCTTCA | TCAATATGTT | CGGTAAAATG | 960 |
| GGGATGCACG | AATTCCCTCA | T | | | | 981 |

(2) INFORMATION FOR SEQ ID NO:7:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..678

(xi) SEQUENCE DESCRIPTION: SEQ ID NO:7:

```
TTA CCA GAT TCT TTC GAC TGG CGA ATT TAT GGA GCT GTT ACT CCA GTT       48
Leu Pro Asp Ser Phe Asp Trp Arg Ile Tyr Gly Ala Val Thr Pro Val
 1               5                  10                  15

AAA GAT CAA TCT GTT TGT GGT TCC TGC TGG TCT TTC GGA ACA ATT GGA       96
Lys Asp Gln Ser Val Cys Gly Ser Cys Trp Ser Phe Gly Thr Ile Gly
                20                  25                  30

GCA ATC GAA GGT GCA TAT TTC TTG AAA AAC GGC GGT AAT CTT GTA CGA      144
Ala Ile Glu Gly Ala Tyr Phe Leu Lys Asn Gly Gly Asn Leu Val Arg
            35                  40                  45

TTG TCT CAA CAG GCT TTG ATT GAT TGT TCT TGG GGA TAT GGA AAT AAT      192
Leu Ser Gln Gln Ala Leu Ile Asp Cys Ser Trp Gly Tyr Gly Asn Asn
        50                  55                  60

GGT TGC GAC GGT GGC GAA GAT TTC CGC GCC TAC CAA TGG ATG ATG AAA      240
Gly Cys Asp Gly Gly Glu Asp Phe Arg Ala Tyr Gln Trp Met Met Lys
65                  70                  75                  80

CAT GGA GGA ATC CCT ACT GAA GAG GAT TAT GGT GGT TAC TTG GGA CAA      288
His Gly Gly Ile Pro Thr Glu Glu Asp Tyr Gly Gly Tyr Leu Gly Gln
```

```
                    85                  90                  95
GAT GGT TAC TGC CAT GTC AAC AAC GTT ACT TTA GTT GCT CCC ATC ACA        336
Asp Gly Tyr Cys His Val Asn Asn Val Thr Leu Val Ala Pro Ile Thr
                100                 105                 110

GGA TAT GTC AAC GTA ACT CGT AAC GAT GTT GAC GCT ATG AAG GTT GCC        384
Gly Tyr Val Asn Val Thr Arg Asn Asp Val Asp Ala Met Lys Val Ala
            115                 120                 125

CTT CTT AAA CAC GGT CCG ATT TCG GTG GCC ATT GAC GCA TCA CAC AAA        432
Leu Leu Lys His Gly Pro Ile Ser Val Ala Ile Asp Ala Ser His Lys
        130                 135                 140

ACA TCC AGT TTT TAC TCC AAC GGC GTT TAC TAC CAA CCG AAA TGT GGC        480
Thr Ser Ser Phe Tyr Ser Asn Gly Val Tyr Tyr Gln Pro Lys Cys Gly
145                 150                 155                 160

AAT AAA AGA GGA CAA TTA GAC CAC GCC GTA TTA GTA GTC GGT TAT GGT        528
Asn Lys Arg Gly Gln Leu Asp His Ala Val Leu Val Val Gly Tyr Gly
                165                 170                 175

GAA ATC AAC AGC GAA CCT TAC TGG TTG GTC AAG AAT CCT GGT CAA TTG        576
Glu Ile Asn Ser Glu Pro Tyr Trp Leu Val Lys Asn Pro Gly Gln Leu
            180                 185                 190

TGG GGA AAC AAT GTT ATA TTT GAT GTC GCC AAA AAT AAT AAT GCG GAT        624
Trp Gly Asn Asn Val Ile Phe Asp Val Ala Lys Asn Asn Asn Ala Asp
        195                 200                 205

TTG ACG ATC ACT TAT TTA CTA TGT ACT ACT TTT AAA ATT GAT TTT TAC        672
Leu Thr Ile Thr Tyr Leu Leu Cys Thr Thr Phe Lys Ile Asp Phe Tyr
210                 215                 220

GGC ATG TAA                                                             681
Gly Met
225
```

(2) INFORMATION FOR SEQ ID NO:8:

(i) SEQUENCE CHARACTERISTICS:
        (A) LENGTH: 226 amino acids
        (B) TYPE: amino acid
        (D) TOPOLOGY: linear (ii) MOLECULE TYPE: protein (xi) SEQUENCE DESCRIPTION: SEQ ID NO:8:

```
Leu Pro Asp Ser Phe Asp Trp Arg Ile Tyr Gly Ala Val Thr Pro Val
 1               5                  10                  15

Lys Asp Gln Ser Val Cys Gly Ser Cys Trp Ser Phe Gly Thr Ile Gly
                20                  25                  30

Ala Ile Glu Gly Ala Tyr Phe Leu Lys Asn Gly Gly Asn Leu Val Arg
            35                  40                  45

Leu Ser Gln Gln Ala Leu Ile Asp Cys Ser Trp Gly Tyr Gly Asn Asn
        50                  55                  60

Gly Cys Asp Gly Gly Glu Asp Phe Arg Ala Tyr Gln Trp Met Met Lys
65                  70                  75                  80

His Gly Gly Ile Pro Thr Glu Glu Asp Tyr Gly Gly Tyr Leu Gly Gln
                85                  90                  95

Asp Gly Tyr Cys His Val Asn Asn Val Thr Leu Val Ala Pro Ile Thr
                100                 105                 110

Gly Tyr Val Asn Val Thr Arg Asn Asp Val Asp Ala Met Lys Val Ala
            115                 120                 125

Leu Leu Lys His Gly Pro Ile Ser Val Ala Ile Asp Ala Ser His Lys
        130                 135                 140

Thr Ser Ser Phe Tyr Ser Asn Gly Val Tyr Tyr Gln Pro Lys Cys Gly
145                 150                 155                 160
```

```
Asn Lys Arg Gly Gln Leu Asp His Ala Val Leu Val Gly Tyr Gly
            165                 170                 175

Glu Ile Asn Ser Glu Pro Tyr Trp Leu Val Lys Asn Pro Gly Gln Leu
            180                 185                 190

Trp Gly Asn Asn Val Ile Phe Asp Val Ala Lys Asn Asn Ala Asp
            195                 200                 205

Leu Thr Ile Thr Tyr Leu Leu Cys Thr Thr Phe Lys Ile Asp Phe Tyr
            210                 215                 220

Gly Met
225
```

(2) INFORMATION FOR SEQ ID NO:9:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..685

(ix) FEATURE:
        (A) NAME/KEY: Xaa = any amino acid
        (B) LOCATION: 187

(xi) SEQUENCE DESCRIPTION: SEQ ID NO:9:

```
TCA AAT CGG ATT GTT AAT GGA GTT AAT GCC AAA AAC GGT TCT GCT CCA      48
Ser Asn Arg Ile Val Asn Gly Val Asn Ala Lys Asn Gly Ser Ala Pro
 1               5                  10                  15

TAT ATG GCT TCT CTA AGA GAT GTT ATG GAA ACC ATT TCT GTG GAG CAT      96
Tyr Met Ala Ser Leu Arg Asp Val Met Glu Thr Ile Ser Val Glu His
                20                  25                  30

CGA TAT TGG ATG AAC CGC TGG ATT CTT ACT GCT GCC CAT TGC CTT ACT     144
Arg Tyr Trp Met Asn Arg Trp Ile Leu Thr Ala Ala His Cys Leu Thr
             35                  40                  45

GAC GGT TAT CTA GAT ACA GTC TAC GTT GGT TCA AAT CAT CTT TCT GGC     192
Asp Gly Tyr Leu Asp Thr Val Tyr Val Gly Ser Asn His Leu Ser Gly
 50                  55                  60

GAC GGA GAG TAC TAC AAT GTA GAA GAA CAA GTC ATC CAT GAT AAA TAT     240
Asp Gly Glu Tyr Tyr Asn Val Glu Glu Gln Val Ile His Asp Lys Tyr
 65                  70                  75                  80

TTT GGT CAA ACA ACC GGC TTC AAA AAT GAT ATT GCT CTC GTC AAA GTT     288
Phe Gly Gln Thr Thr Gly Phe Lys Asn Asp Ile Ala Leu Val Lys Val
                 85                  90                  95

TCT AGT GCT ATA AAA CTT AGC AAA AAT GTT CGT CCC ATC AAA TTG CAC     336
Ser Ser Ala Ile Lys Leu Ser Lys Asn Val Arg Pro Ile Lys Leu His
                100                 105                 110

AAA GAT TTT ATA CGC GGA GGT GAA AAA TTG AAA ATT ACT GGA TGG GGA     384
Lys Asp Phe Ile Arg Gly Gly Glu Lys Leu Lys Ile Thr Gly Trp Gly
            115                 120                 125

TTG ACC AAT CAA ACT CAT GGT GAA GTT CCT GAT GCT CTT CAA GAG TTA     432
Leu Thr Asn Gln Thr His Gly Glu Val Pro Asp Ala Leu Gln Glu Leu
130                 135                 140

CAG GTA GAA GCA CTT TCT AAC TCT AAA TGC AAG GCA ATT ACT GGT GTC     480
Gln Val Glu Ala Leu Ser Asn Ser Lys Cys Lys Ala Ile Thr Gly Val
145                 150                 155                 160

CAT CTT CCT GCT CAT CTC TGC ACC TTC AAA GCA CCT CAA AAG GGT GTA     528
His Leu Pro Ala His Leu Cys Thr Phe Lys Ala Pro Gln Lys Gly Val
```

-continued

```
              165                 170                 175
TGC ATG GGT GAC TCT GGT GGT CCT CTG GTC NAT AAG GGC AAG CAA GTT        576
Cys Met Gly Asp Ser Gly Gly Pro Leu Val Xaa Lys Gly Lys Gln Val
        180                 185                 190

GGA GTC ACA TCT TTC GTC TGG GAA GGT TGT GCT TTG GGC AAC CCT GAT        624
Gly Val Thr Ser Phe Val Trp Glu Gly Cys Ala Leu Gly Asn Pro Asp
        195                 200                 205

TTC TTT ACA AGA GTT TCG CTT TAT GTA GAC TGG GTC AAA AAG ATT CAA        672
Phe Phe Thr Arg Val Ser Leu Tyr Val Asp Trp Val Lys Lys Ile Gln
        210                 215                 220

AAA GAA TAT AAA T GATATGTTGA TTGTCACTAA AATGCATCGA TTTGGATAAT          725
Lys Glu Tyr Lys
225

TTGGTTGTGA ATATAATTTT ATTTCTAGCA TCAAAAAAAA AAAAAAAAAA                 775
```

(2) INFORMATION FOR SEQ ID NO:10:

(i) SEQUENCE CHARACTERISTICS:
        (A) LENGTH: 228 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 187

(xi) SEQUENCE DESCRIPTION: SEQ ID NO:10:

```
Ser Asn Arg Ile Val Asn Gly Val Asn Ala Lys Asn Gly Ser Ala Pro
1               5                   10                  15

Tyr Met Ala Ser Leu Arg Asp Val Met Glu Thr Ile Ser Val Glu His
            20                  25                  30

Arg Tyr Trp Met Asn Arg Trp Ile Leu Thr Ala Ala His Cys Leu Thr
        35                  40                  45

Asp Gly Tyr Leu Asp Thr Val Tyr Val Gly Ser Asn His Leu Ser Gly
    50                  55                  60

Asp Gly Glu Tyr Tyr Asn Val Glu Glu Gln Val Ile His Asp Lys Tyr
65                  70                  75                  80

Phe Gly Gln Thr Thr Gly Phe Lys Asn Asp Ile Ala Leu Val Lys Val
            85                  90                  95

Ser Ser Ala Ile Lys Leu Ser Lys Asn Val Arg Pro Ile Lys Leu His
            100                 105                 110

Lys Asp Phe Ile Arg Gly Gly Glu Lys Leu Lys Ile Thr Gly Trp Gly
        115                 120                 125

Leu Thr Asn Gln Thr His Gly Glu Val Pro Asp Ala Leu Gln Glu Leu
    130                 135                 140

Gln Val Glu Ala Leu Ser Asn Ser Lys Cys Lys Ala Ile Thr Gly Val
145                 150                 155                 160

His Leu Pro Ala His Leu Cys Thr Phe Lys Ala Pro Gln Lys Gly Val
            165                 170                 175

Cys Met Gly Asp Ser Gly Gly Pro Leu Val Xaa Lys Gly Lys Gln Val
        180                 185                 190

Gly Val Thr Ser Phe Val Trp Glu Gly Cys Ala Leu Gly Asn Pro Asp
        195                 200                 205

Phe Phe Thr Arg Val Ser Leu Tyr Val Asp Trp Val Lys Lys Ile Gln
    210                 215                 220

Lys Glu Tyr Lys
```

225

(2) INFORMATION FOR SEQ ID NO:11:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TTTTTTTTTT TTTTTTTTGA TGCTAGAAAT AAAATTATAT TCACAACCAA ATTATCCAAA    60
TCGATGCATT TTAGTGACAA TCAACATATC ATTTATATTC TTTTTGAATC TTTTTGACCC   120
AGTCTACATA AAGCGAAACT CTTGTAAAGA AATCAGGGTT GCCCAAAGCA CAACCTTCCC   180
AGACGAAAGA TGTGACTCCA ACTTGCTTGC CCTTATNGAC CAGAGGACCA CCAGAGTCAC   240
CCATGCATAC ACCCTTTTGA GGTGCTTTGA AGGTGCAGAG ATGAGCAGGA AGATGGACAC   300
CAGTAATTGC CTTGCATTTA GAGTTAGAAA GTGCTTCTAC CTGTAACTCT TGAAGAGCAT   360
CAGGAACTTC ACCATGAGTT TGATTGGTCA ATCCCCATCC AGTAATTTTC AATTTTTCAC   420
CTCCGCGTAT AAAATCTTTG TGCAATTTGA TGGGACGAAC ATTTTTGCTA AGTTTTATAG   480
CACTAGAAAC TTTGACGAGA GCAATATCAT TTTTGAAGCC GGTTGTTTGA CCAAAATATT   540
TATCATGGAT GACTTGTTCT TCTACATTGT AGTACTCTCC GTCGCCAGAA AGATGATTTG   600
AACCAACGTA GACTGTATCT AGATAACCGT CAGTAAGGCA ATGGGCAGCA GTAAGAATCC   660
AGCGGTTCAT CCAATATCGA TGCTCCACAG AAATGGTTTC CATAACATCT CTTAGAGAAG   720
CCATATATGG AGCAGAACCG TTTTTGGCAT TAACTCCATT AACAATCCGA TTTGA         775
```

(2) INFORMATION FOR SEQ ID NO:12:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..675

(ix) FEATURE:
        (A) NAME/KEY: Xaa = any amino acid
        (B) LOCATION: 184

(xi) SEQUENCE DESCRIPTION: SEQ ID NO:12:

```
ATT GTT AAT GGA GTT AAT GCC AAA AAC GGT TCT GCT CCA TAT ATG GCT     48
Ile Val Asn Gly Val Asn Ala Lys Asn Gly Ser Ala Pro Tyr Met Ala
 1               5                  10                  15

TCT CTA AGA GAT GTT ATG GAA ACC ATT TCT GTG GAG CAT CGA TAT TGG     96
Ser Leu Arg Asp Val Met Glu Thr Ile Ser Val Glu His Arg Tyr Trp
             20                  25                  30

ATG AAC CGC TGG ATT CTT ACT GCT GCC CAT TGC CTT ACT GAC GGT TAT    144
Met Asn Arg Trp Ile Leu Thr Ala Ala His Cys Leu Thr Asp Gly Tyr
         35                  40                  45

CTA GAT ACA GTC TAC GTT GGT TCA AAT CAT CTT TCT GGC GAC GGA GAG    192
Leu Asp Thr Val Tyr Val Gly Ser Asn His Leu Ser Gly Asp Gly Glu
     50                  55                  60

TAC TAC AAT GTA GAA GAA CAA GTC ATC CAT GAT AAA TAT TTT GGT CAA    240
```

| | | |
|---|---|---|
| Tyr Tyr Asn Val Glu Glu Gln Val Ile His Asp Lys Tyr Phe Gly Gln<br>65                        70                    75                    80 | | |
| ACA ACC GGC TTC AAA AAT GAT ATT GCT CTC GTC AAA GTT TCT AGT GCT<br>Thr Thr Gly Phe Lys Asn Asp Ile Ala Leu Val Lys Val Ser Ser Ala<br>              85                    90                    95 | 288 | |
| ATA AAA CTT AGC AAA AAT GTT CGT CCC ATC AAA TTG CAC AAA GAT TTT<br>Ile Lys Leu Ser Lys Asn Val Arg Pro Ile Lys Leu His Lys Asp Phe<br>         100                    105                  110 | 336 | |
| ATA CGC GGA GGT GAA AAA TTG AAA ATT ACT GGA TGG GGA TTG ACC AAT<br>Ile Arg Gly Gly Glu Lys Leu Lys Ile Thr Gly Trp Gly Leu Thr Asn<br>         115                    120                  125 | 384 | |
| CAA ACT CAT GGT GAA GTT CCT GAT GCT CTT CAA GAG TTA CAG GTA GAA<br>Gln Thr His Gly Glu Val Pro Asp Ala Leu Gln Glu Leu Gln Val Glu<br>130                        135                    140 | 432 | |
| GCA CTT TCT AAC TCT AAA TGC AAG GCA ATT ACT GGT GTC CAT CTT CCT<br>Ala Leu Ser Asn Ser Lys Cys Lys Ala Ile Thr Gly Val His Leu Pro<br>145                        150                    155                  160 | 480 | |
| GCT CAT CTC TGC ACC TTC AAA GCA CCT CAA AAG GGT GTA TGC ATG GGT<br>Ala His Leu Cys Thr Phe Lys Ala Pro Gln Lys Gly Val Cys Met Gly<br>         165                    170                  175 | 528 | |
| GAC TCT GGT GGT CCT CTG GTC NAT AAG GGC AAG CAA GTT GGA GTC ACA<br>Asp Ser Gly Gly Pro Leu Val Xaa Lys Gly Lys Gln Val Gly Val Thr<br>              180                    185                  190 | 576 | |
| TCT TTC GTC TGG GAA GGT TGT GCT TTG GGC AAC CCT GAT TTC TTT ACA<br>Ser Phe Val Trp Glu Gly Cys Ala Leu Gly Asn Pro Asp Phe Phe Thr<br>         195                    200                  205 | 624 | |
| AGA GTT TCG CTT TAT GTA GAC TGG GTC AAA AAG ATT CAA AAA GAA TAT<br>Arg Val Ser Leu Tyr Val Asp Trp Val Lys Lys Ile Gln Lys Glu Tyr<br>         210                    215                  220 | 672 | |
| AAA<br>Lys<br>225 | 675 | |

(2) INFORMATION FOR SEQ ID NO:13:

(i) SEQUENCE CHARACTERISTICS:
        (A) LENGTH: 225 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 184

(xi) SEQUENCE DESCRIPTION: SEQ ID NO:13:

Ile Val Asn Gly Val Asn Ala Lys Asn Gly Ser Ala Pro Tyr Met Ala
1                  5                    10                  15

Ser Leu Arg Asp Val Met Glu Thr Ile Ser Val Glu His Arg Tyr Trp
              20                    25                    30

Met Asn Arg Trp Ile Leu Thr Ala Ala His Cys Leu Thr Asp Gly Tyr
              35                    40                    45

Leu Asp Thr Val Tyr Val Gly Ser Asn His Leu Ser Gly Asp Gly Glu
              50                    55                    60

Tyr Tyr Asn Val Glu Glu Gln Val Ile His Asp Lys Tyr Phe Gly Gln
65                        70                    75                    80

Thr Thr Gly Phe Lys Asn Asp Ile Ala Leu Val Lys Val Ser Ser Ala
              85                    90                    95

Ile Lys Leu Ser Lys Asn Val Arg Pro Ile Lys Leu His Lys Asp Phe
         100                    105                  110

Ile Arg Gly Gly Glu Lys Leu Lys Ile Thr Gly Trp Gly Leu Thr Asn
    115                 120                 125

Gln Thr His Gly Glu Val Pro Asp Ala Leu Gln Glu Leu Gln Val Glu
    130                 135                 140

Ala Leu Ser Asn Ser Lys Cys Lys Ala Ile Thr Gly Val His Leu Pro
145                 150                 155                 160

Ala His Leu Cys Thr Phe Lys Ala Pro Gln Lys Gly Val Cys Met Gly
                165                 170                 175

Asp Ser Gly Gly Pro Leu Val Xaa Lys Gly Lys Gln Val Gly Val Thr
            180                 185                 190

Ser Phe Val Trp Glu Gly Cys Ala Leu Gly Asn Pro Asp Phe Phe Thr
            195                 200                 205

Arg Val Ser Leu Tyr Val Asp Trp Val Lys Lys Ile Gln Lys Glu Tyr
    210                 215                 220

Lys
225

(2) INFORMATION FOR SEQ ID NO:14:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

| | | | | | |
|---|---|---|---|---|---|
| TTTATATTCT | TTTTGAATCT | TTTTGACCCA | GTCTACATAA | AGCGAAACTC | TTGTAAAGAA | 60 |
| ATCAGGGTTG | CCCAAAGCAC | AACCTTCCCA | GACGAAAGAT | GTGACTCCAA | CTTGCTTGCC | 120 |
| CTTATNGACC | AGAGGACCAC | CAGAGTCACC | CATGCATACA | CCCTTTTGAG | GTGCTTTGAA | 180 |
| GGTGCAGAGA | TGAGCAGGAA | GATGGACACC | AGTAATTGCC | TTGCATTTAG | AGTTAGAAAG | 240 |
| TGCTTCTACC | TGTAACTCTT | GAAGAGCATC | AGGAACTTCA | CCATGAGTTT | GATTGGTCAA | 300 |
| TCCCCATCCA | GTAATTTTCA | ATTTTTCACC | TCCGCGTATA | AAATCTTTGT | GCAATTTGAT | 360 |
| GGGACGAACA | TTTTTGCTAA | GTTTTATAGC | ACTAGAAACT | TTGACGAGAG | CAATATCATT | 420 |
| TTTGAAGCCG | GTTGTTTGAC | CAAAATATTT | ATCATGGATG | ACTTGTTCTT | CTACATTGTA | 480 |
| GTACTCTCCG | TCGCCAGAAA | GATGATTTGA | ACCAACGTAG | ACTGTATCTA | GATAACCGTC | 540 |
| AGTAAGGCAA | TGGGCAGCAG | TAAGAATCCA | GCGGTTCATC | CAATATCGAT | GCTCCACAGA | 600 |
| AATGGTTTCC | ATAACATCTC | TTAGAGAAGC | CATATATGGA | GCAGAACCGT | TTTTGGCATT | 660 |
| AACTCCATTA | ACAAT | | | | | 675 |

(2) INFORMATION FOR SEQ ID NO:15:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 33..807

(xi) SEQUENCE DESCRIPTION: SEQ ID NO:15:

```
GTTTTTAGTG CGGTGTTAAA TAAAAGTTTA AA ATG AAA CTC ATC ATC GTG CTA         53
                                   Met Lys Leu Ile Ile Val Leu
                                     1               5

GCA TTT GTT TTA GGA ATT TGT TCA GGT TCT CCA CAT TCA AGA ATA ATT        101
Ala Phe Val Leu Gly Ile Cys Ser Gly Ser Pro His Ser Arg Ile Ile
         10              15              20

TGT GGT CAA AAT GCC AAA AAA AAT TCG GCT CCA TAC ATG GCA TCG GTT        149
Cys Gly Gln Asn Ala Lys Lys Asn Ser Ala Pro Tyr Met Ala Ser Val
     25              30              35

CAA CTT TTA GAT AAA GTT GAA GGA GTC GAA AAA TTG TTT CAT TTT TGC        197
Gln Leu Leu Asp Lys Val Glu Gly Val Glu Lys Leu Phe His Phe Cys
 40              45              50              55

GGA GGA GCA ATA GTT AAT GAT AGA TGG ATT TTG ACT GCT GCA CAT TGT        245
Gly Gly Ala Ile Val Asn Asp Arg Trp Ile Leu Thr Ala Ala His Cys
             60              65              70

TTG AGA GGC AAA GAC CAC CTC CTG GAC AAA CTG TTC ATT GCA GTC GGC        293
Leu Arg Gly Lys Asp His Leu Leu Asp Lys Leu Phe Ile Ala Val Gly
         75              80              85

CTG ACA AAT TTA GGT GAA GGA GGC ACC GTG TAT CCT GTA GAA AAA GGC        341
Leu Thr Asn Leu Gly Glu Gly Gly Thr Val Tyr Pro Val Glu Lys Gly
         90              95             100

ATC ATG CAC GAA GAA TAT GAA CAT TAT GAC ATA GTC AAC GAT ATT GCA        389
Ile Met His Glu Glu Tyr Glu His Tyr Asp Ile Val Asn Asp Ile Ala
105             110             115

CTA ATC AAA GTC AAA TCT CCG ATA GAA TTC AAT GAA AAA GTA ACG ACT        437
Leu Ile Lys Val Lys Ser Pro Ile Glu Phe Asn Glu Lys Val Thr Thr
120             125             130             135

GTA AAA TTA GGT GAG GAT TAT GTT GGC GGA GAC GTC CAA CTT CGA TTG        485
Val Lys Leu Gly Glu Asp Tyr Val Gly Gly Asp Val Gln Leu Arg Leu
             140             145             150

ACA GGA TGG GGA GTT ACG ACA AAT GAG GGA ATC GGA AGC CCG AGT CAA        533
Thr Gly Trp Gly Val Thr Thr Asn Glu Gly Ile Gly Ser Pro Ser Gln
         155             160             165

AAA TTA CAG GTC ATG ACA GCC AAA TCA CTA ACT TAT GAG GAT TGC AAA        581
Lys Leu Gln Val Met Thr Ala Lys Ser Leu Thr Tyr Glu Asp Cys Lys
170             175             180

AAC GCA ATT TAT AAA AAG ACT TTC GAA AGC CAA ATT TGT GCA CAG GCT        629
Asn Ala Ile Tyr Lys Lys Thr Phe Glu Ser Gln Ile Cys Ala Gln Ala
185             190             195

AAA AAA GGA ACC GGA TCT TGT AAG GGT GAT TCT GGT GGT CCA TTA GTC        677
Lys Lys Gly Thr Gly Ser Cys Lys Gly Asp Ser Gly Gly Pro Leu Val
200             205             210             215

CAA GGA AAC AAT ACA TTG GTC GGT TTA GTA TCC TGG GGT ATG CAA CCT        725
Gln Gly Asn Asn Thr Leu Val Gly Leu Val Ser Trp Gly Met Gln Pro
             220             225             230

TGT GGA AGT GGT TAT TAT CCT GAC GTT TAC ACA AGA ATT ACA TCG TTT        773
Cys Gly Ser Gly Tyr Tyr Pro Asp Val Tyr Thr Arg Ile Thr Ser Phe
         235             240             245

TTG GAC TGG ATT AAC ACG ACA ATG TCA GAA AAT T AAAGANAAAA               817
Leu Asp Trp Ile Asn Thr Thr Met Ser Glu Asn
         250             255

AANTATCAAA ATAGTAGTTA AAATATTTTG TNGACTACTG TAAAAGTATT GAAATTAACA      877

AATATTTGTT TTGTATATAG GGCTGGTACC TAAAGACATT ATTATTTGTT AAAACTGATA      937

TTTATTTTTA TGACGAATTT CTATATTTAT AATATTATTT TATATGTATG TATTTGATTG      997

TATTTTAAAT ATGGACTGGT TGTTCCCAAT GTTATAAATT AAAATTATAA AAATACATCT     1057

ACTATTTTAT ACTAAAAAAA AAAAAAAAAA AA                                   1089
```

(2) INFORMATION FOR SEQ ID NO:16:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Leu Ile Ile Val Leu Ala Phe Val Leu Gly Ile Cys Ser Gly
 1               5                  10                  15

Ser Pro His Ser Arg Ile Ile Cys Gly Gln Asn Ala Lys Lys Asn Ser
            20                  25                  30

Ala Pro Tyr Met Ala Ser Val Gln Leu Leu Asp Lys Val Glu Gly Val
        35                  40                  45

Glu Lys Leu Phe His Phe Cys Gly Ala Ile Val Asn Asp Arg Trp
 50                  55                  60

Ile Leu Thr Ala Ala His Cys Leu Arg Gly Lys Asp His Leu Leu Asp
 65                  70                  75                  80

Lys Leu Phe Ile Ala Val Gly Leu Thr Asn Leu Gly Glu Gly Gly Thr
                85                  90                  95

Val Tyr Pro Val Glu Lys Gly Ile Met His Glu Glu Tyr Glu His Tyr
           100                 105                 110

Asp Ile Val Asn Asp Ile Ala Leu Ile Lys Val Lys Ser Pro Ile Glu
       115                 120                 125

Phe Asn Glu Lys Val Thr Thr Val Lys Leu Gly Glu Asp Tyr Val Gly
130                 135                 140

Gly Asp Val Gln Leu Arg Leu Thr Gly Trp Gly Val Thr Thr Asn Glu
145                 150                 155                 160

Gly Ile Gly Ser Pro Ser Gln Lys Leu Gln Val Met Thr Ala Lys Ser
                165                 170                 175

Leu Thr Tyr Glu Asp Cys Lys Asn Ala Ile Tyr Lys Lys Thr Phe Glu
            180                 185                 190

Ser Gln Ile Cys Ala Gln Ala Lys Lys Gly Thr Gly Ser Cys Lys Gly
        195                 200                 205

Asp Ser Gly Gly Pro Leu Val Gln Gly Asn Asn Thr Leu Val Gly Leu
210                 215                 220

Val Ser Trp Gly Met Gln Pro Cys Gly Ser Gly Tyr Tyr Pro Asp Val
225                 230                 235                 240

Tyr Thr Arg Ile Thr Ser Phe Leu Asp Trp Ile Asn Thr Thr Met Ser
                245                 250                 255

Glu Asn
```

(2) INFORMATION FOR SEQ ID NO:17:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
TTTTTTTTTT TTTTTTTTTA GTATAAAATA GTAGATGTAT TTTTATAATT TTAATTTATA    60

ACATTGGGAA CAACCAGTCC ATATTTAAAA TACAATCAAA TACATACATA TAAAATAATA   120

TTATAAAATA TAGAAATTCGT CATAAAAATA AATATCAGTT TTAACAAATA ATAATGTCTT   180
```

-continued

| | |
|---|---|
| TAGGTACCAG CCCTATATAC AAAACAAATA TTTGTTAATT TCAATACTTT TACAGTAGTC | 240 |
| NACAAAATAT TTTAACTACT ATTTTGATAN TTTTTTNTCT TTAATTTTCT GACATTGTCG | 300 |
| TGTTAATCCA GTCCAAAAAC GATGTAATTC TTGTGTAAAC GTCAGGATAA TAACCACTTC | 360 |
| CACAAGGTTG CATACCCCAG GATACTAAAC CGACCAATGT ATTGTTTCCT TGGACTAATG | 420 |
| GACCACCAGA ATCACCCTTA CAAGATCCGG TTCCTTTTTT AGCCTGTGCA CAAATTTGGC | 480 |
| TTTCGAAAGT CTTTTTATAA ATTGCGTTTT TGCAATCCTC ATAAGTTAGT GATTTGGCTG | 540 |
| TCATGACCTG TAATTTTTGA CTCGGGCTTC CGATTCCCTC ATTTGTCGTA ACTCCCCATC | 600 |
| CTGTCAATCG AAGTTGGACG TCTCCGCCAA CATAATCCTC ACCTAATTTT ACAGTCGTTA | 660 |
| CTTTTTCATT GAATTCTATC GGAGATTTGA CTTTGATTAG TGCAATATCG TTGACTATGT | 720 |
| CATAATGTTC ATATTCTTCG TGCATGATGC CTTTTTCTAC AGGATACACG GTGCCTCCTT | 780 |
| CACCTAAATT TGTCAGGCCG ACTGCAATGA ACAGTTTGTC CAGGAGGTGG TCTTTGCCTC | 840 |
| TCAAACAATG TGCAGCAGTC AAAATCCATC TATCATTAAC TATTGCTCCT CCGCAAAAAT | 900 |
| GAAACAATTT TTCGACTCCT TCAACTTTAT CTAAAAGTTG AACCGATGCC ATGTATGGAG | 960 |
| CCGAATTTTT TTTGGCATTT TGACCACAAA TTATTCTTGA ATGTGGAGAA CCTGAACAAA | 1020 |
| TTCCTAAAAC AAATGCTAGC ACGATGATGA GTTTCATTTT AAACTTTTAT TTAACACCGC | 1080 |
| ACTAAAAAC | 1089 |

(2) INFORMATION FOR SEQ ID NO:18:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..774

(xi) SEQUENCE DESCRIPTION: SEQ ID NO:18:

| | |
|---|---|
| ATG AAA CTC ATC ATC GTG CTA GCA TTT GTT TTA GGA ATT TGT TCA GGT<br>Met Lys Leu Ile Ile Val Leu Ala Phe Val Leu Gly Ile Cys Ser Gly<br>1              5                    10                 15 | 48 |
| TCT CCA CAT TCA AGA ATA ATT TGT GGT CAA AAT GCC AAA AAA AAT TCG<br>Ser Pro His Ser Arg Ile Ile Cys Gly Gln Asn Ala Lys Lys Asn Ser<br>          20                    25                    30 | 96 |
| GCT CCA TAC ATG GCA TCG GTT CAA CTT TTA GAT AAA GTT GAA GGA GTC<br>Ala Pro Tyr Met Ala Ser Val Gln Leu Leu Asp Lys Val Glu Gly Val<br>      35                    40                    45 | 144 |
| GAA AAA TTG TTT CAT TTT TGC GGA GGA GCA ATA GTT AAT GAT AGA TGG<br>Glu Lys Leu Phe His Phe Cys Gly Gly Ala Ile Val Asn Asp Arg Trp<br>    50                    55                    60 | 192 |
| ATT TTG ACT GCT GCA CAT TGT TTG AGA GGC AAA GAC CAC CTC CTG GAC<br>Ile Leu Thr Ala Ala His Cys Leu Arg Gly Lys Asp His Leu Leu Asp<br>65                    70                    75                    80 | 240 |
| AAA CTG TTC ATT GCA GTC GGC CTG ACA AAT TTA GGT GAA GGA GGC ACC<br>Lys Leu Phe Ile Ala Val Gly Leu Thr Asn Leu Gly Glu Gly Gly Thr<br>          85                    90                    95 | 288 |
| GTG TAT CCT GTA GAA AAA GGC ATC ATG CAC GAA GAA TAT GAA CAT TAT<br>Val Tyr Pro Val Glu Lys Gly Ile Met His Glu Glu Tyr Glu His Tyr<br>            100                 105                 110 | 336 |
| GAC ATA GTC AAC GAT ATT GCA CTA ATC AAA GTC AAA TCT CCG ATA GAA | 384 |

```
Asp Ile Val Asn Asp Ile Ala Leu Ile Lys Val Lys Ser Pro Ile Glu
            115                 120                 125

TTC AAT GAA AAA GTA ACG ACT GTA AAA TTA GGT GAG GAT TAT GTT GGC      432
Phe Asn Glu Lys Val Thr Thr Val Lys Leu Gly Glu Asp Tyr Val Gly
    130                 135                 140

GGA GAC GTC CAA CTT CGA TTG ACA GGA TGG GGA GTT ACG ACA AAT GAG      480
Gly Asp Val Gln Leu Arg Leu Thr Gly Trp Gly Val Thr Thr Asn Glu
145                 150                 155                 160

GGA ATC GGA AGC CCG AGT CAA AAA TTA CAG GTC ATG ACA GCC AAA TCA      528
Gly Ile Gly Ser Pro Ser Gln Lys Leu Gln Val Met Thr Ala Lys Ser
                165                 170                 175

CTA ACT TAT GAG GAT TGC AAA AAC GCA ATT TAT AAA AAG ACT TTC GAA      576
Leu Thr Tyr Glu Asp Cys Lys Asn Ala Ile Tyr Lys Lys Thr Phe Glu
            180                 185                 190

AGC CAA ATT TGT GCA CAG GCT AAA AAA GGA ACC GGA TCT TGT AAG GGT      624
Ser Gln Ile Cys Ala Gln Ala Lys Lys Gly Thr Gly Ser Cys Lys Gly
        195                 200                 205

GAT TCT GGT GGT CCA TTA GTC CAA GGA AAC AAT ACA TTG GTC GGT TTA      672
Asp Ser Gly Gly Pro Leu Val Gln Gly Asn Asn Thr Leu Val Gly Leu
210                 215                 220

GTA TCC TGG GGT ATG CAA CCT TGT GGA AGT GGT TAT TAT CCT GAC GTT      720
Val Ser Trp Gly Met Gln Pro Cys Gly Ser Gly Tyr Tyr Pro Asp Val
225                 230                 235                 240

TAC ACA AGA ATT ACA TCG TTT TTG GAC TGG ATT AAC ACG ACA ATG TCA      768
Tyr Thr Arg Ile Thr Ser Phe Leu Asp Trp Ile Asn Thr Thr Met Ser
                245                 250                 255

GAA AAT                                                              774
Glu Asn (2) INFORMATION FOR SEQ ID NO:19:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:19:

Met Lys Leu Ile Ile Val Leu Ala Phe Val Leu Gly Ile Cys Ser Gly
 1               5                  10                  15

Ser Pro His Ser Arg Ile Ile Cys Gly Gln Asn Ala Lys Lys Asn Ser
                20                  25                  30

Ala Pro Tyr Met Ala Ser Val Gln Leu Leu Asp Lys Val Glu Gly Val
            35                  40                  45

Glu Lys Leu Phe His Phe Cys Gly Gly Ala Ile Val Asn Asp Arg Trp
        50                  55                  60

Ile Leu Thr Ala Ala His Cys Leu Arg Gly Lys Asp His Leu Leu Asp
65                  70                  75                  80

Lys Leu Phe Ile Ala Val Gly Leu Thr Asn Leu Gly Glu Gly Gly Thr
                85                  90                  95

Val Tyr Pro Val Glu Lys Gly Ile Met His Glu Tyr Glu His Tyr
            100                 105                 110

Asp Ile Val Asn Asp Ile Ala Leu Ile Lys Val Lys Ser Pro Ile Glu
        115                 120                 125

Phe Asn Glu Lys Val Thr Thr Val Lys Leu Gly Glu Asp Tyr Val Gly
    130                 135                 140

Gly Asp Val Gln Leu Arg Leu Thr Gly Trp Gly Val Thr Thr Asn Glu
145                 150                 155                 160
```

-continued

```
Gly Ile Gly Ser Pro Ser Gln Lys Leu Gln Val Met Thr Ala Lys Ser
                165                 170                 175

Leu Thr Tyr Glu Asp Cys Lys Asn Ala Ile Tyr Lys Lys Thr Phe Glu
            180                 185                 190

Ser Gln Ile Cys Ala Gln Ala Lys Lys Gly Thr Gly Ser Cys Lys Gly
        195                 200                 205

Asp Ser Gly Gly Pro Leu Val Gln Gly Asn Asn Thr Leu Val Gly Leu
    210                 215                 220

Val Ser Trp Gly Met Gln Pro Cys Gly Ser Gly Tyr Tyr Pro Asp Val
225                 230                 235                 240

Tyr Thr Arg Ile Thr Ser Phe Leu Asp Trp Ile Asn Thr Thr Met Ser
                245                 250                 255

Glu Asn
```

(2) INFORMATION FOR SEQ ID NO:20:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
ATTTTCTGAC ATTGTCGTGT TAATCCAGTC CAAAAACGAT GTAATTCTTG TGTAAACGTC    60
AGGATAATAA CCACTTCCAC AAGGTTGCAT ACCCCAGGAT ACTAAACCGA CCAATGTATT   120
GTTTCCTTGG ACTAATGGAC CACCAGAATC ACCCTTACAA GATCCGGTTC CTTTTTTAGC   180
CTGTGCACAA ATTTGGCTTT CGAAAGTCTT TTTATAAATT GCGTTTTTGC AATCCTCATA   240
AGTTAGTGAT TTGGCTGTCA TGACCTGTAA TTTTTGACTC GGGCTTCCGA TTCCCTCATT   300
TGTCGTAACT CCCCATCCTG TCAATCGAAG TTGGACGTCT CCGCCAACAT AATCCTCACC   360
TAATTTTACA GTCGTTACTT TTTCATTGAA TTCTATCGGA GATTTGACTT TGATTAGTGC   420
AATATCGTTG ACTATGTCAT AATGTTCATA TTCTTCGTGC ATGATGCCTT TTTCTACAGG   480
ATACACGGTG CCTCCTTCAC CTAAATTTGT CAGGCCGACT GCAATGAACA GTTTGTCCAG   540
GAGGTGGTCT TTGCCTCTCA ACAATGTGC AGCAGTCAAA ATCCATCTAT CATTAACTAT   600
TGCTCCTCCG CAAAAATGAA ACAATTTTTC GACTCCTTCA ACTTTATCTA AAAGTTGAAC   660
CGATGCCATG TATGGAGCCG AATTTTTTTT GGCATTTTGA CCACAAATTA TTCTTGAATG   720
TGGAGAACCT GAACAAATTC CTAAAACAAA TGCTAGCACG ATGATGAGTT TCAT         774
```

(2) INFORMATION FOR SEQ ID NO:21:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..711

(xi) SEQUENCE DESCRIPTION: SEQ ID NO:21:

```
ATA ATT TGT GGT CAA AAT GCC AAA AAA AAT TCG GCT CCA TAC ATG GCA     48
Ile Ile Cys Gly Gln Asn Ala Lys Lys Asn Ser Ala Pro Tyr Met Ala
```

-continued

```
          1               5                   10                  15
TCG GTT CAA CTT TTA GAT AAA GTT GAA GGA GTC GAA AAA TTG TTT CAT          96
Ser Val Gln Leu Leu Asp Lys Val Glu Gly Val Glu Lys Leu Phe His
                    20                  25                  30

TTT TGC GGA GGA GCA ATA GTT AAT GAT AGA TGG ATT TTG ACT GCT GCA         144
Phe Cys Gly Gly Ala Ile Val Asn Asp Arg Trp Ile Leu Thr Ala Ala
            35                  40                  45

CAT TGT TTG AGA GGC AAA GAC CAC CTC CTG GAC AAA CTG TTC ATT GCA         192
His Cys Leu Arg Gly Lys Asp His Leu Leu Asp Lys Leu Phe Ile Ala
        50                  55                  60

GTC GGC CTG ACA AAT TTA GGT GAA GGA GGC ACC GTG TAT CCT GTA GAA         240
Val Gly Leu Thr Asn Leu Gly Glu Gly Gly Thr Val Tyr Pro Val Glu
    65                  70                  75                  80

AAA GGC ATC ATG CAC GAA GAA TAT GAA CAT TAT GAC ATA GTC AAC GAT         288
Lys Gly Ile Met His Glu Glu Tyr Glu His Tyr Asp Ile Val Asn Asp
                    85                  90                  95

ATT GCA CTA ATC AAA GTC AAA TCT CCG ATA GAA TTC AAT GAA AAA GTA         336
Ile Ala Leu Ile Lys Val Lys Ser Pro Ile Glu Phe Asn Glu Lys Val
            100                 105                 110

ACG ACT GTA AAA TTA GGT GAG GAT TAT GTT GGC GGA GAC GTC CAA CTT         384
Thr Thr Val Lys Leu Gly Glu Asp Tyr Val Gly Gly Asp Val Gln Leu
        115                 120                 125

CGA TTG ACA GGA TGG GGA GTT ACG ACA AAT GAG GGA ATC GGA AGC CCG         432
Arg Leu Thr Gly Trp Gly Val Thr Thr Asn Glu Gly Ile Gly Ser Pro
    130                 135                 140

AGT CAA AAA TTA CAG GTC ATG ACA GCC AAA TCA CTA ACT TAT GAG GAT         480
Ser Gln Lys Leu Gln Val Met Thr Ala Lys Ser Leu Thr Tyr Glu Asp
145                 150                 155                 160

TGC AAA AAC GCA ATT TAT AAA AAG ACT TTC GAA AGC CAA ATT TGT GCA         528
Cys Lys Asn Ala Ile Tyr Lys Lys Thr Phe Glu Ser Gln Ile Cys Ala
                    165                 170                 175

CAG GCT AAA AAA GGA ACC GGA TCT TGT AAG GGT GAT TCT GGT GGT CCA         576
Gln Ala Lys Lys Gly Thr Gly Ser Cys Lys Gly Asp Ser Gly Gly Pro
            180                 185                 190

TTA GTC CAA GGA AAC AAT ACA TTG GTC GGT TTA GTA TCC TGG GGT ATG         624
Leu Val Gln Gly Asn Asn Thr Leu Val Gly Leu Val Ser Trp Gly Met
        195                 200                 205

CAA CCT TGT GGA AGT GGT TAT TAT CCT GAC GTT TAC ACA AGA ATT ACA         672
Gln Pro Cys Gly Ser Gly Tyr Tyr Pro Asp Val Tyr Thr Arg Ile Thr
    210                 215                 220

TCG TTT TTG GAC TGG ATT AAC ACG ACA ATG TCA GAA AAT                     711
Ser Phe Leu Asp Trp Ile Asn Thr Thr Met Ser Glu Asn
225                 230                 235
```

(2) INFORMATION FOR SEQ ID NO:22:

(i) SEQUENCE CHARACTERISTICS:
        (A) LENGTH: 237 amino acids
        (B) TYPE: amino acid
        (D) TOPOLOGY: linear (ii) MOLECULE TYPE: protein (xi) SEQUENCE DESCRIPTION: SEQ ID NO:22:

```
Ile Ile Cys Gly Gln Asn Ala Lys Lys Asn Ser Ala Pro Tyr Met Ala
1               5                   10                  15

Ser Val Gln Leu Leu Asp Lys Val Glu Gly Val Glu Lys Leu Phe His
                    20                  25                  30

Phe Cys Gly Gly Ala Ile Val Asn Asp Arg Trp Ile Leu Thr Ala Ala
            35                  40                  45
```

```
His Cys Leu Arg Gly Lys Asp His Leu Leu Asp Lys Leu Phe Ile Ala
    50                  55                  60

Val Gly Leu Thr Asn Leu Gly Glu Gly Gly Thr Val Tyr Pro Val Glu
65                  70                  75                  80

Lys Gly Ile Met His Glu Glu Tyr Glu His Tyr Asp Ile Val Asn Asp
                85                  90                  95

Ile Ala Leu Ile Lys Val Lys Ser Pro Ile Glu Phe Asn Glu Lys Val
            100                 105                 110

Thr Thr Val Lys Leu Gly Glu Asp Tyr Val Gly Gly Asp Val Gln Leu
        115                 120                 125

Arg Leu Thr Gly Trp Gly Val Thr Thr Asn Glu Gly Ile Gly Ser Pro
    130                 135                 140

Ser Gln Lys Leu Gln Val Met Thr Ala Lys Ser Leu Thr Tyr Glu Asp
145                 150                 155                 160

Cys Lys Asn Ala Ile Tyr Lys Lys Thr Phe Glu Ser Gln Ile Cys Ala
                165                 170                 175

Gln Ala Lys Lys Gly Thr Gly Ser Cys Lys Gly Asp Ser Gly Gly Pro
            180                 185                 190

Leu Val Gln Gly Asn Asn Thr Leu Val Gly Leu Val Ser Trp Gly Met
        195                 200                 205

Gln Pro Cys Gly Ser Gly Tyr Tyr Pro Asp Val Tyr Thr Arg Ile Thr
    210                 215                 220

Ser Phe Leu Asp Trp Ile Asn Thr Thr Met Ser Glu Asn
225                 230                 235

(2) INFORMATION FOR SEQ ID NO:23:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..800

(ix) FEATURE:
        (A) NAME/KEY: Xaa = any amino acid
        (B) LOCATION: 44

(ix) FEATURE:
        (A) NAME/KEY: Xaa = any amino acid
        (B) LOCATION: 67

(ix) FEATURE:
        (A) NAME/KEY: Xaa = any amino acid
        (B) LOCATION: 260

(xi) SEQUENCE DESCRIPTION: SEQ ID NO:23:

AA ATT TTA TTA CTG GTA TTA TTG GCA GTA TGC TTT GCT TCA GCT AAA            47
   Ile Leu Leu Leu Val Leu Leu Ala Val Cys Phe Ala Ser Ala Lys
    1               5                   10                  15

CGA GGT CCA CGA AAA CAT GTT CGC GAA ACA CAA AAA AGT CTT GCC TCT          95
Arg Gly Pro Arg Lys His Val Arg Glu Thr Gln Lys Ser Leu Ala Ser
                20                  25                  30

GGG CGT ATT GTG GGT GGT GAA GCA GTG AGC ATT GAA NAC TAT GGA TGG         143
Gly Arg Ile Val Gly Gly Glu Ala Val Ser Ile Glu Xaa Tyr Gly Trp
            35                  40                  45

CAA GTT TCT CTA CAA CGT TTT GGC AGT CAT TTC TGT GGA GGA TCT ATA         191
Gln Val Ser Leu Gln Arg Phe Gly Ser His Phe Cys Gly Gly Ser Ile
```

```
                50                    55                    60
ATA TCC AGT ANA TGG ATT CTT TCA GCT GCT CAT TGC TTT TAT GGA ACG      239
Ile Ser Ser Xaa Trp Ile Leu Ser Ala Ala His Cys Phe Tyr Gly Thr
         65                  70                  75

TTA TTT CCG ATT GGA TTC TCT GCG AGA GCC GGC AGC AGT ACT GTG AAT      287
Leu Phe Pro Ile Gly Phe Ser Ala Arg Ala Gly Ser Ser Thr Val Asn
 80                  85                  90                  95

TCA GGA GGA ACT GTG CAT ACA ATT TTG TAT TGG TAT ATT CAT CCA AAT      335
Ser Gly Gly Thr Val His Thr Ile Leu Tyr Trp Tyr Ile His Pro Asn
                    100                 105                 110

TAT GAT TCA CAA AGT ACA GAC TTT GAT GTT TCT GTA GTT CGA CTA TTA      383
Tyr Asp Ser Gln Ser Thr Asp Phe Asp Val Ser Val Val Arg Leu Leu
                115                 120                 125

TCT TCT TTA AAT TTG AAT GGA GGT TCT ATT CGA CCG GCT AGG TTA GTG      431
Ser Ser Leu Asn Leu Asn Gly Gly Ser Ile Arg Pro Ala Arg Leu Val
            130                 135                 140

GAT TCT GGA ACT GAT TTG CCA GCC GGT GAG ATG GTT ACA GTA ACT GGA      479
Asp Ser Gly Thr Asp Leu Pro Ala Gly Glu Met Val Thr Val Thr Gly
145                 150                 155

TGG GGA CGA CTT TCG GAA AAT ACT TCT GTT CCC TCG CCA TCA ACT CTT      527
Trp Gly Arg Leu Ser Glu Asn Thr Ser Val Pro Ser Pro Ser Thr Leu
160                 165                 170                 175

CAA GGA GTT ACA GTA CCA GTT GTA AGT AAT TCG GAA TGT CAA CAA CAA      575
Gln Gly Val Thr Val Pro Val Val Ser Asn Ser Glu Cys Gln Gln Gln
                180                 185                 190

TTG CAA AAT CAG ACA ATC ACT GAC AAT ATG TTT TGT GCT GGT GAA TTA      623
Leu Gln Asn Gln Thr Ile Thr Asp Asn Met Phe Cys Ala Gly Glu Leu
                195                 200                 205

GAA GGA GGA AAG GAC TCT TGT CAA GGA GAC AGT AGT GGT CCC ATG GTT      671
Glu Gly Gly Lys Asp Ser Cys Gln Gly Asp Ser Ser Gly Pro Met Val
            210                 215                 220

GAC AGC GAG GAT ACT CAA GTA GGA ATT GTA TCC TGG GGA ATA GGA TGT      719
Asp Ser Glu Asp Thr Gln Val Gly Ile Val Ser Trp Gly Ile Gly Cys
225                 230                 235

GCT AGA CCC AAT TTA CCA GGA GTT TAT ACG CGA ATT GCT TCA TCG CCA      767
Ala Arg Pro Asn Leu Pro Gly Val Tyr Thr Arg Ile Ala Ser Ser Pro
240                 245                 250                 255

ATT AGA GAT TTC NTA AGA CGA ATA ACC GGA GTT TAATATTATT TTATACATTT    820
Ile Arg Asp Phe Xaa Arg Arg Ile Thr Gly Val
                260                 265

TTGACAAATA TGAGAACTAA TGAGAACTGT TGTNTTGCTA TAATTCTTTG CAACATTGTG    880

CATGAATAAA TTATGAATNT AATTGTTAAA AAAAAAAAAA AAAA                     924

(2) INFORMATION FOR SEQ ID NO:24:

(i) SEQUENCE CHARACTERISTICS:
        (A) LENGTH: 266 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 44

(ix) FEATURE:
        (A) NAME/KEY: Xaa = any amino acid
        (B) LOCATION: 67

(ix) FEATURE:
        (A) NAME/KEY: Xaa = any amino acid
        (B) LOCATION: 260
```

(xi) SEQUENCE DESCRIPTION: SEQ ID NO:24:

```
Ile Leu Leu Leu Val Leu Leu Ala Val Cys Phe Ala Ser Ala Lys Arg
  1               5                  10                  15

Gly Pro Arg Lys His Val Arg Glu Thr Gln Lys Ser Leu Ala Ser Gly
             20                  25                  30

Arg Ile Val Gly Gly Glu Ala Val Ser Ile Glu Xaa Tyr Gly Trp Gln
         35                  40                  45

Val Ser Leu Gln Arg Phe Gly Ser His Phe Cys Gly Gly Ser Ile Ile
     50                  55                  60

Ser Ser Xaa Trp Ile Leu Ser Ala Ala His Cys Phe Tyr Gly Thr Leu
 65                  70                  75                  80

Phe Pro Ile Gly Phe Ser Ala Arg Ala Gly Ser Ser Thr Val Asn Ser
                 85                  90                  95

Gly Gly Thr Val His Thr Ile Leu Tyr Trp Tyr Ile His Pro Asn Tyr
            100                 105                 110

Asp Ser Gln Ser Thr Asp Phe Asp Val Ser Val Val Arg Leu Leu Ser
            115                 120                 125

Ser Leu Asn Leu Asn Gly Gly Ser Ile Arg Pro Ala Arg Leu Val Asp
130                 135                 140

Ser Gly Thr Asp Leu Pro Ala Gly Glu Met Val Thr Val Thr Gly Trp
145                 150                 155                 160

Gly Arg Leu Ser Glu Asn Thr Ser Val Pro Ser Pro Ser Thr Leu Gln
                165                 170                 175

Gly Val Thr Val Pro Val Val Ser Asn Ser Glu Cys Gln Gln Gln Leu
            180                 185                 190

Gln Asn Gln Thr Ile Thr Asp Asn Met Phe Cys Ala Gly Glu Leu Glu
            195                 200                 205

Gly Gly Lys Asp Ser Cys Gln Gly Asp Ser Ser Gly Pro Met Val Asp
210                 215                 220

Ser Glu Asp Thr Gln Val Gly Ile Val Ser Trp Gly Ile Gly Cys Ala
225                 230                 235                 240

Arg Pro Asn Leu Pro Gly Val Tyr Thr Arg Ile Ala Ser Ser Pro Ile
                245                 250                 255

Arg Asp Phe Xaa Arg Arg Ile Thr Gly Val
                260                 265
```

(2) INFORMATION FOR SEQ ID NO:25:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
TTTTTTTTTT TTTTTTTAAC AATTANATTC ATAATTTATT CATGCACAAT GTTGCAAAGA    60

ATTATAGCAA NACAACAGTT CTCATTAGTT CTCATATTTG TCAAAAATGT ATAAAATAAT   120

ATTAAACTCC GGTTATTCGT CTTANGAAAT CTCTAATTGG CGATGAAGCA ATTCGCGTAT   180

AAACTCCTGG TAAATTGGGT CTAGCACATC CTATTCCCCA GGATACAATT CCTACTTGAG   240

TATCCTCGCT GTCAACCATG GGACCACTAC TGTCTCCTTG ACAAGAGTCC TTTCCTCCTT   300

CTAATTCACC AGCACAAAAC ATATTGTCAG TGATTGTCTG ATTTTGCAAT TGTTGTTGAC   360
```

-continued

```
ATTCCGAATT ACTTACAACT GGTACTGTAA CTCCTTGAAG AGTTGATGGC GAGGGAACAG      420

AAGTATTTTC CGAAAGTCGT CCCCATCCAG TTACTGTAAC CATCTCACCG GCTGGCAAAT      480

CAGTTCCAGA ATCCACTAAC CTAGCCGGTC GAATAGAACC TCCATTCAAA TTTAAAGAAG      540

ATAATAGTCG AACTACAGAA ACATCAAAGT CTGTACTTTG TGAATCATAA TTTGGATGAA      600

TATACCAATA CAAAATTGTA TGCACAGTTC CTCCTGAATT CACAGTACTG CTGCCGGCTC      660

TCGCAGAGAA TCCAATCGGA ATAACGTTCC ATAAAAGCA ATGAGCAGCT GAAAGAATCC       720

ATNTACTGGA TATTATAGAT CCTCCACAGA AATGACTGCC AAAACGTTGT AGAGAAACTT      780

GCCATCCATA GTNTTCAATG CTCACTGCTT CACCACCCAC AATACGCCCA GAGGCAAGAC      840

TTTTTTGTGT TTCGCGAACA TGTTTTCGTG GACCTNGTTT AGCTGAAGCA AAGCATACTG      900

CCAATAATAC CAGTAATAAA ATTT                                            924
```

(2) INFORMATION FOR SEQ ID NO:26:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..699

(ix) FEATURE:
        (A) NAME/KEY: Xaa = any amino acid
        (B) LOCATION: 11

(ix) FEATURE:
        (A) NAME/KEY: Xaa = any amino acid
        (B) LOCATION: 34

(ix) FEATURE:
        (A) NAME/KEY: Xaa = any amino acid
        (B) LOCATION: 227

(xi) SEQUENCE DESCRIPTION: SEQ ID NO:26:

```
ATT GTG GGT GGT GAA GCA GTG AGC ATT GAA NAC TAT GGA TGG CAA GTT        48
Ile Val Gly Gly Glu Ala Val Ser Ile Glu Xaa Tyr Gly Trp Gln Val
 1               5                  10                  15

TCT CTA CAA CGT TTT GGC AGT CAT TTC TGT GGA GGA TCT ATA ATA TCC        96
Ser Leu Gln Arg Phe Gly Ser His Phe Cys Gly Gly Ser Ile Ile Ser
            20                  25                  30

AGT ANA TGG ATT CTT TCA GCT GCT CAT TGC TTT TAT GGA ACG TTA TTT       144
Ser Xaa Trp Ile Leu Ser Ala Ala His Cys Phe Tyr Gly Thr Leu Phe
        35                  40                  45

CCG ATT GGA TTC TCT GCG AGA GCC GGC AGC AGT ACT GTG AAT TCA GGA       192
Pro Ile Gly Phe Ser Ala Arg Ala Gly Ser Ser Thr Val Asn Ser Gly
    50                  55                  60

GGA ACT GTG CAT ACA ATT TTG TAT TGG TAT ATT CAT CCA AAT TAT GAT       240
Gly Thr Val His Thr Ile Leu Tyr Trp Tyr Ile His Pro Asn Tyr Asp
65                  70                  75                  80

TCA CAA AGT ACA GAC TTT GAT GTT TCT GTA GTT CGA CTA TTA TCT TCT       288
Ser Gln Ser Thr Asp Phe Asp Val Ser Val Val Arg Leu Leu Ser Ser
                85                  90                  95

TTA AAT TTG AAT GGA GGT TCT ATT CGA CCG GCT AGG TTA GTG GAT TCT       336
Leu Asn Leu Asn Gly Gly Ser Ile Arg Pro Ala Arg Leu Val Asp Ser
            100                 105                 110

GGA ACT GAT TTG CCA GCC GGT GAG ATG GTT ACA GTA ACT GGA TGG GGA       384
Gly Thr Asp Leu Pro Ala Gly Glu Met Val Thr Val Thr Gly Trp Gly
```

```
                115                    120                      125
CGA CTT TCG GAA AAT ACT TCT GTT CCC TCG CCA TCA ACT CTT CAA GGA        432
Arg Leu Ser Glu Asn Thr Ser Val Pro Ser Pro Ser Thr Leu Gln Gly
    130                 135                 140

GTT ACA GTA CCA GTT GTA AGT AAT TCG GAA TGT CAA CAA CAA TTG CAA        480
Val Thr Val Pro Val Val Ser Asn Ser Glu Cys Gln Gln Gln Leu Gln
145                 150                 155                 160

AAT CAG ACA ATC ACT GAC AAT ATG TTT TGT GCT GGT GAA TTA GAA GGA        528
Asn Gln Thr Ile Thr Asp Asn Met Phe Cys Ala Gly Glu Leu Glu Gly
                165                 170                 175

GGA AAG GAC TCT TGT CAA GGA GAC AGT AGT GGT CCC ATG GTT GAC AGC        576
Gly Lys Asp Ser Cys Gln Gly Asp Ser Ser Gly Pro Met Val Asp Ser
            180                 185                 190

GAG GAT ACT CAA GTA GGA ATT GTA TCC TGG GGA ATA GGA TGT GCT AGA        624
Glu Asp Thr Gln Val Gly Ile Val Ser Trp Gly Ile Gly Cys Ala Arg
        195                 200                 205

CCC AAT TTA CCA GGA GTT TAT ACG CGA ATT GCT TCA TCG CCA ATT AGA        672
Pro Asn Leu Pro Gly Val Tyr Thr Arg Ile Ala Ser Ser Pro Ile Arg
    210                 215                 220

GAT TTC NTA AGA CGA ATA ACC GGA GTT                                    699
Asp Phe Xaa Arg Arg Ile Thr Gly Val
225                 230
```

(2) INFORMATION FOR SEQ ID NO:27:

(i) SEQUENCE CHARACTERISTICS:
        (A) LENGTH: 233 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 11

(ix) FEATURE:
        (A) NAME/KEY: Xaa = any amino acid
        (B) LOCATION: 34

(ix) FEATURE:
        (A) NAME/KEY: Xaa = any amino acid
        (B) LOCATION: 227

(xi) SEQUENCE DESCRIPTION: SEQ ID NO:27:

```
Ile Val Gly Gly Glu Ala Val Ser Ile Glu Xaa Tyr Gly Trp Gln Val
 1               5                  10                  15

Ser Leu Gln Arg Phe Gly Ser His Phe Cys Gly Gly Ser Ile Ile Ser
            20                  25                  30

Ser Xaa Trp Ile Leu Ser Ala Ala His Cys Phe Tyr Gly Thr Leu Phe
        35                  40                  45

Pro Ile Gly Phe Ser Ala Arg Ala Gly Ser Ser Thr Val Asn Ser Gly
    50                  55                  60

Gly Thr Val His Thr Ile Leu Tyr Trp Tyr Ile His Pro Asn Tyr Asp
65                  70                  75                  80

Ser Gln Ser Thr Asp Phe Asp Val Ser Val Val Arg Leu Leu Ser Ser
                85                  90                  95

Leu Asn Leu Asn Gly Gly Ser Ile Arg Pro Ala Arg Leu Val Asp Ser
            100                 105                 110

Gly Thr Asp Leu Pro Ala Gly Glu Met Val Thr Val Thr Gly Trp Gly
        115                 120                 125

Arg Leu Ser Glu Asn Thr Ser Val Pro Ser Pro Ser Thr Leu Gln Gly
```

```
            130                 135                 140
Val Thr Val Pro Val Val Ser Asn Ser Glu Cys Gln Gln Gln Leu Gln
145                 150                 155                 160

Asn Gln Thr Ile Thr Asp Asn Met Phe Cys Ala Gly Glu Leu Glu Gly
                165                 170                 175

Gly Lys Asp Ser Cys Gln Gly Asp Ser Ser Gly Pro Met Val Asp Ser
                180                 185                 190

Glu Asp Thr Gln Val Gly Ile Val Ser Trp Gly Ile Gly Cys Ala Arg
            195                 200                 205

Pro Asn Leu Pro Gly Val Tyr Thr Arg Ile Ala Ser Ser Pro Ile Arg
        210                 215                 220

Asp Phe Xaa Arg Arg Ile Thr Gly Val
225                 230
```

(2) INFORMATION FOR SEQ ID NO:28:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
AACTCCGGTT ATTCGTCTTA NGAAATCTCT AATTGGCGAT GAAGCAATTC GCGTATAAAC    60
TCCTGGTAAA TTGGGTCTAG CACATCCTAT TCCCCAGGAT ACAATTCCTA CTTGAGTATC   120
CTCGCTGTCA ACCATGGGAC CACTACTGTC TCCTTGACAA GAGTCCTTTC CTCCTTCTAA   180
TTCACCAGCA CAAAACATAT TGTCAGTGAT TGTCTGATTT TGCAATTGTT GTTGACATTC   240
CGAATTACTT ACAACTGGTA CTGTAACTCC TTGAAGAGTT GATGGCGAGG GAACAGAAGT   300
ATTTTCCGAA AGTCGTCCCC ATCCAGTTAC TGTAACCATC TCACCGGCTG GCAAATCAGT   360
TCCAGAATCC ACTAACCTAG CCGGTCGAAT AGAACCTCCA TTCAAATTTA AGAAGATAA    420
TAGTCGAACT ACAGAAACAT CAAAGTCTGT ACTTTGTGAA TCATAATTTG GATGAATATA   480
CCAATACAAA ATTGTATGCA CAGTTCCTCC TGAATTCACA GTACTGCTGC CGGCTCTCGC   540
AGAGAATCCA ATCGGAAATA ACGTTCCATA AAAGCAATGA GCAGCTGAAA GAATCCATNT   600
ACTGGATATT ATAGATCCTC CACAGAAATG ACTGCCAAAA CGTTGTAGAG AAACTTGCCA   660
TCCATAGTNT TCAATGCTCA CTGCTTCACC ACCCACAAT                          699
```

(2) INFORMATION FOR SEQ ID NO:29:

(i) SEQUENCE CHARACTERISTICS:
        (A) LENGTH: 1894 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 335..1535

(xi) SEQUENCE DESCRIPTION: SEQ ID NO:29:

```
ACGCGACGGG CAGTCTCTTT CAGACCGCGG CCGAACGATG TTTTTGACGG TTTAATTTCA    60
ATTTTTGCAA CTTGTGACTT CGAATACACC CGTACGTGAC CTATCCACTT TACCATCGGC   120
CGACCGTGAA AGTTGTGTTT GTGCTATTGA AAATTTCGTG CTCAATAATA AATATTCAGT   180
```

-continued

```
TTTTTTGTCT AATCAGGATA TTTAAATTTA TGTGTACAAG TGTTAAACGC AATCTCGTCG      240

CTCTTCCTAA TTTTCTTGTT GCCAATDCTG GCCTCAGTGC ATCGGCCGAC GCAAATGTGC      300

TTGCAAAATA GAGAAATCCG GTGAAATCAC ACAT ATG TTA GCG ATC GTC CCG          352
                                       Met Leu Ala Ile Val Pro
                                        1               5

TCA AAC GGA GCG TTC GCA GAC CAT GCC AAC CTT GGT GGA GTT GAT GGT        400
Ser Asn Gly Ala Phe Ala Asp His Ala Asn Leu Gly Gly Val Asp Gly
        10              15                  20

CTT TCT GGT TTG ATT CTG GTC GCT GTT GCG ATA TCT TCG ATT GGA TAT        448
Leu Ser Gly Leu Ile Leu Val Ala Val Ala Ile Ser Ser Ile Gly Tyr
            25              30                  35

GCG GAC GCG GCG AAC GTT GCG CAG GAC GGA CAT CCG TCC AGC CAG CAA        496
Ala Asp Ala Ala Asn Val Ala Gln Asp Gly His Pro Ser Ser Gln Gln
        40              45                  50

GAG CAG GAG ATC CTG CTG CTG AAT GCC TTA GCT CGC AGG AAC GGA GCG        544
Glu Gln Glu Ile Leu Leu Leu Asn Ala Leu Ala Arg Arg Asn Gly Ala
55              60                  65                  70

ACG GGG CAC CAA TTT GAC GTA GAT CAA GAT TCA ATT ATG GAT ATG CTA        592
Thr Gly His Gln Phe Asp Val Asp Gln Asp Ser Ile Met Asp Met Leu
                75                  80                  85

GGA AGA ATG ATA CCT CAG ACT TGC CGG TAC AAA GGC GAA CGG TTC GAG        640
Gly Arg Met Ile Pro Gln Thr Cys Arg Tyr Lys Gly Glu Arg Phe Glu
                    90                  95                  100

TGC GGT TTG TCA ATT TCG TGC GTC CTG GGC GGC GGA AAA CCT CTT GAC        688
Cys Gly Leu Ser Ile Ser Cys Val Leu Gly Gly Gly Lys Pro Leu Asp
                105                 110                 115

CTG TGC AGC GGC GGA ATG ATC TGG TCG TGC TGC GTC GAC AGG GAC ATT        736
Leu Cys Ser Gly Gly Met Ile Trp Ser Cys Cys Val Asp Arg Asp Ile
120                 125                 130

CGG CCT GAG CCG CAG CAC CAG GGC GCT CTG CAG AAC GCA ACT TGT GGA        784
Arg Pro Glu Pro Gln His Gln Gly Ala Leu Gln Asn Ala Thr Cys Gly
135                 140                 145                 150

GAA TTG TAC ACG AGG TCT AAT AGA ATC GTA GGA GGT CAT TCA ACA GGA        832
Glu Leu Tyr Thr Arg Ser Asn Arg Ile Val Gly Gly His Ser Thr Gly
                155                 160                 165

TTC GGG TCT CAT CCT TGG CAG GCG GCT TTG ATC AAA TCA GGA TTT TTG        880
Phe Gly Ser His Pro Trp Gln Ala Ala Leu Ile Lys Ser Gly Phe Leu
                170                 175                 180

AGT AAA AAA TTA TCT TGC GGT GGC GCT TTA GTT AGC GAT CGA TGG GTT        928
Ser Lys Lys Leu Ser Cys Gly Gly Ala Leu Val Ser Asp Arg Trp Val
                185                 190                 195

ATA ACT GCT GCA CAT TGC GTT GCC ACG ACA CCA AAT TCG AAC CTG AAG        976
Ile Thr Ala Ala His Cys Val Ala Thr Thr Pro Asn Ser Asn Leu Lys
200                 205                 210

GTG CGA TTG GGC GAA TGG GAC GTC CGC GAC CAC GAT GAG CGA CTG AAC       1024
Val Arg Leu Gly Glu Trp Asp Val Arg Asp His Asp Glu Arg Leu Asn
215                 220                 225                 230

CAC GAG GAA TAC GCA ATC GAA CGC AAA GAA GTT CAT CCT TCA TAT TCA       1072
His Glu Glu Tyr Ala Ile Glu Arg Lys Glu Val His Pro Ser Tyr Ser
                235                 240                 245

CCA ACC GAT TTC CGG AAT GAT GTA GCC TTA GTG AAA CTC GAT AGA ACT       1120
Pro Thr Asp Phe Arg Asn Asp Val Ala Leu Val Lys Leu Asp Arg Thr
                250                 255                 260

GTT ATT TTC AAA CAA CAT ATT TTA CCT GTC TGC TTA CCT CAT AAG CAA       1168
Val Ile Phe Lys Gln His Ile Leu Pro Val Cys Leu Pro His Lys Gln
                265                 270                 275

ATG AAA CTG GCT GGA AAA ATG GCA ACA GTC GCC GGA TGG GGA CGG ACG       1216
Met Lys Leu Ala Gly Lys Met Ala Thr Val Ala Gly Trp Gly Arg Thr
```

-continued

```
        280                 285                 290
AGG CAC GGG CAG AGC ACT GTG CCG GCT GTC TTA CAA GAA GTC GAT GTC      1264
Arg His Gly Gln Ser Thr Val Pro Ala Val Leu Gln Glu Val Asp Val
295                 300                 305                 310

GAG GTG ATT CCG AAT GAA AGA TGC CAG AGG TGG TTC CGT GCT GCG GGT      1312
Glu Val Ile Pro Asn Glu Arg Cys Gln Arg Trp Phe Arg Ala Ala Gly
                    315                 320                 325

CGA CGA GAA ACC ATT CAC GAT GTC TTT CTC TGC GCC GGA TAT AAA GAG      1360
Arg Arg Glu Thr Ile His Asp Val Phe Leu Cys Ala Gly Tyr Lys Glu
                330                 335                 340

GGT GGT CGT GAT TCA TGC CAA GGT GAT TCT GGA GGT CCT CTA ATA ATG      1408
Gly Gly Arg Asp Ser Cys Gln Gly Asp Ser Gly Gly Pro Leu Ile Met
            345                 350                 355

CAG ATT GAG GGT AGA AGG ACC CTT GTG GGT CTA GTT TCT TGG GGC ATT      1456
Gln Ile Glu Gly Arg Arg Thr Leu Val Gly Leu Val Ser Trp Gly Ile
360                 365                 370

GGA TGT GGT CGT GAG CAT TTA CCA GGC GTA TAT ACC AAT ATA CAA AAA      1504
Gly Cys Gly Arg Glu His Leu Pro Gly Val Tyr Thr Asn Ile Gln Lys
375                 380                 385                 390

TTC ATA CCG TGG ATC GAC AAA GTA ATG GGA T AATTTTTATT CCATCGAGCT      1555
Phe Ile Pro Trp Ile Asp Lys Val Met Gly
                    395                 400

TACCCAAAGT ATTTATTAAG TGTTAATCGA AAGTTCCAAT AATAAATTAA TTTAAAATTC    1615

TAAAGACGGG AATTTGAAAG ACCAAAAAGA CATACTTGTG ATTGTGTAAT TTTTATGATT    1675

AACTTTACAT CATCTGTGCT TAATTATTAA TTTGTATTAT TCTTGCAAAT ATTTCAAGAG    1735

TTACCGAAAA GTTTGCTAAT CGATAATGAT ATTTTAAGAA AAACAACTGC TGCTGATTCA    1795

GTCAATGTTA GAATAATTAT GTTTACTAAA TAATATTAAG TTCTGATTAG TAAATAAATA    1855

GCAAAATTAT CTAAATATAT ATAAAAAAAA AAAAAAAA                           1894
```

(2) INFORMATION FOR SEQ ID NO:30:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:30:

```
Met Leu Ala Ile Val Pro Ser Asn Gly Ala Phe Ala Asp His Ala Asn
1               5                   10                  15

Leu Gly Gly Val Asp Gly Leu Ser Gly Leu Ile Leu Val Ala Val Ala
            20                  25                  30

Ile Ser Ser Ile Gly Tyr Ala Asp Ala Ala Asn Val Ala Gln Asp Gly
        35                  40                  45

His Pro Ser Ser Gln Gln Glu Gln Glu Ile Leu Leu Leu Asn Ala Leu
    50                  55                  60

Ala Arg Arg Asn Gly Ala Thr Gly His Gln Phe Asp Val Asp Gln Asp
65                  70                  75                  80

Ser Ile Met Asp Met Leu Gly Arg Met Ile Pro Gln Thr Cys Arg Tyr
                85                  90                  95

Lys Gly Glu Arg Phe Glu Cys Gly Leu Ser Ile Ser Cys Val Leu Gly
            100                 105                 110

Gly Gly Lys Pro Leu Asp Leu Cys Ser Gly Gly Met Ile Trp Ser Cys
        115                 120                 125

Cys Val Asp Arg Asp Ile Arg Pro Glu Pro Gln His Gln Gly Ala Leu
```

```
                130                 135                 140
Gln Asn Ala Thr Cys Gly Glu Leu Tyr Thr Arg Ser Asn Arg Ile Val
145                 150                 155                 160

Gly Gly His Ser Thr Gly Phe Gly Ser His Pro Trp Gln Ala Ala Leu
                165                 170                 175

Ile Lys Ser Gly Phe Leu Ser Lys Lys Leu Ser Cys Gly Gly Ala Leu
                180                 185                 190

Val Ser Asp Arg Trp Val Ile Thr Ala Ala His Cys Val Ala Thr Thr
                195                 200                 205

Pro Asn Ser Asn Leu Lys Val Arg Leu Gly Glu Trp Asp Val Arg Asp
210                 215                 220

His Asp Glu Arg Leu Asn His Glu Glu Tyr Ala Ile Glu Arg Lys Glu
225                 230                 235                 240

Val His Pro Ser Tyr Ser Pro Thr Asp Phe Arg Asn Asp Val Ala Leu
                245                 250                 255

Val Lys Leu Asp Arg Thr Val Ile Phe Lys Gln His Ile Leu Pro Val
                260                 265                 270

Cys Leu Pro His Lys Gln Met Lys Leu Ala Gly Lys Met Ala Thr Val
                275                 280                 285

Ala Gly Trp Gly Arg Thr Arg His Gly Gln Ser Thr Val Pro Ala Val
290                 295                 300

Leu Gln Glu Val Asp Val Glu Val Ile Pro Asn Glu Arg Cys Gln Arg
305                 310                 315                 320

Trp Phe Arg Ala Ala Gly Arg Arg Glu Thr Ile His Asp Val Phe Leu
                325                 330                 335

Cys Ala Gly Tyr Lys Glu Gly Gly Arg Asp Ser Cys Gln Gly Asp Ser
                340                 345                 350

Gly Gly Pro Leu Ile Met Gln Ile Glu Gly Arg Arg Thr Leu Val Gly
                355                 360                 365

Leu Val Ser Trp Gly Ile Gly Cys Gly Arg Glu His Leu Pro Gly Val
370                 375                 380

Tyr Thr Asn Ile Gln Lys Phe Ile Pro Trp Ile Asp Lys Val Met Gly
385                 390                 395                 400

(2) INFORMATION FOR SEQ ID NO:31:

(i) SEQUENCE CHARACTERISTICS:
        (A) LENGTH: 1894 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TTTTTTTTTT TTTTTTTATA TATATTTAGA TAATTTTGCT ATTTATTTAC TAATCAGAAC      60

TTAATATTAT TTAGTAAACA TAATTATTCT AACATTGACT GAATCAGCAG CAGTTGTTTT    120

TCTTAAAATA TCATTATCGA TTAGCAAACT TTTCGGTAAC TCTTGAAATA TTTGCAAGAA    180

TAATACAAAT TAATAATTAA GCACAGATGA TGTAAAGTTA ATCATAAAAA TTACACAATC    240

ACAAGTATGT CTTTTGGTC TTTCAAATTC CCGTCTTTAG AATTTAAAT TAATTTATTA      300

TTGGAACTTT CGATTAACAC TTAATAAATA CTTTGGGTAA GCTCGATGGA ATAAAAATTA    360

TCCCATTACT TTGTCGATCC ACGGTATGAA TTTTTGTATA TTGGTATATA CGCCTGGTAA    420

ATGCTCACGA CCACATCCAA TGCCCCAAGA AACTAGACCC ACAAGGGTCC TTCTACCCTC    480
```

```
AATCTGCATT ATTAGAGGAC CTCCAGAATC ACCTTGGCAT GAATCACGAC CACCCTCTTT      540

ATATCCGGCG CAGAGAAAGA CATCGTGAAT GGTTTCTCGT CGACCCGCAG CACGGAACCA      600

CCTCTGGCAT CTTTCATTCG GAATCACCTC GACATCGACT TCTTGTAAGA CAGCCGGCAC      660

AGTGCTCTGC CCGTGCCTCG TCCGTCCCCA TCCGGCGACT GTTGCCATTT TTCCAGCCAG      720

TTTCATTTGC TTATGAGGTA AGCAGACAGG TAAAATATGT TGTTTGAAAA TAACAGTTCT      780

ATCGAGTTTC ACTAAGGCTA CATCATTCCG GAAATCGGTT GGTGAATATG AAGGATGAAC      840

TTCTTTGCGT TCGATTGCGT ATTCCTCGTG GTTCAGTCGC TCATCGTGGT CGCGGACGTC      900

CCATTCGCCC AATCGCACCT TCAGGTTCGA ATTTGGTGTC GTGGCAACGC AATGTGCAGC      960

AGTTATAACC CATCGATCGC TAACTAAAGC GCCACCGCAA GATAATTTTT TACTCAAAAA     1020

TCCTGATTTG ATCAAAGCCG CCTGCCAAGG ATGAGACCCG AATCCTGTTG AATGACCTCC     1080

TACGATTCTA TTAGACCTCG TGTACAATTC TCCACAAGTT GCGTTCTGCA GAGCGCCCTG     1140

GTGCTGCGGC TCAGGCCGAA TGTCCCTGTC GACGCAGCAC GACCAGATCA TTCCGCCGCT     1200

GCACAGGTCA AGAGGTTTTC CGCCGCCCAG GACGCACGAA ATTGACAAAC CGCACTCGAA     1260

CCGTTCGCCT TTGTACCGGC AAGTCTGAGG TATCATTCTT CCTAGCATAT CCATAATTGA     1320

ATCTTGATCT ACGTCAAATT GGTGCCCCGT CGCTCCGTTC CTGCGAGCTA AGGCATTCAG     1380

CAGCAGGATC TCCTGCTCTT GCTGGCTGGA CGGATGTCCG TCCTGCGCAA CGTTCGCCGC     1440

GTCCGCATAT CCAATCGAAG ATATCGCAAC AGCGACCAGA ATCAAACCAG AAAGACCATC     1500

AACTCCACCA AGGTTGGCAT GGTCTGCGAA CGCTCCGTTT GACGGGACGA TCGCTAACAT     1560

ATGTGTGATT TCACCGGATT TCTCTATTTT GCAAGCACAT TTGCGTCGGC CGATGCACTG     1620

AGGCCAGHAT TGGCAACAAG AAAATTAGGA AGAGCGACGA GATTGCGTTT AACACTTGTA     1680

CACATAAATT TAAATATCCT GATTAGACAA AAAAACTGAA TATTTATTAT TGAGCACGAA     1740

ATTTTCAATA GCACAAACAC AACTTTCACG GTCGGCCGAT GGTAAAGTGG ATAGGTCACG     1800

TACGGGTGTA TTCGAAGTCA CAAGTTGCAA AAATTGAAAT TAAACCGTCA AAAACATCGT     1860

TCGGCCGCGG TCTGAAAGAG ACTGCCCGTC GCGT                                 1894

(2) INFORMATION FOR SEQ ID NO:32:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1200

(xi) SEQUENCE DESCRIPTION: SEQ ID NO:32:

ATG TTA GCG ATC GTC CCG TCA AAC GGA GCG TTC GCA GAC CAT GCC AAC       48
Met Leu Ala Ile Val Pro Ser Asn Gly Ala Phe Ala Asp His Ala Asn
 1               5                  10                  15

CTT GGT GGA GTT GAT GGT CTT TCT GGT TTG ATT CTG GTC GCT GTT GCG       96
Leu Gly Gly Val Asp Gly Leu Ser Gly Leu Ile Leu Val Ala Val Ala
             20                  25                  30

ATA TCT TCG ATT GGA TAT GCG GAC GCG GCG AAC GTT GCG CAG GAC GGA      144
Ile Ser Ser Ile Gly Tyr Ala Asp Ala Ala Asn Val Ala Gln Asp Gly
         35                  40                  45

CAT CCG TCC AGC CAG CAA GAG CAG GAG ATC CTG CTG CTG AAT GCC TTA      192
His Pro Ser Ser Gln Gln Glu Gln Glu Ile Leu Leu Leu Asn Ala Leu
```

```
                50                       55                      60
GCT CGC AGG AAC GGA GCG ACG GGG CAC CAA TTT GAC GTA GAT CAA GAT     240
Ala Arg Arg Asn Gly Ala Thr Gly His Gln Phe Asp Val Asp Gln Asp
 65                      70                      75                  80

TCA ATT ATG GAT ATG CTA GGA AGA ATG ATA CCT CAG ACT TGC CGG TAC     288
Ser Ile Met Asp Met Leu Gly Arg Met Ile Pro Gln Thr Cys Arg Tyr
                         85                      90                      95

AAA GGC GAA CGG TTC GAG TGC GGT TTG TCA ATT TCG TGC GTC CTG GGC     336
Lys Gly Glu Arg Phe Glu Cys Gly Leu Ser Ile Ser Cys Val Leu Gly
                    100                     105                     110

GGC GGA AAA CCT CTT GAC CTG TGC AGC GGC GGA ATG ATC TGG TCG TGC     384
Gly Gly Lys Pro Leu Asp Leu Cys Ser Gly Gly Met Ile Trp Ser Cys
                115                     120                     125

TGC GTC GAC AGG GAC ATT CGG CCT GAG CCG CAG CAC CAG GGC GCT CTG     432
Cys Val Asp Arg Asp Ile Arg Pro Glu Pro Gln His Gln Gly Ala Leu
            130                     135                     140

CAG AAC GCA ACT TGT GGA GAA TTG TAC ACG AGG TCT AAT AGA ATC GTA     480
Gln Asn Ala Thr Cys Gly Glu Leu Tyr Thr Arg Ser Asn Arg Ile Val
145                     150                     155                     160

GGA GGT CAT TCA ACA GGA TTC GGG TCT CAT CCT TGG CAG GCG GCT TTG     528
Gly Gly His Ser Thr Gly Phe Gly Ser His Pro Trp Gln Ala Ala Leu
                    165                     170                     175

ATC AAA TCA GGA TTT TTG AGT AAA AAA TTA TCT TGC GGT GGC GCT TTA     576
Ile Lys Ser Gly Phe Leu Ser Lys Lys Leu Ser Cys Gly Gly Ala Leu
                180                     185                     190

GTT AGC GAT CGA TGG GTT ATA ACT GCT GCA CAT TGC GTT GCC ACG ACA     624
Val Ser Asp Arg Trp Val Ile Thr Ala Ala His Cys Val Ala Thr Thr
            195                     200                     205

CCA AAT TCG AAC CTG AAG GTG CGA TTG GGC GAA TGG GAC GTC CGC GAC     672
Pro Asn Ser Asn Leu Lys Val Arg Leu Gly Glu Trp Asp Val Arg Asp
210                     215                     220

CAC GAT GAG CGA CTG AAC CAC GAG GAA TAC GCA ATC GAA CGC AAA GAA     720
His Asp Glu Arg Leu Asn His Glu Glu Tyr Ala Ile Glu Arg Lys Glu
225                     230                     235                     240

GTT CAT CCT TCA TAT TCA CCA ACC GAT TTC CGG AAT GAT GTA GCC TTA     768
Val His Pro Ser Tyr Ser Pro Thr Asp Phe Arg Asn Asp Val Ala Leu
                    245                     250                     255

GTG AAA CTC GAT AGA ACT GTT ATT TTC AAA CAA CAT ATT TTA CCT GTC     816
Val Lys Leu Asp Arg Thr Val Ile Phe Lys Gln His Ile Leu Pro Val
                260                     265                     270

TGC TTA CCT CAT AAG CAA ATG AAA CTG GCT GGA AAA ATG GCA ACA GTC     864
Cys Leu Pro His Lys Gln Met Lys Leu Ala Gly Lys Met Ala Thr Val
            275                     280                     285

GCC GGA TGG GGA CGG ACG AGG CAC GGG CAG AGC ACT GTG CCG GCT GTC     912
Ala Gly Trp Gly Arg Thr Arg His Gly Gln Ser Thr Val Pro Ala Val
        290                     295                     300

TTA CAA GAA GTC GAT GTC GAG GTG ATT CCG AAT GAA AGA TGC CAG AGG     960
Leu Gln Glu Val Asp Val Glu Val Ile Pro Asn Glu Arg Cys Gln Arg
305                     310                     315                     320

TGG TTC CGT GCT GCG GGT CGA CGA GAA ACC ATT CAC GAT GTC TTT CTC    1008
Trp Phe Arg Ala Ala Gly Arg Arg Glu Thr Ile His Asp Val Phe Leu
                    325                     330                     335

TGC GCC GGA TAT AAA GAG GGT GGT CGT GAT TCA TGC CAA GGT GAT TCT    1056
Cys Ala Gly Tyr Lys Glu Gly Gly Arg Asp Ser Cys Gln Gly Asp Ser
                340                     345                     350

GGA GGT CCT CTA ATA ATG CAG ATT GAG GGT AGA AGG ACC CTT GTG GGT    1104
Gly Gly Pro Leu Ile Met Gln Ile Glu Gly Arg Arg Thr Leu Val Gly
            355                     360                     365

CTA GTT TCT TGG GGC ATT GGA TGT GGT CGT GAG CAT TTA CCA GGC GTA    1152
```

```
Leu Val Ser Trp Gly Ile Gly Cys Gly Arg Glu His Leu Pro Gly Val
    370             375             380

TAT ACC AAT ATA CAA AAA TTC ATA CCG TGG ATC GAC AAA GTA ATG GGA        1200
Tyr Thr Asn Ile Gln Lys Phe Ile Pro Trp Ile Asp Lys Val Met Gly
385             390             395             400
```

(2) INFORMATION FOR SEQ ID NO:33:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:33:

```
Met Leu Ala Ile Val Pro Ser Asn Gly Ala Phe Ala Asp His Ala Asn
1               5              10              15

Leu Gly Gly Val Asp Gly Leu Ser Gly Leu Ile Leu Val Ala Val Ala
                20              25              30

Ile Ser Ser Ile Gly Tyr Ala Asp Ala Ala Asn Val Ala Gln Asp Gly
            35              40              45

His Pro Ser Ser Gln Gln Glu Gln Ile Leu Leu Leu Asn Ala Leu
    50              55              60

Ala Arg Arg Asn Gly Ala Thr Gly His Gln Phe Asp Val Asp Gln Asp
65              70              75              80

Ser Ile Met Asp Met Leu Gly Arg Met Ile Pro Gln Thr Cys Arg Tyr
                85              90              95

Lys Gly Glu Arg Phe Glu Cys Gly Leu Ser Ile Ser Cys Val Leu Gly
                100             105             110

Gly Gly Lys Pro Leu Asp Leu Cys Ser Gly Gly Met Ile Trp Ser Cys
            115             120             125

Cys Val Asp Arg Asp Ile Arg Pro Glu Pro Gln His Gln Gly Ala Leu
130             135             140

Gln Asn Ala Thr Cys Gly Glu Leu Tyr Thr Arg Ser Asn Arg Ile Val
145             150             155             160

Gly Gly His Ser Thr Gly Phe Gly Ser His Pro Trp Gln Ala Ala Leu
                165             170             175

Ile Lys Ser Gly Phe Leu Ser Lys Lys Leu Ser Cys Gly Gly Ala Leu
            180             185             190

Val Ser Asp Arg Trp Val Ile Thr Ala Ala His Cys Val Ala Thr Thr
        195             200             205

Pro Asn Ser Asn Leu Lys Val Arg Leu Gly Glu Trp Asp Val Arg Asp
210             215             220

His Asp Glu Arg Leu Asn His Glu Glu Tyr Ala Ile Glu Arg Lys Glu
225             230             235             240

Val His Pro Ser Tyr Ser Pro Thr Asp Phe Arg Asn Asp Val Ala Leu
                245             250             255

Val Lys Leu Asp Arg Thr Val Ile Phe Lys Gln His Ile Leu Pro Val
            260             265             270

Cys Leu Pro His Lys Gln Met Lys Leu Ala Gly Lys Met Ala Thr Val
        275             280             285

Ala Gly Trp Gly Arg Thr Arg His Gly Gln Ser Thr Val Pro Ala Val
290             295             300

Leu Gln Glu Val Asp Val Glu Val Ile Pro Asn Glu Arg Cys Gln Arg
305             310             315             320
```

```
Trp Phe Arg Ala Ala Gly Arg Arg Glu Thr Ile His Asp Val Phe Leu
            325                 330                 335

Cys Ala Gly Tyr Lys Glu Gly Gly Arg Asp Ser Cys Gln Gly Asp Ser
            340                 345                 350

Gly Gly Pro Leu Ile Met Gln Ile Glu Gly Arg Arg Thr Leu Val Gly
            355                 360                 365

Leu Val Ser Trp Gly Ile Gly Cys Gly Arg Glu His Leu Pro Gly Val
        370                 375                 380

Tyr Thr Asn Ile Gln Lys Phe Ile Pro Trp Ile Asp Lys Val Met Gly
385                 390                 395                 400
```

(2) INFORMATION FOR SEQ ID NO:34:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
TCCCATTACT TTGTCGATCC ACGGTATGAA TTTTTGTATA TTGGTATATA CGCCTGGTAA      60
ATGCTCACGA CCACATCCAA TGCCCCAAGA AACTAGACCC ACAAGGGTCC TTCTACCCTC     120
AATCTGCATT ATTAGAGGAC CTCCAGAATC ACCTTGGCAT GAATCACGAC CACCCTCTTT     180
ATATCCGGCG CAGAGAAAGA CATCGTGAAT GGTTTCTCGT CGACCCGCAG CACGGAACCA     240
CCTCTGGCAT CTTTCATTCG GAATCACCTC GACATCGACT TCTTGTAAGA CAGCCGGCAC     300
AGTGCTCTGC CCGTGCCTCG TCCGTCCCCA TCCGGCGACT GTTGCCATTT TTCCAGCCAG     360
TTTCATTTGC TTATGAGGTA AGCAGACAGG TAAAATATGT TGTTTGAAAA TAACAGTTCT     420
ATCGAGTTTC ACTAAGGCTA CATCATTCCG GAAATCGGTT GGTGAATATG AAGGATGAAC     480
TTCTTTGCGT TCGATTGCGT ATTCCTCGTG GTTCAGTCGC TCATCGTGGT CGCGGACGTC     540
CCATTCGCCC AATCGCACCT TCAGGTTCGA ATTTGGTGTC GTGGCAACGC AATGTGCAGC     600
AGTTATAACC CATCGATCGC TAACTAAAGC GCCACCGCAA GATAATTTTT TACTCAAAAA     660
TCCTGATTTG ATCAAAGCCG CCTGCCAAGG ATGAGACCCG AATCCTGTTG AATGACCTCC     720
TACGATTCTA TTAGACCTCG TGTACAATTC TCCACAAGTT GCGTTCTGCA GAGCGCCCTG     780
GTGCTGCGGC TCAGGCCGAA TGTCCCTGTC GACGCAGCAC GACCAGATCA TTCCGCCGCT     840
GCACAGGTCA AGAGGTTTTC CGCCGCCCAG GACGCACGAA ATTGACAAAC CGCACTCGAA     900
CCGTTCGCCT TTGTACCGGC AAGTCTGAGG TATCATTCTT CCTAGCATAT CCATAATTGA     960
ATCTTGATCT ACGTCAAATT GGTGCCCCGT CGCTCCGTTC CTGCGAGCTA AGGCATTCAG    1020
CAGCAGGATC TCCTGCTCTT GCTGGCTGGA CGGATGTCCG TCCTGCGCAA CGTTCGCCGC    1080
GTCCGCATAT CCAATCGAAG ATATCGCAAC AGCGACCAGA ATCAAACCAG AAAGACCATC    1140
AACTCCACCA AGGTTGGCAT GGTCTGCGAA CGCTCCGTTT GACGGGACGA TCGCTAACAT    1200
```

(2) INFORMATION FOR SEQ ID NO:35:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: CDS
    (B) LOCATION: 1..726

(xi) SEQUENCE DESCRIPTION: SEQ ID NO:35:

| | | | | | | | | | | | | | | | | |
|---|---|---|---|---|---|---|---|---|---|---|---|---|---|---|---|---|
| ATC | GTA | GGA | GGT | CAT | TCA | ACA | GGA | TTC | GGG | TCT | CAT | CCT | TGG | CAG | GCG | 48 |
| Ile | Val | Gly | Gly | His | Ser | Thr | Gly | Phe | Gly | Ser | His | Pro | Trp | Gln | Ala | |
| 1 | | | | 5 | | | | | 10 | | | | | 15 | | |
| GCT | TTG | ATC | AAA | TCA | GGA | TTT | TTG | AGT | AAA | AAA | TTA | TCT | TGC | GGT | GGC | 96 |
| Ala | Leu | Ile | Lys | Ser | Gly | Phe | Leu | Ser | Lys | Lys | Leu | Ser | Cys | Gly | Gly | |
| | | | 20 | | | | | 25 | | | | | 30 | | | |
| GCT | TTA | GTT | AGC | GAT | CGA | TGG | GTT | ATA | ACT | GCT | GCA | CAT | TGC | GTT | GCC | 144 |
| Ala | Leu | Val | Ser | Asp | Arg | Trp | Val | Ile | Thr | Ala | Ala | His | Cys | Val | Ala | |
| | | | 35 | | | | | 40 | | | | | 45 | | | |
| ACG | ACA | CCA | AAT | TCG | AAC | CTG | AAG | GTG | CGA | TTG | GGC | GAA | TGG | GAC | GTC | 192 |
| Thr | Thr | Pro | Asn | Ser | Asn | Leu | Lys | Val | Arg | Leu | Gly | Glu | Trp | Asp | Val | |
| | | | 50 | | | | | 55 | | | | | 60 | | | |
| CGC | GAC | CAC | GAT | GAG | CGA | CTG | AAC | CAC | GAG | GAA | TAC | GCA | ATC | GAA | CGC | 240 |
| Arg | Asp | His | Asp | Glu | Arg | Leu | Asn | His | Glu | Glu | Tyr | Ala | Ile | Glu | Arg | |
| 65 | | | | | 70 | | | | | 75 | | | | | 80 | |
| AAA | GAA | GTT | CAT | CCT | TCA | TAT | TCA | CCA | ACC | GAT | TTC | CGG | AAT | GAT | GTA | 288 |
| Lys | Glu | Val | His | Pro | Ser | Tyr | Ser | Pro | Thr | Asp | Phe | Arg | Asn | Asp | Val | |
| | | | | 85 | | | | | 90 | | | | | 95 | | |
| GCC | TTA | GTG | AAA | CTC | GAT | AGA | ACT | GTT | ATT | TTC | AAA | CAA | CAT | ATT | TTA | 336 |
| Ala | Leu | Val | Lys | Leu | Asp | Arg | Thr | Val | Ile | Phe | Lys | Gln | His | Ile | Leu | |
| | | | 100 | | | | | 105 | | | | | 110 | | | |
| CCT | GTC | TGC | TTA | CCT | CAT | AAG | CAA | ATG | AAA | CTG | GCT | GGA | AAA | ATG | GCA | 384 |
| Pro | Val | Cys | Leu | Pro | His | Lys | Gln | Met | Lys | Leu | Ala | Gly | Lys | Met | Ala | |
| | | | 115 | | | | | 120 | | | | | 125 | | | |
| ACA | GTC | GCC | GGA | TGG | GGA | CGG | ACG | AGG | CAC | GGG | CAG | AGC | ACT | GTG | CCG | 432 |
| Thr | Val | Ala | Gly | Trp | Gly | Arg | Thr | Arg | His | Gly | Gln | Ser | Thr | Val | Pro | |
| 130 | | | | | 135 | | | | | 140 | | | | | | |
| GCT | GTC | TTA | CAA | GAA | GTC | GAT | GTC | GAG | GTG | ATT | CCG | AAT | GAA | AGA | TGC | 480 |
| Ala | Val | Leu | Gln | Glu | Val | Asp | Val | Glu | Val | Ile | Pro | Asn | Glu | Arg | Cys | |
| 145 | | | | | 150 | | | | | 155 | | | | | 160 | |
| CAG | AGG | TGG | TTC | CGT | GCT | GCG | GGT | CGA | CGA | GAA | ACC | ATT | CAC | GAT | GTC | 528 |
| Gln | Arg | Trp | Phe | Arg | Ala | Ala | Gly | Arg | Arg | Glu | Thr | Ile | His | Asp | Val | |
| | | | 165 | | | | | 170 | | | | | 175 | | | |
| TTT | CTC | TGC | GCC | GGA | TAT | AAA | GAG | GGT | GGT | CGT | GAT | TCA | TGC | CAA | GGT | 576 |
| Phe | Leu | Cys | Ala | Gly | Tyr | Lys | Glu | Gly | Gly | Arg | Asp | Ser | Cys | Gln | Gly | |
| | | | 180 | | | | | 185 | | | | | 190 | | | |
| GAT | TCT | GGA | GGT | CCT | CTA | ATA | ATG | CAG | ATT | GAG | GGT | AGA | AGG | ACC | CTT | 624 |
| Asp | Ser | Gly | Gly | Pro | Leu | Ile | Met | Gln | Ile | Glu | Gly | Arg | Arg | Thr | Leu | |
| | | | 195 | | | | | 200 | | | | | 205 | | | |
| GTG | GGT | CTA | GTT | TCT | TGG | GGC | ATT | GGA | TGT | GGT | CGT | GAG | CAT | TTA | CCA | 672 |
| Val | Gly | Leu | Val | Ser | Trp | Gly | Ile | Gly | Cys | Gly | Arg | Glu | His | Leu | Pro | |
| | | 210 | | | | | 215 | | | | | 220 | | | | |
| GGC | GTA | TAT | ACC | AAT | ATA | CAA | AAA | TTC | ATA | CCG | TGG | ATC | GAC | AAA | GTA | 720 |
| Gly | Val | Tyr | Thr | Asn | Ile | Gln | Lys | Phe | Ile | Pro | Trp | Ile | Asp | Lys | Val | |
| 225 | | | | | 230 | | | | | 235 | | | | | 240 | |
| ATG | GGA | | | | | | | | | | | | | | | 726 |
| Met | Gly | | | | | | | | | | | | | | | |

(2) INFORMATION FOR SEQ ID NO:36:

(i) SEQUENCE CHARACTERISTICS:
    (A) LENGTH: 242 amino acids
    (B) TYPE: amino acid
    (D) TOPOLOGY: linear (ii) MOLECULE TYPE: protein (xi) SEQUENCE DESCRIPTION: SEQ ID NO:36:

```
Ile Val Gly Gly His Ser Thr Gly Phe Gly Ser His Pro Trp Gln Ala
  1               5                  10                  15

Ala Leu Ile Lys Ser Gly Phe Leu Ser Lys Lys Leu Ser Cys Gly Gly
             20                  25                  30

Ala Leu Val Ser Asp Arg Trp Val Ile Thr Ala Ala His Cys Val Ala
         35                  40                  45

Thr Thr Pro Asn Ser Asn Leu Lys Val Arg Leu Gly Glu Trp Asp Val
     50                  55                  60

Arg Asp His Asp Glu Arg Leu Asn His Glu Glu Tyr Ala Ile Glu Arg
 65              70                  75                  80

Lys Glu Val His Pro Ser Tyr Ser Pro Thr Asp Phe Arg Asn Asp Val
                 85                  90                  95

Ala Leu Val Lys Leu Asp Arg Thr Val Ile Phe Lys Gln His Ile Leu
            100                 105                 110

Pro Val Cys Leu Pro His Lys Gln Met Lys Leu Ala Gly Lys Met Ala
            115                 120                 125

Thr Val Ala Gly Trp Gly Arg Thr Arg His Gly Gln Ser Thr Val Pro
        130                 135                 140

Ala Val Leu Gln Glu Val Asp Val Glu Val Ile Pro Asn Glu Arg Cys
145                 150                 155                 160

Gln Arg Trp Phe Arg Ala Ala Gly Arg Arg Glu Thr Ile His Asp Val
                165                 170                 175

Phe Leu Cys Ala Gly Tyr Lys Glu Gly Gly Arg Asp Ser Cys Gln Gly
            180                 185                 190

Asp Ser Gly Gly Pro Leu Ile Met Gln Ile Glu Gly Arg Arg Thr Leu
        195                 200                 205

Val Gly Leu Val Ser Trp Gly Ile Gly Cys Gly Arg Glu His Leu Pro
    210                 215                 220

Gly Val Tyr Thr Asn Ile Gln Lys Phe Ile Pro Trp Ile Asp Lys Val
225                 230                 235                 240

Met Gly
```

(2) INFORMATION FOR SEQ ID NO:37:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..428

(ix) FEATURE:
        (A) NAME/KEY: Xaa = any amino acid
        (B) LOCATION: 17

(xi) SEQUENCE DESCRIPTION: SEQ ID NO:37:

```
GTA ACC AAA TAT GAA AAC GAT ATC GAA GGT TTA AAA GTT AGG GTT GGA       48
Val Thr Lys Tyr Glu Asn Asp Ile Glu Gly Leu Lys Val Arg Val Gly
  1               5                  10                  15

ANC AAT GAG CAT AAC AAA GGT GGG CGT TTA TAC GAC ATT AAA GAA ATT       96
Xaa Asn Glu His Asn Lys Gly Gly Arg Leu Tyr Asp Ile Lys Glu Ile
             20                  25                  30

AAA AAA CAT CCA AGA TAT AAC GAT CGA ACC AGA TAC GAT TTT GAT GTC      144
```

```
Lys Lys His Pro Arg Tyr Asn Asp Arg Thr Arg Tyr Asp Phe Asp Val
        35                  40                  45

GCT TTA TTA CGC ATT GCA AAG CCA ATT GCA TAC ACT GCT TGC ACT GTT        192
Ala Leu Leu Arg Ile Ala Lys Pro Ile Ala Tyr Thr Ala Cys Thr Val
 50                  55                  60

GTT CCT GTA GCA TTG GCA GAA ACT GGA AAA GAA GTT CCA GAA GGC GCA        240
Val Pro Val Ala Leu Ala Glu Thr Gly Lys Glu Val Pro Glu Gly Ala
 65                  70                  75                  80

CTC GTT AGT GTC ACA GGA TGG GGG GCT ACT ATG GTG GGC GGC CCA GCA        288
Leu Val Ser Val Thr Gly Trp Gly Ala Thr Met Val Gly Gly Pro Ala
                 85                  90                  95

TCA ACG CAT CTA AAA GGT GTT AAG GTT CCA ATC GTG TCA AAT GAA GAA        336
Ser Thr His Leu Lys Gly Val Lys Val Pro Ile Val Ser Asn Glu Glu
            100                 105                 110

TGC AAC AAA AAT TAT ACC ATT CCT GGA GGT CTG GAT GAC AAA ATT TCA        384
Cys Asn Lys Asn Tyr Thr Ile Pro Gly Gly Leu Asp Asp Lys Ile Ser
            115                 120                 125

GAC AGC ATG TTT TGC GCT GGT TTC CCT GAA GGC GGA AAG GAC     TC        428
Asp Ser Met Phe Cys Ala Gly Phe Pro Glu Gly Gly Lys Asp
        130                 135                 140
```

(2) INFORMATION FOR SEQ ID NO:38:

(i) SEQUENCE CHARACTERISTICS:
        (A) LENGTH: 142 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 17

(xi) SEQUENCE DESCRIPTION: SEQ ID NO:38:

```
Val Thr Lys Tyr Glu Asn Asp Ile Glu Gly Leu Lys Val Arg Val Gly
 1               5                  10                  15

Xaa Asn Glu His Asn Lys Gly Gly Arg Leu Tyr Asp Ile Lys Glu Ile
            20                  25                  30

Lys Lys His Pro Arg Tyr Asn Asp Arg Thr Arg Tyr Asp Phe Asp Val
        35                  40                  45

Ala Leu Leu Arg Ile Ala Lys Pro Ile Ala Tyr Thr Ala Cys Thr Val
 50                  55                  60

Val Pro Val Ala Leu Ala Glu Thr Gly Lys Glu Val Pro Glu Gly Ala
 65                  70                  75                  80

Leu Val Ser Val Thr Gly Trp Gly Ala Thr Met Val Gly Gly Pro Ala
                 85                  90                  95

Ser Thr His Leu Lys Gly Val Lys Val Pro Ile Val Ser Asn Glu Glu
            100                 105                 110

Cys Asn Lys Asn Tyr Thr Ile Pro Gly Gly Leu Asp Asp Lys Ile Ser
            115                 120                 125

Asp Ser Met Phe Cys Ala Gly Phe Pro Glu Gly Gly Lys Asp
        130                 135                 140
```

(2) INFORMATION FOR SEQ ID NO:39:

(i) SEQUENCE CHARACTERISTICS:
        (A) LENGTH: 428 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:39:

```
GAGTCCTTTC CGCCTTCAGG GAAACCAGCG CAAAACATGC TGTCTGAAAT TTTGTCATCC      60

AGACCTCCAG GAATGGTATA ATTTTTGTTG CATTCTTCAT TTGACACGAT TGGAACCTTA     120

ACACCTTTTA GATGCGTTGA TGCTGGGCCG CCCACCATAG TAGCCCCCCA TCCTGTGACA     180

CTAACGAGTG CGCCTTCTGG AACTTCTTTT CCAGTTTCTG CCAATGCTAC AGGAACAACA     240

GTGCAAGCAG TGTATGCAAT TGGCTTTGCA ATGCGTAATA AAGCGACATC AAAATCGTAT     300

CTGGTTCGAT CGTTATATCT TGGATGTTTT TTAATTTCTT TAATGTCGTA TAAACGCCCA     360

CCTTTGTTAT GCTCATTGNT TCCAACCCTA ACTTTTAAAC CTTCGATATC GTTTTCATAT     420

TTGGTTAC                                                              428
```

(2) INFORMATION FOR SEQ ID NO:40:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..728

(ix) FEATURE:
        (A) NAME/KEY: Xaa = any amino acid
        (B) LOCATION: 62

(ix) FEATURE:
        (A) NAME/KEY: Xaa = any amino acid
        (B) LOCATION: 209

(xi) SEQUENCE DESCRIPTION: SEQ ID NO:40:

```
A GAT CAT CGA ATA GTA GGA GGT GAA GAT GTA GAT ATT TCA ACT TGT           46
  Asp His Arg Ile Val Gly Gly Glu Asp Val Asp Ile Ser Thr Cys
  1               5                  10                  15

GGA TGG CAA GTT TCG TTT CAC AAT AGG AAA GGA CAT TTT TGT GGA GGG         94
Gly Trp Gln Val Ser Phe His Asn Arg Lys Gly His Phe Cys Gly Gly
            20                  25                  30

TCC ATC ATT GGC AAA GAA TGG ATT CTA ACT GCT GCG CAT TGT GTA ACC        142
Ser Ile Ile Gly Lys Glu Trp Ile Leu Thr Ala Ala His Cys Val Thr
        35                  40                  45

AAA TAT GAA AAC GAT ATC GAA GGT TTA AAA GTT AGG GTT GGA ANC AAT        190
Lys Tyr Glu Asn Asp Ile Glu Gly Leu Lys Val Arg Val Gly Xaa Asn
    50                  55                  60

GAG CAT AAC AAA GGT GGG CGT TTA TAC GAC ATT AAA GAA ATT AAA AAA        238
Glu His Asn Lys Gly Gly Arg Leu Tyr Asp Ile Lys Glu Ile Lys Lys
65                  70                  75

CAT CCA AGA TAT AAC GAT CGA ACC AGA TAC GAT TTT GAT GTC GCT TTA        286
His Pro Arg Tyr Asn Asp Arg Thr Arg Tyr Asp Phe Asp Val Ala Leu
    80                  85                  90                  95

TTA CGC ATT GCA AAG CCA ATT GCA TAC ACT GCT TGC ACT GTT GTT CCT        334
Leu Arg Ile Ala Lys Pro Ile Ala Tyr Thr Ala Cys Thr Val Val Pro
                100                 105                 110

GTA GCA TTG GCA GAA ACT GGA AAA GAA GTT CCA GAA GGC GCA CTC GTT        382
Val Ala Leu Ala Glu Thr Gly Lys Glu Val Pro Glu Gly Ala Leu Val
            115                 120                 125

AGT GTC ACA GGA TGG GGG GCT ACT ATG GTG GGC GGC CCA GCA TCA ACG        430
Ser Val Thr Gly Trp Gly Ala Thr Met Val Gly Gly Pro Ala Ser Thr
```

```
                130                 135                 140
CAT CTA AAA GGT GTT AAG GTT CCA ATC GTG TCA AAT GAA GAA TGC AAC    478
His Leu Lys Gly Val Lys Val Pro Ile Val Ser Asn Glu Glu Cys Asn
    145                 150                 155

AAA AAT TAT ACC ATT CCT GGA GGT CTG GAT GAC AAA ATT TCA GAC AGC    526
Lys Asn Tyr Thr Ile Pro Gly Gly Leu Asp Asp Lys Ile Ser Asp Ser
160                 165                 170                 175

ATG TTT TGC GCT GGT TTC CCT GAA GGC GGA AAG GAC TCG TGT CAA GGA    574
Met Phe Cys Ala Gly Phe Pro Glu Gly Gly Lys Asp Ser Cys Gln Gly
                180                 185                 190

GAT AGC GGT GGG CCT GTA GTG GAT GAA AAT AGG GTT CAG GTC GGA ATT    622
Asp Ser Gly Gly Pro Val Val Asp Glu Asn Arg Val Gln Val Gly Ile
            195                 200                 205

GTG TNT TGG GGC GAA GGC TGT GCT TTA GCA GGA AAA CCA GGC GTT TAT    670
Val Xaa Trp Gly Glu Gly Cys Ala Leu Ala Gly Lys Pro Gly Val Tyr
        210                 215                 220

GCA AAA GTT TCA CAT CCT GAC GTA AAA AGG TTT ATT GAA ACC GTA GCA    718
Ala Lys Val Ser His Pro Asp Val Lys Arg Phe Ile Glu Thr Val Ala
    225                 230                 235

GGA ATC AAA T AAAATTTGTT AGAAAAAATG TAGACAAGTT GTATAAACTN          768
Gly Ile Lys
240

TCAATGAAAT TGTTTTATTT TTGGAAATAA AATATAATTT NTGAAAAAAA AAAAAAAAA    828

AAAAAAAAAA AAA                                                      841

(2) INFORMATION FOR SEQ ID NO:41:

(i) SEQUENCE CHARACTERISTICS:
        (A) LENGTH: 242 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 62

(ix) FEATURE:
        (A) NAME/KEY: Xaa = any amino acid
        (B) LOCATION: 209

(xi) SEQUENCE DESCRIPTION: SEQ ID NO:41:

Asp His Arg Ile Val Gly Gly Glu Asp Val Asp Ile Ser Thr Cys Gly
  1               5                  10                  15

Trp Gln Val Ser Phe His Asn Arg Lys Gly His Phe Cys Gly Gly Ser
             20                  25                  30

Ile Ile Gly Lys Glu Trp Ile Leu Thr Ala Ala His Cys Val Thr Lys
         35                  40                  45

Tyr Glu Asn Asp Ile Glu Gly Leu Lys Val Arg Val Gly Xaa Asn Glu
     50                  55                  60

His Asn Lys Gly Gly Arg Leu Tyr Asp Ile Lys Glu Ile Lys Lys His
 65                  70                  75                  80

Pro Arg Tyr Asn Asp Arg Thr Arg Tyr Asp Phe Asp Val Ala Leu Leu
                 85                  90                  95

Arg Ile Ala Lys Pro Ile Ala Tyr Thr Ala Cys Thr Val Val Pro Val
            100                 105                 110

Ala Leu Ala Glu Thr Gly Lys Glu Val Pro Glu Gly Ala Leu Val Ser
        115                 120                 125

Val Thr Gly Trp Gly Ala Thr Met Val Gly Gly Pro Ala Ser Thr His
```

```
                130                 135                 140
Leu Lys Gly Val Lys Val Pro Ile Val Ser Asn Glu Glu Cys Asn Lys
145                 150                 155                 160

Asn Tyr Thr Ile Pro Gly Gly Leu Asp Asp Lys Ile Ser Asp Ser Met
                165                 170                 175

Phe Cys Ala Gly Phe Pro Glu Gly Gly Lys Asp Ser Cys Gln Gly Asp
            180                 185                 190

Ser Gly Gly Pro Val Val Asp Glu Asn Arg Val Gln Val Gly Ile Val
        195                 200                 205

Xaa Trp Gly Glu Gly Cys Ala Leu Ala Gly Lys Pro Gly Val Tyr Ala
        210                 215                 220

Lys Val Ser His Pro Asp Val Lys Arg Phe Ile Glu Thr Val Ala Gly
225                 230                 235                 240

Ile Lys
```

(2) INFORMATION FOR SEQ ID NO:42:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
TTTTTTTTTT TTTTTTTTTT TTTTTTTTTT CANAAATTAT ATTTTATTTC CAAAAATAAA    60
ACAATTTCAT TGANAGTTTA TACAACTTGT CTACATTTTT TCTAACAAAT TTATTTGAT    120
TCCTGCTACG GTTTCAATAA ACCTTTTTAC GTCAGGATGT GAAACTTTTG CATAAACGCC   180
TGGTTTTCCT GCTAAAGCAC AGCCTTCGCC CCAANACACA ATTCCGACCT GAACCCTATT   240
TTCATCCACT ACAGGCCCAC CGCTATCTCC TTGACACGAG TCCTTTCCGC CTTCAGGGAA   300
ACCAGCGCAA AACATGCTGT CTGAAATTTT GTCATCCAGA CCTCCAGGAA TGGTATAATT   360
TTTGTTGCAT TCTTCATTTG ACACGATTGG AACCTTAACA CCTTTTAGAT GCGTTGATGC   420
TGGGCCGCCC ACCATAGTAG CCCCCCATCC TGTGACACTA ACGAGTGCGC CTTCTGGAAC   480
TTCTTTTCCA GTTTCTGCCA ATGCTACAGG AACAACAGTG CAAGCAGTGT ATGCAATTGG   540
CTTTGCAATG CGTAATAAAG CGACATCAAA ATCGTATCTG GTTCGATCGT TATATCTTGG   600
ATGTTTTTA ATTTCTTTAA TGTCGTATAA ACGCCCACCT TTGTTATGCT CATTGNTTCC    660
AACCCTAACT TTTAAACCTT CGATATCGTT TTCATATTTG GTTACACAAT GCGCAGCAGT   720
TAGAATCCAT TCTTTGCCAA TGATGGACCC TCCACAAAAA TGTCCTTTCC TATTGTGAAA   780
CGAAACTTGC CATCCACAAG TTGAAATATC TACATCTTCA CCTCCTACTA TTCGATGATC   840
T                                                                   841
```

(2) INFORMATION FOR SEQ ID NO:43:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..717

(ix) FEATURE:
    (A) NAME/KEY: Xaa = any amino acid
    (B) LOCATION: 59

(ix) FEATURE:
    (A) NAME/KEY: Xaa = any amino acid
    (B) LOCATION: 206

(xi) SEQUENCE DESCRIPTION: SEQ ID NO:43:

```
ATA GTA GGA GGT GAA GAT GTA GAT ATT TCA ACT TGT GGA TGG CAA GTT        48
Ile Val Gly Gly Glu Asp Val Asp Ile Ser Thr Cys Gly Trp Gln Val
 1               5                  10                  15

TCG TTT CAC AAT AGG AAA GGA CAT TTT TGT GGA GGG TCC ATC ATT GGC        96
Ser Phe His Asn Arg Lys Gly His Phe Cys Gly Gly Ser Ile Ile Gly
             20                  25                  30

AAA GAA TGG ATT CTA ACT GCT GCG CAT TGT GTA ACC AAA TAT GAA AAC       144
Lys Glu Trp Ile Leu Thr Ala Ala His Cys Val Thr Lys Tyr Glu Asn
         35                  40                  45

GAT ATC GAA GGT TTA AAA GTT AGG GTT GGA ANC AAT GAG CAT AAC AAA       192
Asp Ile Glu Gly Leu Lys Val Arg Val Gly Xaa Asn Glu His Asn Lys
     50                  55                  60

GGT GGG CGT TTA TAC GAC ATT AAA GAA ATT AAA AAA CAT CCA AGA TAT       240
Gly Gly Arg Leu Tyr Asp Ile Lys Glu Ile Lys Lys His Pro Arg Tyr
 65                  70                  75                  80

AAC GAT CGA ACC AGA TAC GAT TTT GAT GTC GCT TTA TTA CGC ATT GCA       288
Asn Asp Arg Thr Arg Tyr Asp Phe Asp Val Ala Leu Leu Arg Ile Ala
                 85                  90                  95

AAG CCA ATT GCA TAC ACT GCT TGC ACT GTT GTT CCT GTA GCA TTG GCA       336
Lys Pro Ile Ala Tyr Thr Ala Cys Thr Val Val Pro Val Ala Leu Ala
            100                 105                 110

GAA ACT GGA AAA GAA GTT CCA GAA GGC GCA CTC GTT AGT GTC ACA GGA       384
Glu Thr Gly Lys Glu Val Pro Glu Gly Ala Leu Val Ser Val Thr Gly
        115                 120                 125

TGG GGG GCT ACT ATG GTG GGC GGC CCA GCA TCA ACG CAT CTA AAA GGT       432
Trp Gly Ala Thr Met Val Gly Gly Pro Ala Ser Thr His Leu Lys Gly
    130                 135                 140

GTT AAG GTT CCA ATC GTG TCA AAT GAA GAA TGC AAC AAA AAT TAT ACC       480
Val Lys Val Pro Ile Val Ser Asn Glu Glu Cys Asn Lys Asn Tyr Thr
145                 150                 155                 160

ATT CCT GGA GGT CTG GAT GAC AAA ATT TCA GAC AGC ATG TTT TGC GCT       528
Ile Pro Gly Gly Leu Asp Asp Lys Ile Ser Asp Ser Met Phe Cys Ala
                165                 170                 175

GGT TTC CCT GAA GGC GGA AAG GAC TCG TGT CAA GGA GAT AGC GGT GGG       576
Gly Phe Pro Glu Gly Gly Lys Asp Ser Cys Gln Gly Asp Ser Gly Gly
            180                 185                 190

CCT GTA GTG GAT GAA AAT AGG GTT CAG GTC GGA ATT GTG TNT TGG GGC       624
Pro Val Val Asp Glu Asn Arg Val Gln Val Gly Ile Val Xaa Trp Gly
        195                 200                 205

GAA GGC TGT GCT TTA GCA GGA AAA CCA GGC GTT TAT GCA AAA GTT TCA       672
Glu Gly Cys Ala Leu Ala Gly Lys Pro Gly Val Tyr Ala Lys Val Ser
    210                 215                 220

CAT CCT GAC GTA AAA AGG TTT ATT GAA ACC GTA GCA GGA ATC AAA           717
His Pro Asp Val Lys Arg Phe Ile Glu Thr Val Ala Gly Ile Lys
225                 230                 235
```

(2) INFORMATION FOR SEQ ID NO:44:

(i) SEQUENCE CHARACTERISTICS:
        (A) LENGTH: 239 amino acids
        (B) TYPE: amino acid
        (D) TOPOLOGY: linear (ii) MOLECULE TYPE: protein (ix) FEATURE:
    (A) NAME/KEY: Xaa = any amino acid
    (B) LOCATION: 59

(ix) FEATURE:
    (A) NAME/KEY: Xaa = any amino acid
    (B) LOCATION: 206

(xi) SEQUENCE DESCRIPTION: SEQ ID NO:44:

```
Ile Val Gly Gly Glu Asp Val Asp Ile Ser Thr Cys Gly Trp Gln Val
 1               5                  10                  15

Ser Phe His Asn Arg Lys Gly His Phe Cys Gly Gly Ser Ile Ile Gly
                20                  25                  30

Lys Glu Trp Ile Leu Thr Ala Ala His Cys Val Thr Lys Tyr Glu Asn
            35                  40                  45

Asp Ile Glu Gly Leu Lys Val Arg Val Gly Xaa Asn Glu His Asn Lys
        50                  55                  60

Gly Gly Arg Leu Tyr Asp Ile Lys Glu Ile Lys Lys His Pro Arg Tyr
65                  70                  75                  80

Asn Asp Arg Thr Arg Tyr Asp Phe Asp Val Ala Leu Leu Arg Ile Ala
                85                  90                  95

Lys Pro Ile Ala Tyr Thr Ala Cys Thr Val Pro Val Ala Leu Ala
            100                 105                 110

Glu Thr Gly Lys Glu Val Pro Glu Gly Ala Leu Val Ser Val Thr Gly
        115                 120                 125

Trp Gly Ala Thr Met Val Gly Gly Pro Ala Ser Thr His Leu Lys Gly
130                 135                 140

Val Lys Val Pro Ile Val Ser Asn Glu Glu Cys Asn Lys Asn Tyr Thr
145                 150                 155                 160

Ile Pro Gly Gly Leu Asp Asp Lys Ile Ser Asp Ser Met Phe Cys Ala
                165                 170                 175

Gly Phe Pro Glu Gly Gly Lys Asp Ser Cys Gln Gly Asp Ser Gly Gly
            180                 185                 190

Pro Val Val Asp Glu Asn Arg Val Gln Val Gly Ile Val Xaa Trp Gly
        195                 200                 205

Glu Gly Cys Ala Leu Ala Gly Lys Pro Gly Val Tyr Ala Lys Val Ser
210                 215                 220

His Pro Asp Val Lys Arg Phe Ile Glu Thr Val Ala Gly Ile Lys
225                 230                 235
```

(2) INFORMATION FOR SEQ ID NO:45:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
TTTGATTCCT GCTACGGTTT CAATAAACCT TTTTACGTCA GGATGTGAAA CTTTTGCATA      60

AACGCCTGGT TTTCCTGCTA AAGCACAGCC TTCGCCCCAA NACACAATTC CGACCTGAAC     120

CCTATTTTCA TCCACTACAG GCCCACCGCT ATCTCCTTGA CACGAGTCCT TTCCGCCTTC     180

AGGGAAACCA GCGCAAAACA TGCTGTCTGA AATTTTGTCA TCCAGACCTC CAGGAATGGT     240

ATAATTTTTG TTGCATTCTT CATTTGACAC GATTGGAACC TTAACACCTT TTAGATGCGT     300
```

```
TGATGCTGGG CCGCCCACCA TAGTAGCCCC CCATCCTGTG ACACTAACGA GTGCGCCTTC    360

TGGAACTTCT TTTCCAGTTT CTGCCAATGC TACAGGAACA ACAGTGCAAG CAGTGTATGC    420

AATTGGCTTT GCAATGCGTA ATAAAGCGAC ATCAAAATCG TATCTGGTTC GATCGTTATA    480

TCTTGGATGT TTTTTAATTT CTTTAATGTC GTATAAACGC CCACCTTTGT TATGCTCATT    540

GNTTCCAACC CTAACTTTTA AACCTTCGAT ATCGTTTTCA TATTTGGTTA CACAATGCGC    600

AGCAGTTAGA ATCCATTCTT TGCCAATGAT GGACCCTCCA CAAAAATGTC CTTTCCTATT    660

GTGAAACGAA ACTTGCCATC CACAAGTTGA AATATCTACA TCTTCACCTC CTACTAT      717
```

(2) INFORMATION FOR SEQ ID NO:46:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (primer)

(xi) SEQUENCE DESCRIPTION: SEQ ID NO:46:

```
GGACAAACTG TTCATTGCAG                                                 20
```

(2) INFORMATION FOR SEQ ID NO:47:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (primer)

(xi) SEQUENCE DESCRIPTION: SEQ ID NO:47:

```
CCCTCATTTG TCGTAACTCC                                                 20
```

(2) INFORMATION FOR SEQ ID NO:48:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (primer)

(xi) SEQUENCE DESCRIPTION: SEQ ID NO:48:

```
GGCTAGGTTA GTGGATTCTG G                                               21
```

(2) INFORMATION FOR SEQ ID NO:49:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: DNA (primer)

(xi) SEQUENCE DESCRIPTION: SEQ ID NO:49:

```
GCAAATCAGT TCCAGAATCC ACTAACC                                         27
```

(2) INFORMATION FOR SEQ ID NO:50:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:50:

CAGGGCGCTC TGCAGAACGC AAC                                           23

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:51:

ATTCCTCGTG GTTCAGTCGC TC                                            22

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:52:

GGCAAGTTTC GTTTCACAAT AGG                                           23

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:53:

TCCAACCCTA ACTTTTAAAC CTTC                                          24

(2) INFORMATION FOR SEQ ID NO:54:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:54:

CACAGGATCC AATAATTTGT GGTCAAAATG C                                  31

(2) INFORMATION FOR SEQ ID NO:55:

(i) SEQUENCE CHARACTERISTICS:
        (A) LENGTH: 37 base pairs
        (B) TYPE: nucleic acid
        (C) STRANDEDNESS: single
        (D) TOPOLOGY: linear

```
    (ii) MOLECULE TYPE: DNA (primer)

(xi) SEQUENCE DESCRIPTION: SEQ ID NO:55:

AAAAAGAAAG CTTCTTTAAT TTTCTGACAT TGTCGTG                              37

(2) INFORMATION FOR SEQ ID NO:56:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:56:

GCGGGATCCT ATTGTGGGTG GTGAAGCAGT G                                    31

(2) INFORMATION FOR SEQ ID NO:57:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:57:

GACGGTACCA TGTATAAAAT AATATTAAAC TCCGG                                35

(2) INFORMATION FOR SEQ ID NO:58:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:58:

CCGGGATCCT ATGTTAGCGA TCGTCCCGTC AAAC                                 34

(2) INFORMATION FOR SEQ ID NO:59:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:59:

CCGGAATTCT TATCCCATTA CTTTGTCGAT CC                                   32

(2) INFORMATION FOR SEQ ID NO:60:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:60:
```

```
GCGGGATCCA ATAGTAGGAG GTGAAGATGT AG                                    32
```

(2) INFORMATION FOR SEQ ID NO:61:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:61:

```
CCGGAATTCT CTAACAAAT TTTATTTGAT TCCTGC                                 36
```

(2) INFORMATION FOR SEQ ID NO:62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:62:

```
GGATCCAATC GTTGGAGGTG AAGATG                                           26
```

(2) INFORMATION FOR SEQ ID NO:63:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:63:

```
GAATTCGAAA TCCACTTAAA CATTAGC                                          27
```

(2) INFORMATION FOR SEQ ID NO:64:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:64:

```
GATAAGGATC CGTTACCAGA TTCTTTCGAC TGG                                   33
```

(2) INFORMATION FOR SEQ ID NO:65:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:65:

```
TTATCAAGCT TCCATTTACA TGCCGTAAAA ATC                                   33
```

(2) INFORMATION FOR SEQ ID NO:66:

(i) SEQUENCE CHARACTERISTICS:
        (A) LENGTH: 923 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..802

(xi) SEQUENCE DESCRIPTION: SEQ ID NO:66:

```
A TTA ACA ATG ATG AAA CTT TTG GTA GTT TTT GCG ATT TTC GCT CAA        46
  Leu Thr Met Met Lys Leu Leu Val Val Phe Ala Ile Phe Ala Gln
   1               5                  10                  15

ATC AGT TTT GTT TTT GGA AAT AAT GTA ACA GAA TTC GAT GAC CGA ATC      94
Ile Ser Phe Val Phe Gly Asn Asn Val Thr Glu Phe Asp Asp Arg Ile
                 20                  25                  30

GTT GGA GGT GAA GAT GTT GAT ATA TCA ACT TGT GGT TGG CAA ATT TCA     142
Val Gly Gly Glu Asp Val Asp Ile Ser Thr Cys Gly Trp Gln Ile Ser
             35                  40                  45

TTT CAA AGT GAA AAC CTT CAT TTT TGT GGA GGA TCA ATT ATT GCA CCA     190
Phe Gln Ser Glu Asn Leu His Phe Cys Gly Gly Ser Ile Ile Ala Pro
         50                  55                  60

AAA TGG ATT CTA ACT GCT GCA CAC TGT GTT GAA TGG TTG AAA AAG CCG     238
Lys Trp Ile Leu Thr Ala Ala His Cys Val Glu Trp Leu Lys Lys Pro
     65                  70                  75

CTC AAA GAC ATA ACC GTA CGT ATA GGA AGC AGT ATA CGT AAC AAA GGT     286
Leu Lys Asp Ile Thr Val Arg Ile Gly Ser Ser Ile Arg Asn Lys Gly
 80                  85                  90                  95

GGT CGA GTT CAT AAA GTA ATA GAT TTC CAC ATG CAT CCC TCG TAC AAT     334
Gly Arg Val His Lys Val Ile Asp Phe His Met His Pro Ser Tyr Asn
                100                 105                 110

AAG AGG GCG GAT TAT GAT TTT GAC GTT GCT GTA CTA GAA CTT GAA AAA     382
Lys Arg Ala Asp Tyr Asp Phe Asp Val Ala Val Leu Glu Leu Glu Lys
            115                 120                 125

CCA GTC TCA TAT ACG GTT TGT ACA GTA GTA TCA GTA GAT TTA GCC GAA     430
Pro Val Ser Tyr Thr Val Cys Thr Val Val Ser Val Asp Leu Ala Glu
        130                 135                 140

AGT GGA ACT GAA GTT AAA CCT GGA GCA ATA CTT AGT GTC ACT GGA TGG     478
Ser Gly Thr Glu Val Lys Pro Gly Ala Ile Leu Ser Val Thr Gly Trp
    145                 150                 155

GGT GCA ACT AAG GAA GGT GGT GGC GGA ACT TTG CAA CTA CAA GGT GTG     526
Gly Ala Thr Lys Glu Gly Gly Gly Gly Thr Leu Gln Leu Gln Gly Val
160                 165                 170                 175

AAA GTT CCA GCT ATC TCT CCC AAA GAT TGT GCT AAG GGA TAT CCA CCT     574
Lys Val Pro Ala Ile Ser Pro Lys Asp Cys Ala Lys Gly Tyr Pro Pro
                180                 185                 190

TCT GGA GGT AAA GAC AAA ATT ACA GAC AGC ATG TTA TGT GCT GGT CTT     622
Ser Gly Gly Lys Asp Lys Ile Thr Asp Ser Met Leu Cys Ala Gly Leu
            195                 200                 205

CCT GAA GGA GGT AAA GAT TCC TGC CAA GGC GAC AGT GGC GGT CCA CTG     670
Pro Glu Gly Gly Lys Asp Ser Cys Gln Gly Asp Ser Gly Gly Pro Leu
        210                 215                 220

GTA GAT GAA AAT AGA AAG CAA GTA GGA GTG GTT TCT TGG GGT CAA GGA     718
Val Asp Glu Asn Arg Lys Gln Val Gly Val Val Ser Trp Gly Gln Gly
    225                 230                 235

TGT GCC AGA CCA GGA AAA CCA GGA ATT TAT GCT AAA GTG TCA CAC CCC     766
Cys Ala Arg Pro Gly Lys Pro Gly Ile Tyr Ala Lys Val Ser His Pro
240                 245                 250                 255
```

```
GAA ATC AGA AAA TTT ATT GAA AAA TAT GCT AAT GTT TAAGTGGATT          812
Glu Ile Arg Lys Phe Ile Glu Lys Tyr Ala Asn Val
            260                 265

TCATTTTCAA TATAATGTGA TTTAAGATAC TCTTTAATGT TATGATATGA ATTGTGATAA   872

ATTAAATAAT AAAGATTGAA GAAGTGATAA AAAAAAAAAA AAAAAAAAAA A            923

(2) INFORMATION FOR SEQ ID NO:67:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO:67:

Leu Thr Met Met Lys Leu Leu Val Val Phe Ala Ile Phe Ala Gln Ile
 1               5                  10                  15

Ser Phe Val Phe Gly Asn Asn Val Thr Glu Phe Asp Asp Arg Ile Val
            20                  25                  30

Gly Gly Glu Asp Val Asp Ile Ser Thr Cys Gly Trp Gln Ile Ser Phe
        35                  40                  45

Gln Ser Glu Asn Leu His Phe Cys Gly Ser Ile Ile Ala Pro Lys
    50                  55                  60

Trp Ile Leu Thr Ala Ala His Cys Val Glu Trp Leu Lys Lys Pro Leu
65                  70                  75                  80

Lys Asp Ile Thr Val Arg Ile Gly Ser Ser Ile Arg Asn Lys Gly Gly
                85                  90                  95

Arg Val His Lys Val Ile Asp Phe His Met His Pro Ser Tyr Asn Lys
            100                 105                 110

Arg Ala Asp Tyr Asp Phe Asp Val Ala Val Leu Glu Leu Glu Lys Pro
        115                 120                 125

Val Ser Tyr Thr Val Cys Thr Val Ser Val Asp Leu Ala Glu Ser
    130                 135                 140

Gly Thr Glu Val Lys Pro Gly Ala Ile Leu Ser Val Thr Gly Trp Gly
145                 150                 155                 160

Ala Thr Lys Glu Gly Gly Gly Thr Leu Gln Leu Gln Gly Val Lys
                165                 170                 175

Val Pro Ala Ile Ser Pro Lys Asp Cys Ala Lys Gly Tyr Pro Pro Ser
            180                 185                 190

Gly Gly Lys Asp Lys Ile Thr Asp Ser Met Leu Cys Ala Gly Leu Pro
        195                 200                 205

Glu Gly Gly Lys Asp Ser Cys Gln Gly Asp Ser Gly Pro Leu Val
    210                 215                 220

Asp Glu Asn Arg Lys Gln Val Gly Val Val Ser Trp Gly Gln Gly Cys
225                 230                 235                 240

Ala Arg Pro Gly Lys Pro Gly Ile Tyr Ala Lys Val Ser His Pro Glu
                245                 250                 255

Ile Arg Lys Phe Ile Glu Lys Tyr Ala Asn Val
            260                 265

(2) INFORMATION FOR SEQ ID NO:68:

(i) SEQUENCE CHARACTERISTICS:
        (A) LENGTH: 15 amino acids
        (B) TYPE: amino acid
        (C) STRANDEDNESS:
```

(D) TOPOLOGY: linear (ii) MOLECULE TYPE: protein (xi) SEQUENCE DESCRIPTION: SEQ ID NO:68:

Ile Val Gly Gly Glu Asp Val Asp Ile Ser Thr Cys Gly Trp Cys
1               5                   10                  15

(2) INFORMATION FOR SEQ ID NO:69:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:69:

Ile Val Gly Gly Glu Asp Val Asp Ile Ser Thr Cys Gly Trp Gln Ile
1               5                   10                  15

Ser Phe Gln Ser Glu Asn Leu His Phe Cys Gly Gly Ser Ile Ile Ala
            20                  25                  30

Pro Lys (2) INFORMATION FOR SEQ ID NO:70:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Xaa = His or Arg
        (B) LOCATION: 1

(ix) FEATURE:
        (A) NAME/KEY: Xaa = Val or Pro
        (B) LOCATION: 2

(ix) FEATURE:
        (A) NAME/KEY: Xaa = Gly or Ala or Ser
        (B) LOCATION: 3

(ix) FEATURE:
        (A) NAME/KEY: Xaa = Tyr or Gly
        (B) LOCATION: 4

(ix) FEATURE:
        (A) NAME/KEY: Xaa = Glu or Asn
        (B) LOCATION: 5

(ix) FEATURE:
        (A) NAME/KEY: Xaa = Asp or Lys
        (B) LOCATION: 6

(ix) FEATURE:
        (A) NAME/KEY: Xaa = Val or Arg
        (B) LOCATION: 7

(ix) FEATURE:
        (A) NAME/KEY: Xaa = Asp or Ala
        (B) LOCATION: 8

(ix) FEATURE:
        (A) NAME/KEY: Xaa = Asp or Pro
        (B) LOCATION: 13

(xi) SEQUENCE DESCRIPTION: SEQ ID NO:70:

```
Xaa Xaa Xaa Xaa Xaa Xaa Xaa Xaa Asp Tyr Asp Phe Xaa Val Ala
1               5                   10                  15
```

(2) INFORMATION FOR SEQ ID NO:71:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Xaa = Ile or Gln
        (B) LOCATION: 1

(ix) FEATURE:
        (A) NAME/KEY: Xaa = Tyr or Gly
        (B) LOCATION: 4

(ix) FEATURE:
        (A) NAME/KEY: Xaa = Glu or Asn or Thr
        (B) LOCATION: 5

(ix) FEATURE:
        (A) NAME/KEY: Xaa = Asp or Met or Pro
        (B) LOCATION: 6

(ix) FEATURE:
        (A) NAME/KEY: Xaa = Lys or Asp
        (B) LOCATION: 8

(ix) FEATURE:
        (A) NAME/KEY: Xaa = Asn or Ser
        (B) LOCATION: 10

(ix) FEATURE:
        (A) NAME/KEY: Xaa = Met or Thr or Asn
        (B) LOCATION: 11

(ix) FEATURE:
        (A) NAME/KEY: Xaa = Phe or Cys
        (B) LOCATION: 12

(xi) SEQUENCE DESCRIPTION: SEQ ID NO:71:

```
Xaa Val Gly Xaa Xaa Xaa Val Xaa Ile Xaa Xaa Xaa
1               5                   10
```

(2) INFORMATION FOR SEQ ID NO:72:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Xaa = His or Arg
        (B) LOCATION: 1

(ix) FEATURE:
        (A) NAME/KEY: Xaa = Ala or Ser
        (B) LOCATION: 3

(xi) SEQUENCE DESCRIPTION: SEQ ID NO:72:

```
Xaa Pro Xaa Tyr Asn Lys Arg Ala Asp Tyr Asp Phe Asp Val Ala
1               5                   10                  15
```

(2) INFORMATION FOR SEQ ID NO:73:

(i) SEQUENCE CHARACTERISTICS:

(A) LENGTH: 28 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Xaa = probably Cys
        (B) LOCATION: 1

(xi) SEQUENCE DESCRIPTION: SEQ ID NO:73:

Xaa Pro Pro Pro Glu Met Leu Gly Gly Pro Ser Ile Phe Ile Phe Pro
1               5                  10                  15

Pro Lys Pro Lys Asp Asp Leu Leu Ile Lys Arg Lys
            20                  25

(2) INFORMATION FOR SEQ ID NO:74:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:74:

CTTTCCTCAC AATACCACCA AGGAAGC                                              27

(2) INFORMATION FOR SEQ ID NO:75:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:75:

CTTGTACGAT TGTCTCAACA GGC                                                  23

(2) INFORMATION FOR SEQ ID NO:76:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO:76:

CGA TCT TTT AGA CAA GCG AAA TTG ATA ACG AAG TTT TCG AAG TCG GAT           48
Arg Ser Phe Arg Gln Ala Lys Leu Ile Thr Lys Phe Ser Lys Ser Asp
1               5                  10                  15

GAA GTA AAA ACC TTG CGT TGG TTT CCC CGG TCC CAG GAT CAG GAA CAG           96
Glu Val Lys Thr Leu Arg Trp Phe Pro Arg Ser Gln Asp Gln Glu Gln
            20                  25                  30

TTG CAC TTT ACC CCA ATG AGG GAA TTC GTG CAT CCC CAT TTT ACC GAA          144
Leu His Phe Thr Pro Met Arg Glu Phe Val His Pro His Phe Thr Glu
        35                  40                  45

CAT ATT GAT GAA GAA TTC CAC CGA TTC ATC AAT AAA CAC GGA AAA ATT          192

```
His Ile Asp Glu Glu Phe His Arg Phe Ile Asn Lys His Gly Lys Ile
     50                  55                  60

TAT AAT AAA AAT GAA GAA CAT CAT TTC CGC AAA GAA ATT TTC AGA CTA        240
Tyr Asn Lys Asn Glu Glu His His Phe Arg Lys Glu Ile Phe Arg Leu
 65                  70                  75                  80

AAC TTG AGG TAC ATT TTT TCT AAG AAT CGT GCA AAT TTG GGA TAC ACT        288
Asn Leu Arg Tyr Ile Phe Ser Lys Asn Arg Ala Asn Leu Gly Tyr Thr
                 85                  90                  95

TTG ACT GTT AAC CAT TTG GCT GAT CGT ACT GAA GCT GAA CTT AAG GCT        336
Leu Thr Val Asn His Leu Ala Asp Arg Thr Glu Ala Glu Leu Lys Ala
            100                 105                 110

TTG AGA GGA CAC AGA CCT TCC TCC GGT TAT AAT GGC GGT TTA CCC TTT        384
Leu Arg Gly His Arg Pro Ser Ser Gly Tyr Asn Gly Gly Leu Pro Phe
        115                 120                 125

CCT CAC AAT ACC ACC AAG GAA GCA AGA AAT TTA CCA GAT TCT TTC GAC        432
Pro His Asn Thr Thr Lys Glu Ala Arg Asn Leu Pro Asp Ser Phe Asp
    130                 135                 140

TGG CGA ATT TAT GGA GCT GTT ACT CCA GTT AAA GAT CAA TCT GTT TGT        480
Trp Arg Ile Tyr Gly Ala Val Thr Pro Val Lys Asp Gln Ser Val Cys
145                 150                 155                 160

GGT TCC TGC TGG TCT TTC GGA ACA ATT GGA GCA ATC GAA GGT GCA TAT        528
Gly Ser Cys Trp Ser Phe Gly Thr Ile Gly Ala Ile Glu Gly Ala Tyr
                165                 170                 175

TTC TTG AAA ACG GCG GTA ATC TGT ACG ATG TCT CAC AGC TTG ATG            573
Phe Leu Lys Thr Ala Val Ile Cys Thr Met Ser His Ser Leu Met
            180                 185                 190
```

(2) INFORMATION FOR SEQ ID NO:77:

(i) SEQUENCE CHARACTERISTICS:
      (A) LENGTH: 191 amino acids
      (B) TYPE: amino acid
      (D) TOPOLOGY: linear (ii) MOLECULE TYPE: protein (xi) SEQUENCE DESCRIPTION: SEQ ID NO:77:

```
Arg Ser Phe Arg Gln Ala Lys Leu Ile Thr Lys Phe Ser Lys Ser Asp
 1               5                  10                  15

Glu Val Lys Thr Leu Arg Trp Phe Pro Arg Ser Gln Asp Gln Glu Gln
            20                  25                  30

Leu His Phe Thr Pro Met Arg Glu Phe Val His Pro Phe Thr Glu
        35                  40                  45

His Ile Asp Glu Glu Phe His Arg Phe Ile Asn Lys His Gly Lys Ile
     50                  55                  60

Tyr Asn Lys Asn Glu Glu His His Phe Arg Lys Glu Ile Phe Arg Leu
 65                  70                  75                  80

Asn Leu Arg Tyr Ile Phe Ser Lys Asn Arg Ala Asn Leu Gly Tyr Thr
                 85                  90                  95

Leu Thr Val Asn His Leu Ala Asp Arg Thr Glu Ala Glu Leu Lys Ala
            100                 105                 110

Leu Arg Gly His Arg Pro Ser Ser Gly Tyr Asn Gly Gly Leu Pro Phe
        115                 120                 125

Pro His Asn Thr Thr Lys Glu Ala Arg Asn Leu Pro Asp Ser Phe Asp
    130                 135                 140

Trp Arg Ile Tyr Gly Ala Val Thr Pro Val Lys Asp Gln Ser Val Cys
145                 150                 155                 160

Gly Ser Cys Trp Ser Phe Gly Thr Ile Gly Ala Ile Glu Gly Ala Tyr
                165                 170                 175
```

Phe Leu Lys Thr Ala Val Ile Cys Thr Met Ser His Ser Leu Met
        180                 185                 190

(2) INFORMATION FOR SEQ ID NO:78:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..408

(xi) SEQUENCE DESCRIPTION: SEQ ID NO:78:

| TGG | GTT | GTT | ACT | GCT | GCT | CAT | TGT | TTG | AGA | GGC | AAA | GAC | CAC | CTC | CTG | 48 |
| Trp | Val | Val | Thr | Ala | Ala | His | Cys | Leu | Arg | Gly | Lys | Asp | His | Leu | Leu | |
| 1 | | | | 5 | | | | | 10 | | | | | 15 | | |

| GAC | AAA | CTG | TTC | ATT | GCA | GTC | GGC | CTG | ACA | AAT | TTA | GGT | GAA | GGA | GGC | 96 |
| Asp | Lys | Leu | Phe | Ile | Ala | Val | Gly | Leu | Thr | Asn | Leu | Gly | Glu | Gly | Gly | |
| | | | 20 | | | | | 25 | | | | | 30 | | | |

| ACC | GTG | TAT | CCT | GTA | GAA | AAA | GGC | ATC | ATG | CAC | GAA | GAA | TAT | GAA | CAT | 144 |
| Thr | Val | Tyr | Pro | Val | Glu | Lys | Gly | Ile | Met | His | Glu | Glu | Tyr | Glu | His | |
| | | 35 | | | | | 40 | | | | | 45 | | | | |

| TAT | GAC | ATA | GTC | AAC | GAT | ATT | GCA | CTA | ATC | AAA | GTC | AAA | TCT | CCG | ATA | 192 |
| Tyr | Asp | Ile | Val | Asn | Asp | Ile | Ala | Leu | Ile | Lys | Val | Lys | Ser | Pro | Ile | |
| 50 | | | | | 55 | | | | | 60 | | | | | | |

| GAA | TTC | AAT | GAA | AAA | GTA | ACG | ACT | GTA | AAA | TTA | GGT | GAG | GAT | TAT | GTT | 240 |
| Glu | Phe | Asn | Glu | Lys | Val | Thr | Thr | Val | Lys | Leu | Gly | Glu | Asp | Tyr | Val | |
| 65 | | | | | 70 | | | | | 75 | | | | | 80 | |

| GGC | GGA | GAC | GTC | CAA | CTT | CGA | TTG | ACA | GGA | TGG | GGA | GTT | ACG | ACA | AAT | 288 |
| Gly | Gly | Asp | Val | Gln | Leu | Arg | Leu | Thr | Gly | Trp | Gly | Val | Thr | Thr | Asn | |
| | | | | 85 | | | | | 90 | | | | | 95 | | |

| GAG | GGA | ATC | GGA | AGC | CCG | AGT | CAA | AAA | TTA | CAG | GTC | ATG | ACA | GCC | AAA | 336 |
| Glu | Gly | Ile | Gly | Ser | Pro | Ser | Gln | Lys | Leu | Gln | Val | Met | Thr | Ala | Lys | |
| | | | 100 | | | | | 105 | | | | | 110 | | | |

| TCA | CTA | ACT | TAT | GAG | GAT | TGC | AAA | AAC | GCA | ATT | TAT | AAA | AAA | GAC | TTT | 384 |
| Ser | Leu | Thr | Tyr | Glu | Asp | Cys | Lys | Asn | Ala | Ile | Tyr | Lys | Lys | Asp | Phe | |
| | | 115 | | | | | 120 | | | | | 125 | | | | |

| CGA | AAG | CCA | AAT | TTG | TGC | ACA | GGC | TA | | | | | | | | 410 |
| Arg | Lys | Pro | Asn | Leu | Cys | Thr | Gly | | | | | | | | | |
| | 130 | | | | 135 | | | | | | | | | | | |

(2) INFORMATION FOR SEQ ID NO:79:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:79:

Trp Val Val Thr Ala Ala His Cys Leu Arg Gly Lys Asp His Leu Leu
 1               5                  10                  15

Asp Lys Leu Phe Ile Ala Val Gly Leu Thr Asn Leu Gly Glu Gly Gly
             20                  25                  30

Thr Val Tyr Pro Val Glu Lys Gly Ile Met His Glu Glu Tyr Glu His
         35                  40                  45

Tyr Asp Ile Val Asn Asp Ile Ala Leu Ile Lys Val Lys Ser Pro Ile

```
                50                  55                  60
Glu Phe Asn Glu Lys Val Thr Thr Val Lys Leu Gly Glu Asp Tyr Val
 65                  70                  75                  80

Gly Gly Asp Val Gln Leu Arg Leu Thr Gly Trp Gly Val Thr Thr Asn
                 85                  90                  95

Glu Gly Ile Gly Ser Pro Ser Gln Lys Leu Gln Val Met Thr Ala Lys
                100                 105                 110

Ser Leu Thr Tyr Glu Asp Cys Lys Asn Ala Ile Tyr Lys Lys Asp Phe
            115                 120                 125

Arg Lys Pro Asn Leu Cys Thr Gly
            130                 135
```

(2) INFORMATION FOR SEQ ID NO:80:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..432

(xi) SEQUENCE DESCRIPTION: SEQ ID NO:80:

```
GTA ACT GCT GCA CAT TGC TTT TAT GGA ACG TTA TTT CCG ATT GGA TTC    48
Val Thr Ala Ala His Cys Phe Tyr Gly Thr Leu Phe Pro Ile Gly Phe
 1               5                  10                  15

TCT GCG AGA GCC GGC AGC AGT ACT GTG AAT TCA GGA GGA ACT GTG CAT    96
Ser Ala Arg Ala Gly Ser Ser Thr Val Asn Ser Gly Gly Thr Val His
                 20                  25                  30

ACA ATT TTG TAT TGG TAT ATT CAT CCA AAT TAT GAT TCA CAA AGT ACA   144
Thr Ile Leu Tyr Trp Tyr Ile His Pro Asn Tyr Asp Ser Gln Ser Thr
             35                  40                  45

GAC TTT GAT GTT TCT GTA GTT CGA CTA TTA TCT TCT TTA AAT TTG AAT   192
Asp Phe Asp Val Ser Val Val Arg Leu Leu Ser Ser Leu Asn Leu Asn
 50                  55                  60

GGA GGT TCT ATT CGA CCG GCT AGG TTA GTG GAT TCT GGA ACT GAT TTG   240
Gly Gly Ser Ile Arg Pro Ala Arg Leu Val Asp Ser Gly Thr Asp Leu
 65                  70                  75                  80

CCA GCC GGT GAG ATG GTT ACA GTA ACT GGA TGG GGA CGA CTT TCG GAA   288
Pro Ala Gly Glu Met Val Thr Val Thr Gly Trp Gly Arg Leu Ser Glu
                 85                  90                  95

AAT ACT TCT GTT CCC TCG CCA TCA ACT CTT CAA GGA GTT ACA GTA CCA   336
Asn Thr Ser Val Pro Ser Pro Ser Thr Leu Gln Gly Val Thr Val Pro
                100                 105                 110

GTT GTA AGT AAT TCG GAA TGT CAA CAA CAA TTG CAA AAT CAG ACA ATC   384
Val Val Ser Asn Ser Glu Cys Gln Gln Gln Leu Gln Asn Gln Thr Ile
             115                 120                 125

ACT GAC AAT ATG TTT TGT GCT GGT GAA TTA GAA GGA GGA AAG GAC TCT   432
Thr Asp Asn Met Phe Cys Ala Gly Glu Leu Glu Gly Gly Lys Asp Ser
            130                 135                 140

T                                                                  433
```

(2) INFORMATION FOR SEQ ID NO:81:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:81:

```
Val Thr Ala Ala His Cys Phe Tyr Gly Thr Leu Phe Pro Ile Gly Phe
 1               5                  10                  15

Ser Ala Arg Ala Gly Ser Ser Thr Val Asn Ser Gly Gly Thr Val His
            20                  25                  30

Thr Ile Leu Tyr Trp Tyr Ile His Pro Asn Tyr Asp Ser Gln Ser Thr
        35                  40                  45

Asp Phe Asp Val Ser Val Val Arg Leu Leu Ser Ser Leu Asn Leu Asn
    50                  55                  60

Gly Gly Ser Ile Arg Pro Ala Arg Leu Val Asp Ser Gly Thr Asp Leu
65                  70                  75                  80

Pro Ala Gly Glu Met Val Thr Val Thr Gly Trp Gly Arg Leu Ser Glu
                85                  90                  95

Asn Thr Ser Val Pro Ser Pro Ser Thr Leu Gln Gly Val Thr Val Pro
            100                 105                 110

Val Val Ser Asn Ser Glu Cys Gln Gln Gln Leu Gln Asn Gln Thr Ile
        115                 120                 125

Thr Asp Asn Met Phe Cys Ala Gly Glu Leu Glu Gly Gly Lys Asp Ser
    130                 135                 140
```

(2) INFORMATION FOR SEQ ID NO:82:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..426

(xi) SEQUENCE DESCRIPTION: SEQ ID NO:82:

```
GCC ACG ACA CCA AAT TCG AAC CTG AAG GTG CGT TTG GGC GAA TGG GAC      48
Ala Thr Thr Pro Asn Ser Asn Leu Lys Val Arg Leu Gly Glu Trp Asp
 1               5                  10                  15

GTT CGC GAC CAC GAT GAG CGA CTG AAC CAC GAG GAA TAC GCA ATC GAA      96
Val Arg Asp His Asp Glu Arg Leu Asn His Glu Glu Tyr Ala Ile Glu
            20                  25                  30

CGC AAA GAA GTT CAT CCT TCA TAT TCA CCA ACC GAT TTC CGG AAT GAT     144
Arg Lys Glu Val His Pro Ser Tyr Ser Pro Thr Asp Phe Arg Asn Asp
        35                  40                  45

GTA GCC TTA GTG AAA CTC GAT AGA ACT GTT ATT TTC AAA CAA CAT ATT     192
Val Ala Leu Val Lys Leu Asp Arg Thr Val Ile Phe Lys Gln His Ile
    50                  55                  60

TTA CCT GTC TGC TTA CCT CAT AAG CAA ATG AAA CTG GCT GGA AAA ATG     240
Leu Pro Val Cys Leu Pro His Lys Gln Met Lys Leu Ala Gly Lys Met
65                  70                  75                  80

GCA ACA GTC GCC GGA TGG GGA CGG ACG AGG CAC GGG CAG AGC ACT GTG     288
Ala Thr Val Ala Gly Trp Gly Arg Thr Arg His Gly Gln Ser Thr Val
                85                  90                  95

CCG GCT GTC TTA CAA GAA GTC GAT GTC GAG GTG ATT CCG AAT GAA AGA     336
Pro Ala Val Leu Gln Glu Val Asp Val Glu Val Ile Pro Asn Glu Arg
            100                 105                 110

TGC CAG AGG TGG TTC CGT GCT GCG GGT CGA CGA GAA ACC ATT CAC GAT     384
Cys Gln Arg Trp Phe Arg Ala Ala Gly Arg Arg Glu Thr Ile His Asp
```

```
                115                 120                      125
GTC TTT CTC TGC GCC GGA TAT AAA GAG GGT GGT CGT GAT TCA                  426
Val Phe Leu Cys Ala Gly Tyr Lys Glu Gly Gly Arg Asp Ser
    130                 135                      140

(2) INFORMATION FOR SEQ ID NO:83:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:83:

Ala Thr Thr Pro Asn Ser Asn Leu Lys Val Arg Leu Gly Glu Trp Asp
  1               5                  10                  15

Val Arg Asp His Asp Glu Arg Leu Asn His Glu Glu Tyr Ala Ile Glu
             20                  25                  30

Arg Lys Glu Val His Pro Ser Tyr Ser Pro Thr Asp Phe Arg Asn Asp
         35                  40                  45

Val Ala Leu Val Lys Leu Asp Arg Thr Val Ile Phe Lys Gln His Ile
     50                  55                  60

Leu Pro Val Cys Leu Pro His Lys Gln Met Lys Leu Ala Gly Lys Met
 65                  70                  75                  80

Ala Thr Val Ala Gly Trp Gly Arg Thr Arg His Gly Gln Ser Thr Val
                 85                  90                  95

Pro Ala Val Leu Gln Glu Val Asp Val Glu Val Ile Pro Asn Glu Arg
            100                 105                 110

Cys Gln Arg Trp Phe Arg Ala Ala Gly Arg Arg Glu Thr Ile His Asp
        115                 120                 125

Val Phe Leu Cys Ala Gly Tyr Lys Glu Gly Gly Arg Asp Ser
    130                 135                 140

(2) INFORMATION FOR SEQ ID NO:84:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..778

(xi) SEQUENCE DESCRIPTION: SEQ ID NO:84:

T GAT ACC TCA GAA TTG CCG GTA CAA AGG CGA ACG GTT TCG AGT GCG         46
  Asp Thr Ser Glu Leu Pro Val Gln Arg Arg Thr Val Ser Ser Ala
    1               5                  10                  15

GTT TGT CAA TTT TCG TGC GTC CTG GGC GGC GGA AAA CCT CTT GAC CTG        94
Val Cys Gln Phe Ser Cys Val Leu Gly Gly Gly Lys Pro Leu Asp Leu
                 20                  25                  30

TGC AGC GGC GGA ATG ATC TGG TCG TGC TGC GTC GAC AGG GAC ATT CGG       142
Cys Ser Gly Gly Met Ile Trp Ser Cys Cys Val Asp Arg Asp Ile Arg
             35                  40                  45

CCT GAG CCG CAG CAC CAG GGC GCT CTG CAG AAC GCA ACT TGT GGA GAA       190
Pro Glu Pro Gln His Gln Gly Ala Leu Gln Asn Ala Thr Cys Gly Glu
         50                  55                  60

TTG TAC ACG AGG TCT AAT AGA ATC GTA GGA GGT CAT TCA ACA GGA TTC       238
```

```
Leu Tyr Thr Arg Ser Asn Arg Ile Val Gly Gly His Ser Thr Gly Phe
         65                  70                  75

GGG TCT CAT CCT TGG CAG GCG GCT TTG ATC AAA TCA GGA TTT TTG AGT    286
Gly Ser His Pro Trp Gln Ala Ala Leu Ile Lys Ser Gly Phe Leu Ser
 80                  85                  90                  95

AAA AAA TTA TCT TGC GGT GGC GCT TTA GTT AGC GAT CGA TGG GTT ATA    334
Lys Lys Leu Ser Cys Gly Gly Ala Leu Val Ser Asp Arg Trp Val Ile
                100                 105                 110

ACT GCT GCA CAT TGC GTT GCC ACG ACA CCA AAT TCG AAC CTG AAG GTG    382
Thr Ala Ala His Cys Val Ala Thr Thr Pro Asn Ser Asn Leu Lys Val
            115                 120                 125

CGA TTG GGC GAA TGG GAC GTC CGC GAC CAC GAT GAG CGA CTG AAC CAC    430
Arg Leu Gly Glu Trp Asp Val Arg Asp His Asp Glu Arg Leu Asn His
        130                 135                 140

GAG GAA TAC GCA ATC GAA CGC AAA GAA GTT CAT CCT TCA TAT TCA CCA    478
Glu Glu Tyr Ala Ile Glu Arg Lys Glu Val His Pro Ser Tyr Ser Pro
    145                 150                 155

ACC GAT TTC CGG AAT GAT GTA GCC TTA GTG AAA CTC GAT AGA ACT GTT    526
Thr Asp Phe Arg Asn Asp Val Ala Leu Val Lys Leu Asp Arg Thr Val
160                 165                 170                 175

ATT TTC AAA CAA CAT ATT TTA CCT GTC TGC TTA CCT CAT AAG CAA ATG    574
Ile Phe Lys Gln His Ile Leu Pro Val Cys Leu Pro His Lys Gln Met
                180                 185                 190

AAA CTG GCT GGA AAA ATG GCA ACA GTC GCC GGA TGG GGA CGG ACG AGG    622
Lys Leu Ala Gly Lys Met Ala Thr Val Ala Gly Trp Gly Arg Thr Arg
            195                 200                 205

CAC GGG CAG AGC ACT GTG CCG GCT GTC TTA CAA GAA GTC GAT GTC GAG    670
His Gly Gln Ser Thr Val Pro Ala Val Leu Gln Glu Val Asp Val Glu
        210                 215                 220

GTG ATT CCG AAT GAA AGA TGC CAG AGG TGG TTC CGT GCT GCG GGT CGA    718
Val Ile Pro Asn Glu Arg Cys Gln Arg Trp Phe Arg Ala Ala Gly Arg
    225                 230                 235

CGA GAA ACC ATT CAC GAT GTC TTT CTC TGC GCC GGA TAT AAA GAG GGT    766
Arg Glu Thr Ile His Asp Val Phe Leu Cys Ala Gly Tyr Lys Glu Gly
240                 245                 250                 255

GGT CGT GAT TCA                                                    778
Gly Arg Asp Ser (2) INFORMATION FOR SEQ ID NO:85:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO:85:

Asp Thr Ser Glu Leu Pro Val Gln Arg Arg Thr Val Ser Ser Ala Val
 1               5                  10                  15

Cys Gln Phe Ser Cys Val Leu Gly Gly Lys Pro Leu Asp Leu Cys
                20                  25                  30

Ser Gly Gly Met Ile Trp Ser Cys Cys Val Asp Arg Asp Ile Arg Pro
            35                  40                  45

Glu Pro Gln His Gln Gly Ala Leu Gln Asn Ala Thr Cys Gly Glu Leu
    50                  55                  60

Tyr Thr Arg Ser Asn Arg Ile Val Gly Gly His Ser Thr Gly Phe Gly
 65                  70                  75                  80

Ser His Pro Trp Gln Ala Ala Leu Ile Lys Ser Gly Phe Leu Ser Lys
                85                  90                  95
```

```
Lys Leu Ser Cys Gly Gly Ala Leu Val Ser Asp Arg Trp Val Ile Thr
            100                 105                 110

Ala Ala His Cys Val Ala Thr Thr Pro Asn Ser Asn Leu Lys Val Arg
            115                 120                 125

Leu Gly Glu Trp Asp Val Arg Asp His Asp Glu Arg Leu Asn His Glu
            130                 135                 140

Glu Tyr Ala Ile Glu Arg Lys Glu Val His Pro Ser Tyr Ser Pro Thr
145                 150                 155                 160

Asp Phe Arg Asn Asp Val Ala Leu Val Lys Leu Asp Arg Thr Val Ile
                165                 170                 175

Phe Lys Gln His Ile Leu Pro Val Cys Leu Pro His Lys Gln Met Lys
            180                 185                 190

Leu Ala Gly Lys Met Ala Thr Val Ala Gly Trp Gly Arg Thr Arg His
            195                 200                 205

Gly Gln Ser Thr Val Pro Ala Val Leu Gln Glu Val Asp Val Glu Val
            210                 215                 220

Ile Pro Asn Glu Arg Cys Gln Arg Trp Phe Arg Ala Ala Gly Arg Arg
225                 230                 235                 240

Glu Thr Ile His Asp Val Phe Leu Cys Ala Gly Tyr Lys Glu Gly Gly
                245                 250                 255

Arg Asp Ser
```

(2) INFORMATION FOR SEQ ID NO:86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:86:

TAAWGGWCCA GARTCTCCTT GACA                                          24

(2) INFORMATION FOR SEQ ID NO:87:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:87:

GGAAACAGCT ATGACCATG                                                  19

(2) INFORMATION FOR SEQ ID NO:88:

(i) SEQUENCE CHARACTERISTICS:
        (A) LENGTH: 811 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..762

(xi) SEQUENCE DESCRIPTION: SEQ ID NO:88:

```
ATG CGG GGT TCT CAT CAT CAT CAT CAT CAT GGT ATG GCT AGC ATG ACT        48
Met Arg Gly Ser His His His His His His Gly Met Ala Ser Met Thr
 1               5                  10                  15

GGT GGA CAG CAA ATG GGT CGG GAT CTG TAC GAC GAT GAC GAT AAG AAG        96
Gly Gly Gln Gln Met Gly Arg Asp Leu Tyr Asp Asp Asp Asp Lys Lys
            20                  25                  30

GAT CCG TTA CCA GAT TCT TTC GAC TGG AGA ATT TAT GGA GCT GTT ACT       144
Asp Pro Leu Pro Asp Ser Phe Asp Trp Arg Ile Tyr Gly Ala Val Thr
        35                  40                  45

CCA GTT AAA GAT CAA TCT GTT TGT GGT TCC TGC TGG TCT TTC GGA ACA       192
Pro Val Lys Asp Gln Ser Val Cys Gly Ser Cys Trp Ser Phe Gly Thr
    50                  55                  60

ATT GGA GCT ATC GAA GGT GCA TAT TTC TTG AAA AAC GGC GGT AAT CTT       240
Ile Gly Ala Ile Glu Gly Ala Tyr Phe Leu Lys Asn Gly Gly Asn Leu
65                  70                  75                  80

GTA CGA TTG TCT CAA CAG GCT TTG ATT GAT TGT TCT TGG GGA TAT GGA       288
Val Arg Leu Ser Gln Gln Ala Leu Ile Asp Cys Ser Trp Gly Tyr Gly
                85                  90                  95

AAT AAT GGT TGT GAC GGT GGC GAG GAC TTC CGC GCT TAC CAA TGG ATG       336
Asn Asn Gly Cys Asp Gly Gly Glu Asp Phe Arg Ala Tyr Gln Trp Met
            100                 105                 110

ATG AAA CAT GGA GGA ATT CCT ACT GAA GAA GAT TAT GGT GGT TAC TTG       384
Met Lys His Gly Gly Ile Pro Thr Glu Glu Asp Tyr Gly Gly Tyr Leu
        115                 120                 125

GGA CAA GAT GGT TAC TGC CAT GTC AAC AAC GTT ACT TTA GTT GCT CCC       432
Gly Gln Asp Gly Tyr Cys His Val Asn Asn Val Thr Leu Val Ala Pro
    130                 135                 140

ATC ACA GGG TAT GTC AAC GTA ACA CGT AAT GAC GTT GAC GCT ATG AAG       480
Ile Thr Gly Tyr Val Asn Val Thr Arg Asn Asp Val Asp Ala Met Lys
145                 150                 155                 160

GTT GCC CTT CTT AAA CAC GGT CCA ATT TCG GTG GCC ATT GAC GCA TCA       528
Val Ala Leu Leu Lys His Gly Pro Ile Ser Val Ala Ile Asp Ala Ser
                165                 170                 175

CAC AAA ACA TTC AGT TTT TAC TCC AAC GGC GTT TAC TAC GAA CCG AAA       576
His Lys Thr Phe Ser Phe Tyr Ser Asn Gly Val Tyr Tyr Glu Pro Lys
            180                 185                 190

TGT GGC AAT AAA GAG GAC GAG TTG GAC CAT GCC GTA TTA GTA GTC GGT       624
Cys Gly Asn Lys Glu Asp Glu Leu Asp His Ala Val Leu Val Val Gly
        195                 200                 205

TAT GGT GAA ATC AAC AAC GAA CCT TAC TGG TTG GTC AAG AAT TCC TGG       672
Tyr Gly Glu Ile Asn Asn Glu Pro Tyr Trp Leu Val Lys Asn Ser Trp
    210                 215                 220

TCG AAT TTG TGG GGA AAT GAT GGT TAT ATT TTG ATG TCC GCC AGA AAT       720
Ser Asn Leu Trp Gly Asn Asp Gly Tyr Ile Leu Met Ser Ala Arg Asn
225                 230                 235                 240

AAT AAT TGC GGA GTT TTG ACT GAT CCA ACT TAT GTT ACT ATG              762
Asn Asn Cys Gly Val Leu Thr Asp Pro Thr Tyr Val Thr Met
                245                 250

TAACTTACTT TTTAGGAATT TGATTTTTAC GGCATGTAAA TGGAAGCTT                811
```

(2) INFORMATION FOR SEQ ID NO:89:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:89:

```
Met Arg Gly Ser His His His His His Gly Met Ala Ser Met Thr
 1               5                      10                  15

Gly Gly Gln Gln Met Gly Arg Asp Leu Tyr Asp Asp Asp Lys Lys
             20                  25                  30

Asp Pro Leu Pro Asp Ser Phe Asp Trp Arg Ile Tyr Gly Ala Val Thr
         35                  40                  45

Pro Val Lys Asp Gln Ser Val Cys Gly Ser Cys Trp Ser Phe Gly Thr
     50                  55                  60

Ile Gly Ala Ile Glu Gly Ala Tyr Phe Leu Lys Asn Gly Gly Asn Leu
 65              70                  75                      80

Val Arg Leu Ser Gln Gln Ala Leu Ile Asp Cys Ser Trp Gly Tyr Gly
                 85                  90                  95

Asn Asn Gly Cys Asp Gly Gly Glu Asp Phe Arg Ala Tyr Gln Trp Met
             100                 105                 110

Met Lys His Gly Gly Ile Pro Thr Glu Glu Asp Tyr Gly Gly Tyr Leu
             115                 120                 125

Gly Gln Asp Gly Tyr Cys His Val Asn Asn Val Thr Leu Val Ala Pro
             130                 135                 140

Ile Thr Gly Tyr Val Asn Val Thr Arg Asn Asp Val Asp Ala Met Lys
145                 150                 155                 160

Val Ala Leu Leu Lys His Gly Pro Ile Ser Val Ala Ile Asp Ala Ser
                 165                 170                 175

His Lys Thr Phe Ser Phe Tyr Ser Asn Gly Val Tyr Tyr Glu Pro Lys
             180                 185                 190

Cys Gly Asn Lys Glu Asp Glu Leu Asp His Ala Val Leu Val Val Gly
             195                 200                 205

Tyr Gly Glu Ile Asn Asn Glu Pro Tyr Trp Leu Val Lys Asn Ser Trp
             210                 215                 220

Ser Asn Leu Trp Gly Asn Asp Gly Tyr Ile Leu Met Ser Ala Arg Asn
225                 230                 235                 240

Asn Asn Cys Gly Val Leu Thr Asp Pro Thr Tyr Val Thr Met
                 245                 250
```

(2) INFORMATION FOR SEQ ID NO:90:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:90:

```
CCATTTACAT GCCGTAAAAA TCAAATTCCT AAAAAGTAAG TTACATAGTA ACATAAGTTG     60

GATCAGTCAA AACTCCGCAA TTATTATTTC TGGCGGACAT CAAAATATAA CCATCATTTC    120

CCCACAAATT CGACCAGGAA TTCTTGACCA ACCAGTAAGG TTCGTTGTTG ATTTCACCAT    180

AACCGACTAC TAATACGGCA TGGTCCAACT CGTCCTCTTT ATTGCCACAT TTCGGTTCGT    240

AGTAAACGCC GTTGGAGTAA AAACTGAATG TTTTGTGTGA TGCGTCAATG GCCACCGAAA    300

TTGGACCGTG TTTAAGAAGG GCAACCTTCA TAGCGTCAAC GTCATTACGT GTTACGTTGA    360

CATACCCTGT GATGGGAGCA ACTAAAGTAA CGTTGTTGAC ATGGCAGTAA CCATCTTGTC    420

CCAAGTAACC ACCATAATCT TCTTCAGTAG GAATTCCTCC ATGTTTCATC ATCCATTGGT    480

AAGCGCGGAA GTCCTCGCCA CCGTCACAAC CATTATTTCC ATATCCCCAA GAACAATCAA    540
```

```
TCAAAGCCTG TTGAGACAAT CGTACAAGAT TACCGCCGTT TTTCAAGAAA TATGCACCTT      600

CGATAGCTCC AATTGTTCCG AAAGACCAGC AGGAACCACA AACAGATTGA TCTTTAACTG      660

GAGTAACAGC TCCATAAATT CTCCAGTCGA AAGAATCTGG TAACGGATCC TTATCTGGTA      720

ACGGATCCTT CTTATCGTCA TCGTCGTACA GATCCCGACC CATTTCCTGT CCACCAGTCA      780

TGCTAGCCAT ACCATGATGA TGATGATGAT GAGAACCCCG CAT                       823

(2) INFORMATION FOR SEQ ID NO:91:

(i) SEQUENCE CHARACTERISTICS:
            (A) LENGTH: 762 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..762

(xi) SEQUENCE DESCRIPTION: SEQ ID NO:91:

ATG CGG GGT TCT CAT CAT CAT CAT CAT CAT GGT ATG GCT AGC ATG ACT        48
Met Arg Gly Ser His His His His His His Gly Met Ala Ser Met Thr
  1               5                  10                  15

GGT GGA CAG CAA ATG GGT CGG GAT CTG TAC GAC GAT GAC GAT AAG AAG        96
Gly Gly Gln Gln Met Gly Arg Asp Leu Tyr Asp Asp Asp Asp Lys Lys
                 20                  25                  30

GAT CCG TTA CCA GAT TCT TTC GAC TGG AGA ATT TAT GGA GCT GTT ACT       144
Asp Pro Leu Pro Asp Ser Phe Asp Trp Arg Ile Tyr Gly Ala Val Thr
             35                  40                  45

CCA GTT AAA GAT CAA TCT GTT TGT GGT TCC TGC TGG TCT TTC GGA ACA       192
Pro Val Lys Asp Gln Ser Val Cys Gly Ser Cys Trp Ser Phe Gly Thr
 50                  55                  60

ATT GGA GCT ATC GAA GGT GCA TAT TTC TTG AAA AAC GGC GGT AAT CTT       240
Ile Gly Ala Ile Glu Gly Ala Tyr Phe Leu Lys Asn Gly Gly Asn Leu
 65                  70                  75                  80

GTA CGA TTG TCT CAA CAG GCT TTG ATT GAT TGT TCT TGG GGA TAT GGA       288
Val Arg Leu Ser Gln Gln Ala Leu Ile Asp Cys Ser Trp Gly Tyr Gly
                 85                  90                  95

AAT AAT GGT TGT GAC GGT GGC GAG GAC TTC CGC GCT TAC CAA TGG ATG       336
Asn Asn Gly Cys Asp Gly Gly Glu Asp Phe Arg Ala Tyr Gln Trp Met
            100                 105                 110

ATG AAA CAT GGA GGA ATT CCT ACT GAA GAA GAT TAT GGT GGT TAC TTG       384
Met Lys His Gly Gly Ile Pro Thr Glu Glu Asp Tyr Gly Gly Tyr Leu
        115                 120                 125

GGA CAA GAT GGT TAC TGC CAT GTC AAC AAC GTT ACT TTA GTT GCT CCC       432
Gly Gln Asp Gly Tyr Cys His Val Asn Asn Val Thr Leu Val Ala Pro
    130                 135                 140

ATC ACA GGG TAT GTC AAC GTA ACA CGT AAT GAC GTT GAC GCT ATG AAG       480
Ile Thr Gly Tyr Val Asn Val Thr Arg Asn Asp Val Asp Ala Met Lys
145                 150                 155                 160

GTT GCC CTT CTT AAA CAC GGT CCA ATT TCG GTG GCC ATT GAC GCA TCA       528
Val Ala Leu Leu Lys His Gly Pro Ile Ser Val Ala Ile Asp Ala Ser
                165                 170                 175

CAC AAA ACA TTC AGT TTT TAC TCC AAC GGC GTT TAC TAC GAA CCG AAA       576
His Lys Thr Phe Ser Phe Tyr Ser Asn Gly Val Tyr Tyr Glu Pro Lys
            180                 185                 190

TGT GGC AAT AAA GAG GAC GAG TTG GAC CAT GCC GTA TTA GTA GTC GGT       624
Cys Gly Asn Lys Glu Asp Glu Leu Asp His Ala Val Leu Val Val Gly
        195                 200                 205
```

-continued

```
TAT GGT GAA ATC AAC AAC GAA CCT TAC TGG TTG GTC AAG AAT TCC TGG      672
Tyr Gly Glu Ile Asn Asn Glu Pro Tyr Trp Leu Val Lys Asn Ser Trp
    210                 215                 220

TCG AAT TTG TGG GGA AAT GAT GGT TAT ATT TTG ATG TCC GCC AGA AAT      720
Ser Asn Leu Trp Gly Asn Asp Gly Tyr Ile Leu Met Ser Ala Arg Asn
225                 230                 235                 240

AAT AAT TGC GGA GTT TTG ACT GAT CCA ACT TAT GTT ACT ATG              762
Asn Asn Cys Gly Val Leu Thr Asp Pro Thr Tyr Val Thr Met
                245                 250
```

(2) INFORMATION FOR SEQ ID NO:92:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:92:

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Lys
                20                  25                  30

Asp Pro Leu Pro Asp Ser Phe Asp Trp Arg Ile Tyr Gly Ala Val Thr
            35                  40                  45

Pro Val Lys Asp Gln Ser Val Cys Gly Ser Cys Trp Ser Phe Gly Thr
50                  55                  60

Ile Gly Ala Ile Glu Gly Ala Tyr Phe Leu Lys Asn Gly Gly Asn Leu
65                  70                  75                  80

Val Arg Leu Ser Gln Gln Ala Leu Ile Asp Cys Ser Trp Gly Tyr Gly
                85                  90                  95

Asn Asn Gly Cys Asp Gly Glu Asp Phe Arg Ala Tyr Gln Trp Met
                100                 105                 110

Met Lys His Gly Gly Ile Pro Thr Glu Glu Asp Tyr Gly Gly Tyr Leu
            115                 120                 125

Gly Gln Asp Gly Tyr Cys His Val Asn Asn Val Thr Leu Val Ala Pro
130                 135                 140

Ile Thr Gly Tyr Val Asn Val Thr Arg Asn Asp Val Asp Ala Met Lys
145                 150                 155                 160

Val Ala Leu Leu Lys His Gly Pro Ile Ser Val Ala Ile Asp Ala Ser
                165                 170                 175

His Lys Thr Phe Ser Phe Tyr Ser Asn Gly Val Tyr Tyr Glu Pro Lys
            180                 185                 190

Cys Gly Asn Lys Glu Asp Glu Leu Asp His Ala Val Leu Val Val Gly
                195                 200                 205

Tyr Gly Glu Ile Asn Asn Glu Pro Tyr Trp Leu Val Lys Asn Ser Trp
    210                 215                 220

Ser Asn Leu Trp Gly Asn Asp Gly Tyr Ile Leu Met Ser Ala Arg Asn
225                 230                 235                 240

Asn Asn Cys Gly Val Leu Thr Asp Pro Thr Tyr Val Thr Met
                245                 250
```

(2) INFORMATION FOR SEQ ID NO:93:

(i) SEQUENCE CHARACTERISTICS:
        (A) LENGTH: 783 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:93:

```
TTACATAGTA ACATAAGTTG GATCAGTCAA AACTCCGCAA TTATTATTTC TGGCGGACAT      60

CAAAATATAA CCATCATTTC CCCACAAATT CGACCAGGAA TTCTTGACCA ACCAGTAAGG     120

TTCGTTGTTG ATTTCACCAT AACCGACTAC TAATACGGCA TGGTCCAACT CGTCCTCTTT     180

ATTGCCACAT TTCGGTTCGT AGTAAACGCC GTTGGAGTAA AAACTGAATG TTTTGTGTGA     240

TGCGTCAATG GCCACCGAAA TTGGACCGTG TTTAAGAAGG GCAACCTTCA TAGCGTCAAC     300

GTCATTACGT GTTACGTTGA CATACCCTGT GATGGGAGCA ACTAAAGTAA CGTTGTTGAC     360

ATGGCAGTAA CCATCTTGTC CCAAGTAACC ACCATAATCT TCTTCAGTAG GAATTCCTCC     420

ATGTTTCATC ATCCATTGGT AAGCGCGGAA GTCCTCGCCA CCGTCACAAC CATTATTTCC     480

ATATCCCCAA GAACAATCAA TCAAAGCCTG TTGAGACAAT CGTACAAGAT TACCGCCGTT     540

TTTCAAGAAA TATGCACCTT CGATAGCTCC AATTGTTCCG AAAGACCAGC AGGAACCACA     600

AACAGATTGA TCTTTAACTG GAGTAACAGC TCCATAAATT CTCCAGTCGA AGAATCTGG      660

TAACGGATCC TTATCTGGTA ACGGATCCTT CTTATCGTCA TCGTCGTACA GATCCCGACC     720

CATTTCCTGT CCACCAGTCA TGCTAGCCAT ACCATGATGA TGATGATGAT GAGAACCCCG     780

CAT                                                                   783
```

(2) INFORMATION FOR SEQ ID NO:94:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..660

(xi) SEQUENCE DESCRIPTION: SEQ ID NO:94:

```
TTA CCA GAT TCT TTC GAC TGG AGA ATT TAT GGA GCT GTT ACT CCA GTT       48
Leu Pro Asp Ser Phe Asp Trp Arg Ile Tyr Gly Ala Val Thr Pro Val
 1               5                  10                  15

AAA GAT CAA TCT GTT TGT GGT TCC TGC TGG TCT TTC GGA ACA ATT GGA       96
Lys Asp Gln Ser Val Cys Gly Ser Cys Trp Ser Phe Gly Thr Ile Gly
            20                  25                  30

GCT ATC GAA GGT GCA TAT TTC TTG AAA AAC GGC GGT AAT CTT GTA CGA      144
Ala Ile Glu Gly Ala Tyr Phe Leu Lys Asn Gly Gly Asn Leu Val Arg
        35                  40                  45

TTG TCT CAA CAG GCT TTG ATT GAT TGT TCT TGG GGA TAT GGA AAT AAT      192
Leu Ser Gln Gln Ala Leu Ile Asp Cys Ser Trp Gly Tyr Gly Asn Asn
    50                  55                  60

GGT TGT GAC GGT GGC GAG GAC TTC CGC GCT TAC CAA TGG ATG ATG AAA      240
Gly Cys Asp Gly Gly Glu Asp Phe Arg Ala Tyr Gln Trp Met Met Lys
65                  70                  75                  80

CAT GGA GGA ATT CCT ACT GAA GAA GAT TAT GGT GGT TAC TTG GGA CAA      288
His Gly Gly Ile Pro Thr Glu Glu Asp Tyr Gly Gly Tyr Leu Gly Gln
                85                  90                  95

GAT GGT TAC TGC CAT GTC AAC AAC GTT ACT TTA GTT GCT CCC ATC ACA      336
Asp Gly Tyr Cys His Val Asn Asn Val Thr Leu Val Ala Pro Ile Thr
            100                 105                 110
```

```
GGG TAT GTC AAC GTA ACA CGT AAT GAC GTT GAC GCT ATG AAG GTT GCC      384
Gly Tyr Val Asn Val Thr Arg Asn Asp Val Asp Ala Met Lys Val Ala
        115                 120                 125

CTT CTT AAA CAC GGT CCA ATT TCG GTG GCC ATT GAC GCA TCA CAC AAA      432
Leu Leu Lys His Gly Pro Ile Ser Val Ala Ile Asp Ala Ser His Lys
    130                 135                 140

ACA TTC AGT TTT TAC TCC AAC GGC GTT TAC TAC GAA CCG AAA TGT GGC      480
Thr Phe Ser Phe Tyr Ser Asn Gly Val Tyr Tyr Glu Pro Lys Cys Gly
145                 150                 155                 160

AAT AAA GAG GAC GAG TTG GAC CAT GCC GTA TTA GTA GTC GGT TAT GGT      528
Asn Lys Glu Asp Glu Leu Asp His Ala Val Leu Val Val Gly Tyr Gly
            165                 170                 175

GAA ATC AAC AAC GAA CCT TAC TGG TTG GTC AAG AAT TCC TGG TCG AAT      576
Glu Ile Asn Asn Glu Pro Tyr Trp Leu Val Lys Asn Ser Trp Ser Asn
        180                 185                 190

TTG TGG GGA AAT GAT GGT TAT ATT TTG ATG TCC GCC AGA AAT AAT AAT      624
Leu Trp Gly Asn Asp Gly Tyr Ile Leu Met Ser Ala Arg Asn Asn Asn
    195                 200                 205

TGC GGA GTT TTG ACT GAT CCA ACT TAT GTT ACT ATG                      660
Cys Gly Val Leu Thr Asp Pro Thr Tyr Val Thr Met
210                 215                 220

(2) INFORMATION FOR SEQ ID NO:95:

(i) SEQUENCE CHARACTERISTICS:
        (A) LENGTH: 220 amino acids
        (B) TYPE: amino acid
        (D) TOPOLOGY: linear (ii) MOLECULE TYPE: protein (xi) SEQUENCE DESCRIPTION: SEQ ID NO:95:

Leu Pro Asp Ser Phe Asp Trp Arg Ile Tyr Gly Ala Val Thr Pro Val
  1               5                  10                  15

Lys Asp Gln Ser Val Cys Gly Ser Cys Trp Ser Phe Gly Thr Ile Gly
                20                  25                  30

Ala Ile Glu Gly Ala Tyr Phe Leu Lys Asn Gly Gly Asn Leu Val Arg
            35                  40                  45

Leu Ser Gln Gln Ala Leu Ile Asp Cys Ser Trp Gly Tyr Gly Asn Asn
        50                  55                  60

Gly Cys Asp Gly Gly Glu Asp Phe Arg Ala Tyr Gln Trp Met Met Lys
 65                  70                  75                  80

His Gly Gly Ile Pro Thr Glu Glu Asp Tyr Gly Gly Tyr Leu Gly Gln
                85                  90                  95

Asp Gly Tyr Cys His Val Asn Asn Val Thr Leu Val Ala Pro Ile Thr
                100                 105                 110

Gly Tyr Val Asn Val Thr Arg Asn Asp Val Asp Ala Met Lys Val Ala
            115                 120                 125

Leu Leu Lys His Gly Pro Ile Ser Val Ala Ile Asp Ala Ser His Lys
        130                 135                 140

Thr Phe Ser Phe Tyr Ser Asn Gly Val Tyr Tyr Glu Pro Lys Cys Gly
145                 150                 155                 160

Asn Lys Glu Asp Glu Leu Asp His Ala Val Leu Val Val Gly Tyr Gly
                165                 170                 175

Glu Ile Asn Asn Glu Pro Tyr Trp Leu Val Lys Asn Ser Trp Ser Asn
            180                 185                 190

Leu Trp Gly Asn Asp Gly Tyr Ile Leu Met Ser Ala Arg Asn Asn Asn
        195                 200                 205
```

```
Cys Gly Val Leu Thr Asp Pro Thr Tyr Val Thr Met
    210                 215                 220
```

(2) INFORMATION FOR SEQ ID NO:96:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:96:

```
Xaa Pro Pro Pro Glu Met Leu Gly Gly Pro Ser Ile Phe Ile Phe Pro
1               5                   10                  15

Pro Lys Lys Lys Asp Asp Leu Leu Ile
            20                  25
```

(2) INFORMATION FOR SEQ ID NO:97:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:97:

TTGGGATACA CTTTGACTGT TAACC                                      25

(2) INFORMATION FOR SEQ ID NO:98:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:98:

GTGAGCAACC ATTATTTCCA TATC                                       24

(2) INFORMATION FOR SEQ ID NO:99:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:99:

TGGGTWGTWA CWGCWGCWCA TTG                                          23

(2) INFORMATION FOR SEQ ID NO:100:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:100:

-continued

```
ATTCCTCGTG GTTCAGTCGC TC                                          22

(2) INFORMATION FOR SEQ ID NO:101:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:101:

GAAGATGTWG ATATTTCWAC ATGTGG                                      26

(2) INFORMATION FOR SEQ ID NO:102:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:102:

GAAAATGAAA TCCACTTAAA CATTACG                                     27

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:103:

CTCTTATTGT ACGAGGGATG C                                           21
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein selected from the group consisting of
    a. protein comprising amino acid sequence selected from the group consisting of SEQ ID NO:2, SEQ ID NO:8, SEQ ID NO:89 and SEQ ID NO:95; and,
    b. a flea protein comprising a homologue of a protein comprising an amino acid seuence selected from the group consisting of SEQ ID NO:2, SEQ ID NO:8, SEQ ID NO:89 and SEQ ID NO:95; wherein said homologe has at least a 6 contiguous amino acid portion of a sequence selected from the group consisfing ofSEQ ID NO:2, SEQ ID NO:8, SEQ ID NO:89 and SEQ ID NO:95.

2. The protein of claim 1, wherein said protein comprises an amino acid sequence selected from the group consisting of SEQ ID NO:2, SEQ ID NO:8, SEQ ID NO:89 and SEQ ID NO:95.

3. A method to identify a compound capable of inhibiting flea protease activity, said method comprising:
    (a) contacting an isolated flea protease protein comprising an amino acid sequence selected from the group consisting of SEQ ID NO:2 SEQ ID NO:8, SEQ ID NO:89 and SEQ ID NO:95 with a putative inhibitory compound under conditions in which, in the absence of said compound, said protein has proteolytic activity; and
    (b) determining if said putative inhibitory compound inhibits said activity.

* * * * *